United States Patent
Lee et al.

(10) Patent No.: US 10,312,454 B2
(45) Date of Patent: Jun. 4, 2019

(54) COMPOUND FOR ORGANIC OPTOELECTRIC DEVICE, ORGANIC OPTOELECTRIC DEVICE AND DISPLAY DEVICE

(71) Applicant: SAMSUNG SDI CO., LTD., Yongin-si, Gyeonggi-do (KR)

(72) Inventors: Sangshin Lee, Suwon-si (KR); Dong Min Kang, Suwon-si (KR); Youngkwon Kim, Suwon-si (KR); Jun Seok Kim, Suwon-si (KR); Eun Sun Yu, Suwon-si (KR); Byoungkwan Lee, Suwon-si (KR); Kipo Jang, Suwon-si (KR); Sujin Han, Suwon-si (KR)

(73) Assignee: Samsung SDI Co., Ltd., Yongin-Si, Gyeonggi-do (KR)

(*) Notice: Subject to any disclaimer, the term of this patent is extended or adjusted under 35 U.S.C. 154(b) by 38 days.

(21) Appl. No.: 15/560,696

(22) PCT Filed: Feb. 17, 2016

(86) PCT No.: PCT/KR2016/001610
§ 371 (c)(1),
(2) Date: Sep. 22, 2017

(87) PCT Pub. No.: WO2016/204375
PCT Pub. Date: Dec. 22, 2016

(65) Prior Publication Data
US 2018/0114917 A1    Apr. 26, 2018

(30) Foreign Application Priority Data
Jun. 17, 2015    (KR) .................. 10-2015-0086001

(51) Int. Cl.
*H01L 51/00* (2006.01)
*C07D 403/10* (2006.01)
*C07D 251/12* (2006.01)
*C09K 11/06* (2006.01)
*H01L 51/50* (2006.01)
*C07D 251/24* (2006.01)
(Continued)

(52) U.S. Cl.
CPC ........ *H01L 51/0067* (2013.01); *C07D 251/12* (2013.01); *C07D 251/24* (2013.01);
(Continued)

(58) Field of Classification Search
CPC . H01L 51/0067; H01L 51/50; H01L 51/5072; H01L 51/5096; H01L 51/5016;
(Continued)

(56) References Cited

U.S. PATENT DOCUMENTS 6,057,048 A * 5/2000 Hu ..................... C07D 251/24
                                                313/504
6,225,467 B1 * 5/2001 Esteghamatian .... C07D 251/24
                                                428/690
(Continued)

FOREIGN PATENT DOCUMENTS

JP    2006-199679 A    8/2006
JP    2006-225320 A    8/2006
(Continued)

*Primary Examiner* — Eli D. Strah
(74) *Attorney, Agent, or Firm* — Lee & Morse, P.C.

(57) ABSTRACT

The present invention relates to a compound for an organic optoelectric device, an organic optoelectric device, to which the compound is applied, and a display device, wherein the compound is represented by chemical formula 1. The detailed contents regarding chemical formula 1 are the same as defined in the specification.

12 Claims, 1 Drawing Sheet

(51) Int. Cl.
  *B32B 17/10* (2006.01)
  *C07D 251/04* (2006.01)
  *C07D 251/00* (2006.01)
  *C08K 5/3492* (2006.01)

(52) U.S. Cl.
  CPC ............ *C07D 403/10* (2013.01); *C09K 11/06* (2013.01); *H01L 51/50* (2013.01); *B32B 17/10669* (2013.01); *B32B 2457/206* (2013.01); *C07D 251/00* (2013.01); *C07D 251/04* (2013.01); *C08K 5/3492* (2013.01); *C09K 2211/1018* (2013.01); *H01L 51/5016* (2013.01); *H01L 51/5072* (2013.01); *H01L 51/5096* (2013.01)

(58) Field of Classification Search
  CPC .. C07D 251/24; C07D 251/12; C07D 251/00; C07D 251/04; C07D 403/10; C09K 11/06; C09K 2211/1018; C08K 5/3492; B32B 2457/206; B32B 17/10669
  See application file for complete search history.

(56) References Cited

U.S. PATENT DOCUMENTS

| | | | |
|---|---|---|---|
| 6,229,012 B1* | 5/2001 | Hu | C07D 251/24 544/180 |
| 6,821,643 B1* | 11/2004 | Hu | C09K 11/06 252/301.23 |
| 2011/0220880 A1 | 9/2011 | Cheng et al. | |

FOREIGN PATENT DOCUMENTS

| | | |
|---|---|---|
| JP | 2007-314503 A | 12/2007 |
| JP | 2008-280330 A | 11/2008 |
| JP | 2013-510889 A | 3/2013 |
| JP | 2014-507383 A | 3/2014 |
| KR | 10-2009-0008737 A | 1/2009 |
| KR | 10-2009-0047547 A | 5/2009 |
| KR | 10-2011-0068514 A | 6/2011 |
| KR | 10-2011-0088513 A | 8/2011 |
| KR | 10-2011-0106325 A | 9/2011 |
| KR | 10-2012-0046778 A | 5/2012 |
| KR | 10-2013-0098226 A | 9/2013 |
| KR | 10-2013-0130777 A | 12/2013 |
| KR | 10-2013-0130788 | 12/2013 |
| KR | 10-2014-0009919 | 1/2014 |
| KR | 10-2014-0087804 A | 7/2014 |
| KR | 10-2014-0097299 A | 8/2014 |
| KR | 10-2015-0037318 A | 4/2015 |
| KR | 10-2016-0117492 | 10/2016 |
| WO | WO 2005-085387 A | 9/2005 |
| WO | WO 2010-038854 A | 4/2010 |
| WO | WO 2013/068376 A1 | 5/2013 |
| WO | WO 2014/010824 A1 | 1/2014 |
| WO | WO 2015/154843 A1 | 10/2015 |

* cited by examiner

[Fig. 1]
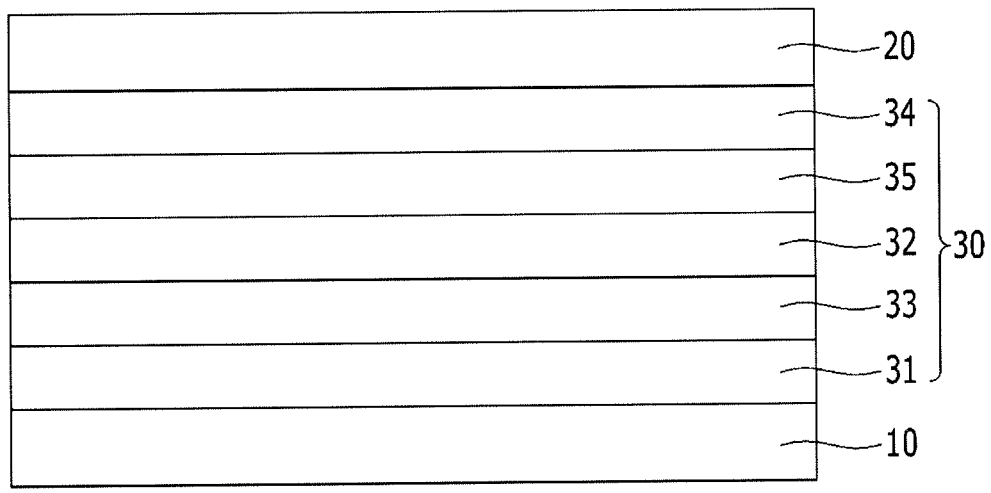
[Fig. 2]
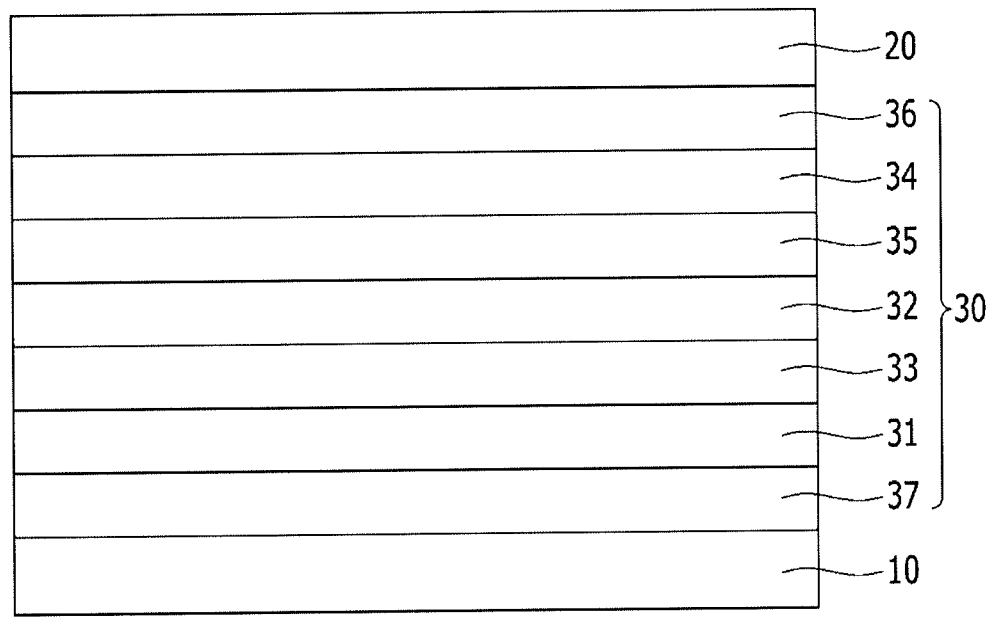

COMPOUND FOR ORGANIC OPTOELECTRIC DEVICE, ORGANIC OPTOELECTRIC DEVICE AND DISPLAY DEVICE

CROSS REFERENCE TO RELATED APPLICATIONS

This is the U.S. national phase application based on PCT Application No. PCT/KR2016/001610, filed on Feb. 17, 2016, which is based on Korean Patent Application No. 10-2015-0086001, filed on Jun. 17, 2015, the entire contents of all of which are hereby incorporated by reference.

TECHNICAL FIELD

A compound for an organic optoelectric device, an organic optoelectric device, and a display device are disclosed.

BACKGROUND ART

An organic optoelectric device (organic optoelectric diode) is a device that converts electrical energy into photoenergy, and vice versa.

An organic optoelectric device may be classified as follows in accordance with its driving principle. One is a photoelectric device where excitons are generated by photoenergy, separated into electrons and holes, and are transferred to different electrodes to generate electrical energy, and the other is a light emitting device where a voltage or a current is supplied to an electrode to generate photoenergy from electrical energy.

Examples of the organic optoelectric device may be an organic photoelectric device, an organic light emitting diode, an organic solar cell, and an organic photo conductor drum.

Of these, an organic light emitting diode (OLED) has recently drawn attention due to an increase in demand for flat panel displays. The organic light emitting diode is a device converting electrical energy into light by applying current to an organic light emitting material, and has a structure in which an organic layer is disposed between an anode and a cathode. Herein, the organic layer may include a light emitting layer and optionally an auxiliary layer, and the auxiliary layer may be, for example at least one layer selected from a hole injection layer, a hole transport layer, an electron blocking layer, an electron transport layer, an electron injection layer, and a hole blocking layer.

Performance of an organic light emitting diode may be affected by characteristics of the organic layer, and among them, may be mainly affected by characteristics of an organic material of the organic layer.

Particularly, development for an organic material being capable of increasing hole and electron mobility and simultaneously increasing electrochemical stability is needed so that the organic light emitting diode may be applied to a large-size flat panel display.

DISCLOSURE

Technical Problem

An embodiment provides a compound for an organic optoelectric device capable of realizing an organic optoelectric device having high efficiency and a long life-span.

Another embodiment provides an organic optoelectric device including the compound for an organic optoelectric device.

Yet another embodiment provides a display device including the organic optoelectric device.

Technical Solution

According to an embodiment, a compound for an organic optoelectric device represented by Chemical Formula 1 is provided.

[Chemical Formula 1]

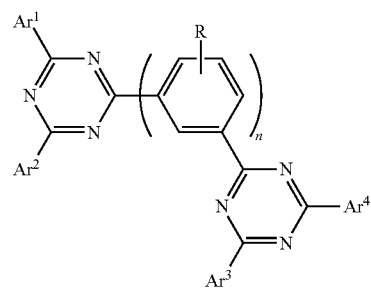

In Chemical Formula I, $Ar^1$ to $Ar^4$ are independently a substituted or unsubstituted C6 to C30 aryl group, R is independently hydrogen, deuterium, a substituted or unsubstituted C1 to C30 alkyl group, a substituted or unsubstituted C3 to C30 cycloalkyl group, a substituted or unsubstituted C6 to C30 aryl group, a substituted or unsubstituted C1 to C30 alkoxy group, a substituted or unsubstituted C3 to C40 silyl group, or a combination thereof, each of R is the same or different, and n is an integer of 2 to 10.

Herein, "substituted" refers to replacement of at least one hydrogen by deuterium, a cyano group, a nitro group, a halogen-substituted C1 to C10 alkyl group, a C1 to C40 silyl group, a C1 to C30 alkyl group, a C1 to C10 alkylsilyl group, a C6 to C30 arylsilyl group, a C3 to C30 cycloalkyl group, a C2 to C30 heterocycloalkyl group, a C6 to C30 aryl group, or a C1 to C20 alkoxy group.

According to another embodiment, an organic optoelectric device includes an anode and a cathode facing each other and at least one organic layer disposed between the anode and the cathode, wherein the organic layer includes the compound for an organic optoelectric device.

According to yet another embodiment, a display device including the organic optoelectric device is provided.

Advantageous Effects

An organic optoelectric device having high efficiency and a long life-span may be realized.

DESCRIPTION OF THE DRAWINGS

FIGS. 1 and 2 are cross-sectional views showing organic light emitting diodes according embodiments.

MODE FOR INVENTION

Hereinafter, embodiments of the present invention are described in detail. However, these embodiments are exemplary, the present invention is not limited thereto and the present invention is defined by the scope of claims.

In the specification, when a definition is not otherwise provided, "substituted" refers to replacement of at least one hydrogen of a substituent or a compound by deuterium, a cyano group, a nitro group, a halogen-substituted C1 to C10 alkyl group, a C1 to C40 silyl group, a C1 to C30 alkyl group, a C1 to C10 alkylsilyl group, a C6 to C30 arylsilyl group, a C3 to C30 cycloalkyl group, a C2 to C30 heterocycloalkyl group, a C6 to C30 aryl group, or a C1 to C20 alkoxy group.

In the specification, when a definition is not otherwise provided, "hetero" refers to one including one to three heteroatoms selected from N, O, S, P, and Si. and remaining carbons in one functional group.

In the specification, when a definition is not otherwise provided, "halogen" refers to F, Cl, Br, or I.

In the specification, when a definition is not otherwise provided, "an alkyl group" refers to an aliphatic hydrocarbon group. The alkyl group may be "a saturated alkyl group" without any double bond or triple bond.

The alkyl group may be a C1 to C30 alkyl group. More specifically, the alkyl group may be a C1 to C20 alkyl group or a C1 to C10 alkyl group. For example, a C1 to C4 alkyl group may have one to four carbon atoms in the alkyl chain, and may be selected from methyl, ethyl, propyl, iso-propyl, n-butyl, iso-butyl, sec-butyl, and t-butyl.

Specific examples of the alkyl group may be a methyl group, an ethyl group, a propyl group, an isopropyl group, a butyl group, an isobutyl group, a t-butyl group, a pentyl group, a hexyl group, a cyclopropyl group, a cyclobutyl group, a cyclopentyl group, a cyclohexyl group, and the like.

In the specification, "an aryl group" refers to a group including at least one hydrocarbon aromatic moiety, and
all the elements of the hydrocarbon aromatic moiety have p-orbitals which form conjugation, for example a phenyl group, a naphthyl group, and the like,
two or more hydrocarbon aromatic moieties may be linked by a sigma bond and may be, for example a biphenyl group, a terphenyl group, a quarterphenyl group, and the like, and
two or more hydrocarbon aromatic moieties are fused directly or indirectly to provide a non-aromatic fused ring. For example, it may be a fluorenyl group.

The aryl group may include a monocyclic, polycyclic or fused ring polycyclic (i.e., rings sharing adjacent pairs of carbon atoms) functional group.

More specifically, the substituted or unsubstituted C6 to C30 aryl group may be a substituted or unsubstituted phenyl group, a substituted or unsubstituted naphthyl group, a substituted or unsubstituted anthracenyl group, a substituted or unsubstituted phenanthryl group, a substituted or unsubstituted naphthacenyl group, a substituted or unsubstituted pyrenyl group, a substituted or unsubstituted biphenyl group, a substituted or unsubstituted o-terphenyl group, a substituted or unsubstituted p-terphenyl group, a substituted or unsubstituted m-terphenyl group, a substituted or unsubstituted chrysenyl group, a substituted or unsubstituted triphenylenyl group, a substituted or unsubstituted perylenyl group, a substituted or unsubstituted fluorenyl group, a substituted or unsubstituted indenyl group, or a combination thereof, but is not limited thereto.

In the present specification, hole characteristics refer to an ability to donate an electron to form a hole when an electric field is applied and that a hole formed in the anode may be easily injected into the light emitting layer and transported in the light emitting layer due to conductive characteristics according to a highest occupied molecular orbital (HOMO) level.

In addition, electron characteristics refer to an ability to accept an electron when an electric field is applied and that electron formed in the cathode may be easily injected into the light emitting layer and transported in the light emitting layer due to conductive characteristics according to a lowest unoccupied molecular orbital (LUMO) level.

Hereinafter, a compound for an organic optoelectric device according to an embodiment is described.

A compound for an organic optoelectric device according to an embodiment is represented by Chemical Formula I.

[Chemical Formula 1]

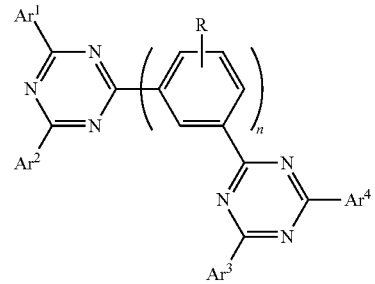

In Chemical Formula I,
$Ar^1$ to $Ar^4$ are independently a substituted or unsubstituted C6 to C30 aryl group,
R is independently hydrogen, deuterium, a substituted or unsubstituted C1 to C30 alkyl group, a substituted or unsubstituted C3 to C30 cycloalkyl group, a substituted or unsubstituted C6 to C30 aryl group, a substituted or unsubstituted C1 to C30 alkoxy group, a substituted or unsubstituted C3 to C40 silyl group, or a combination thereof,
each of R is the same or different,
n is an integer of 2 to 10.

Herein "substituted" refers to replacement of at least one hydrogen by deuterium, a cyano group, a nitro group, a halogen-substituted C1 to C10 alkyl group, a C1 to C40 silyl group, a C1 to C30 alkyl group, a C1 to C10 alkylsilyl group, a C6 to C30 arylsilyl group, a C3 to C30 cycloalkyl group, a C2 to C30 heterocycloalkyl group, a C6 to C30 aryl group, or a C1 to C20 alkoxy group.

n may be greater than or equal to 2, all the linking groups may be linked at a meta position, and each substituent, R of the linking groups may be the same or different.

The compound for an organic optoelectric device represented by Chemical Formula I is a dimer-shaped or ditriazine-shaped material having triazinyl groups bonded at both sides of two or more phenyl linkers linked at the meta position.

When two or more linking groups are linked at the meta position, the compound may have less crystallinity as well as maintain charge mobility and thus show improved processibility during deposition and solution processes for manufacturing a device compared with a para position and in addition, increase a charge stability effect due to the triazinyl group included as the dimer shape with a linker in a center when electrons are injected and thus mobility of the electrons.

Herein, each triazinyl group may further include two aryl substituents to adjust the symmetric/asymmetric substituents and accordingly diversify molecular solubility and a molecular interaction on a film and thus, change electrical characteristics in the molecule.

Specifically, the n may be on integer among 2 to 5, more specifically, a biphenylene group, a terphenylene group, a quaterphenylene group, and the like sequentially linked at the meta position.

The compound for an organic optoelectric device may be for example represented by one of Chemical Formulae I-1 to I-10 according to the number of a phenylene group in the linker and the kind of a substituent.

[Chemical Formula I-1]

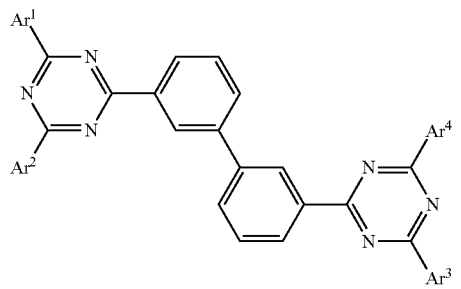

[Chemical Formula I-2]

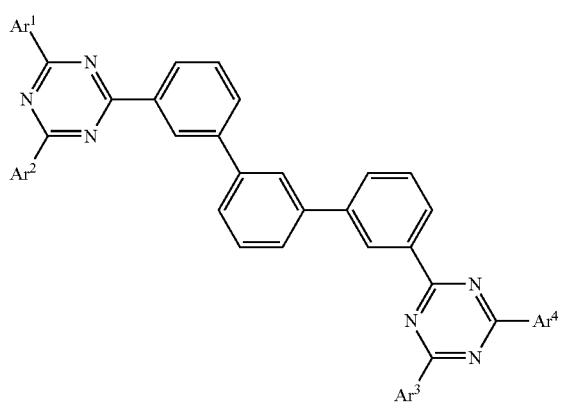

[Chemical Formula I-3]

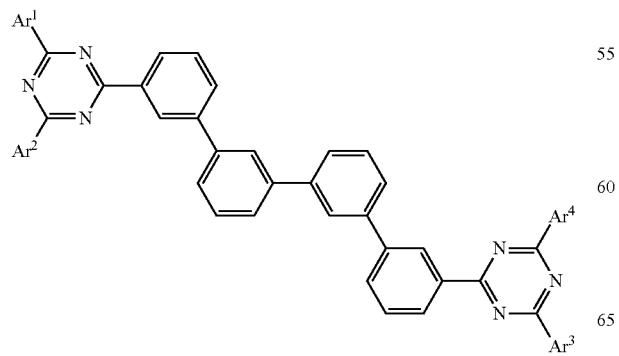

[Chemical Formula I-4]

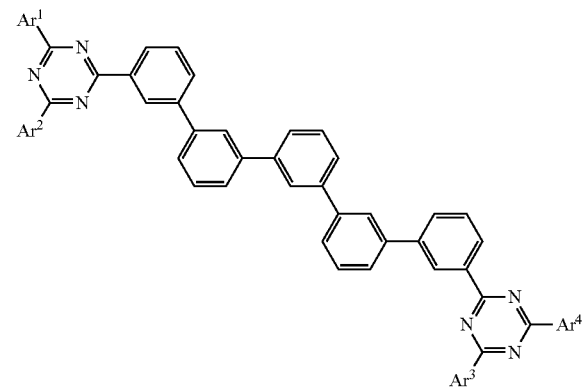

[Chemical Formula I-5]

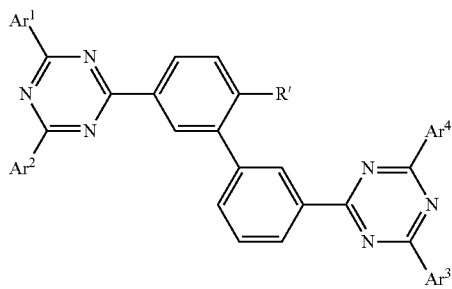

[Chemical Formula I-6]

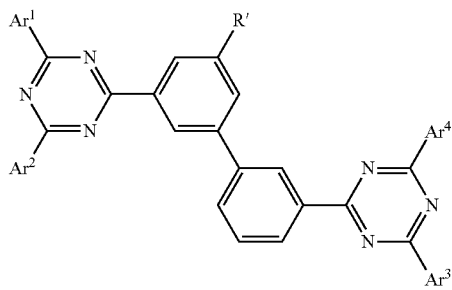

[Chemical Formula I-7]

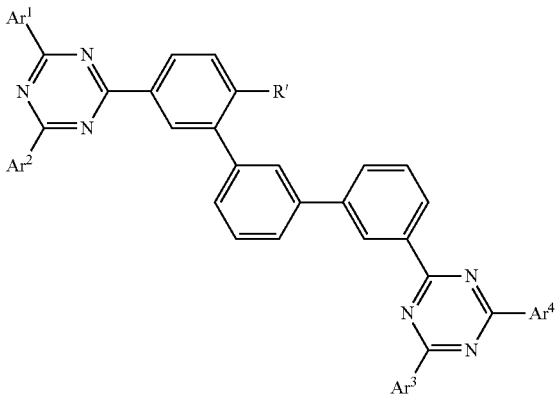

[Chemical Formula I-8]

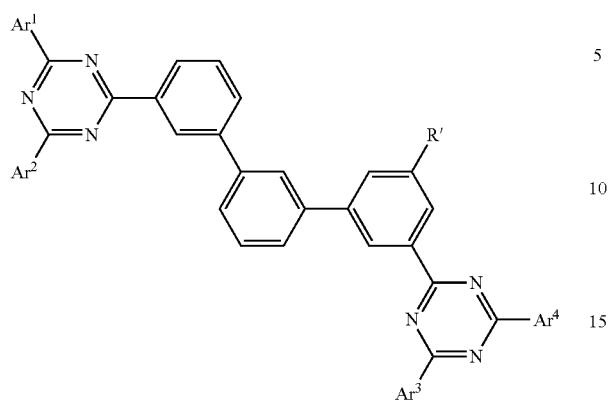

[Group 1]

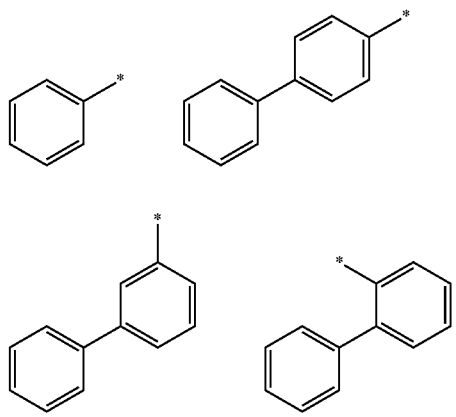

[Chemical Formula I-9]

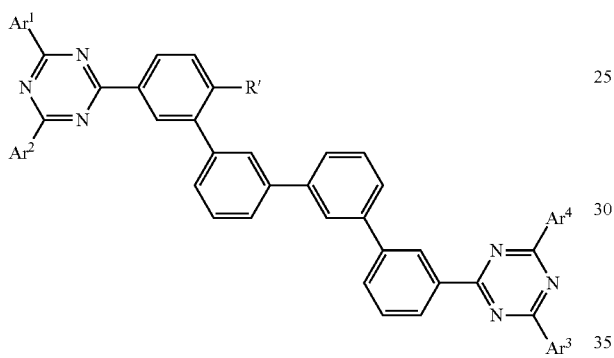

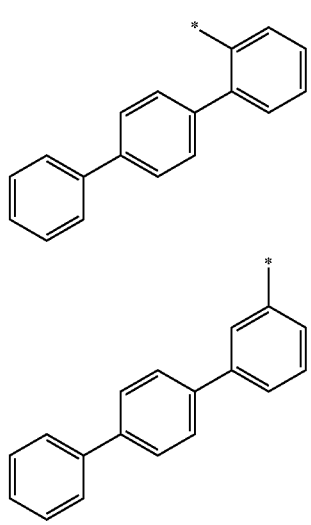

[Chemical Formula I-10]

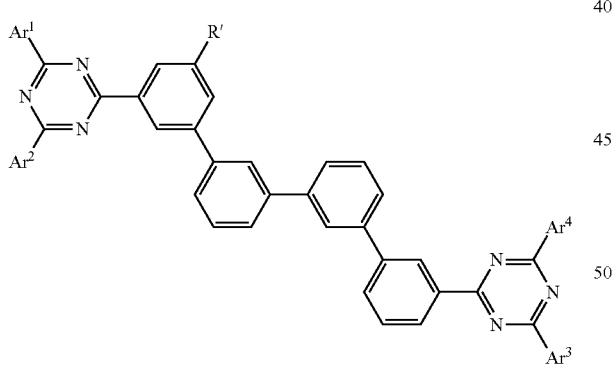

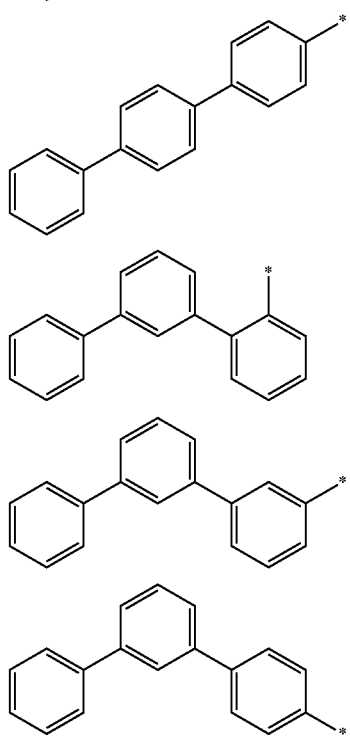

In Chemical Formulae I-1 to I-10, $Ar^1$ to $Ar^4$ are the same as described above, and R' is deuterium, a substituted or unsubstituted C1 to C10 alkyl group, or a substituted or unsubstituted C6 to C20 aryl group.

$Ar^1$ to $Ar^4$ may be specifically a substituted or unsubstituted phenyl group, a substituted or unsubstituted biphenyl group, a substituted or unsubstituted terphenyl group, or a substituted or unsubstituted quaterphenyl group, and may be for example selected from substituted or unsubstituted groups of Group I.

-continued
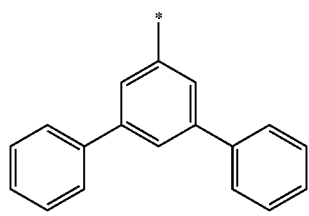
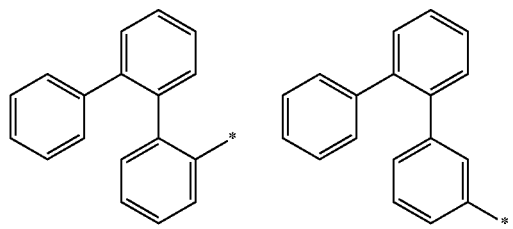
-continued
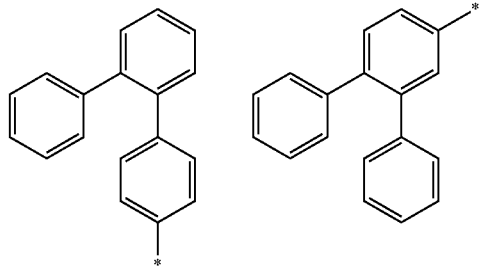
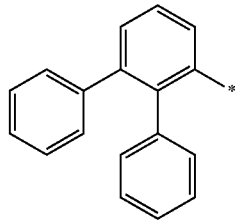
In Group I, * indicates a binding site with an adjacent atom.
The compound for an organic optoelectric device represented by Chemical Formula I may be for example one of compounds of Group II, but is not limited thereto.
[Group II]
1
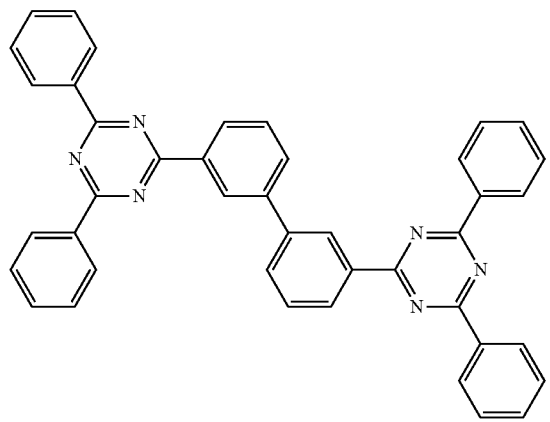
2
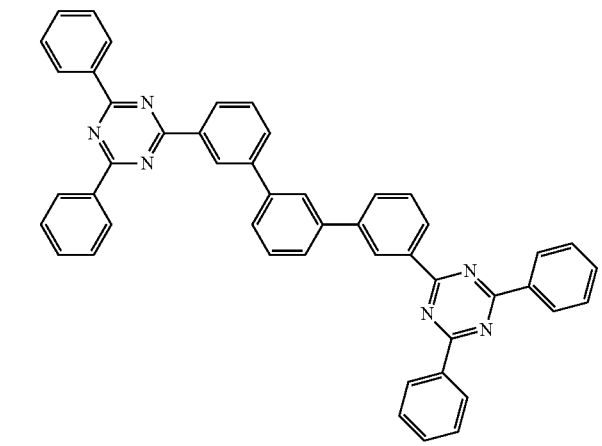

-continued
3
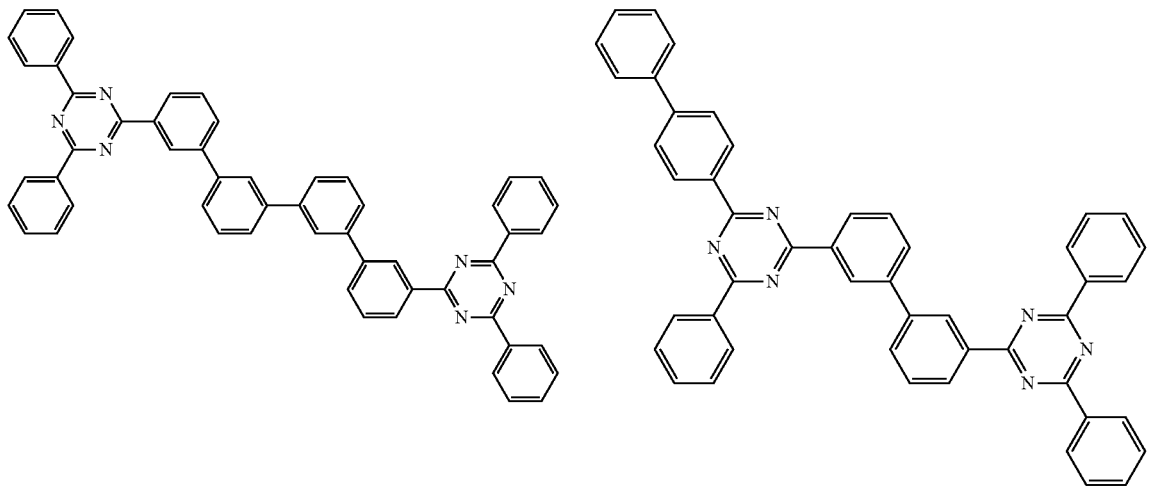
4
5
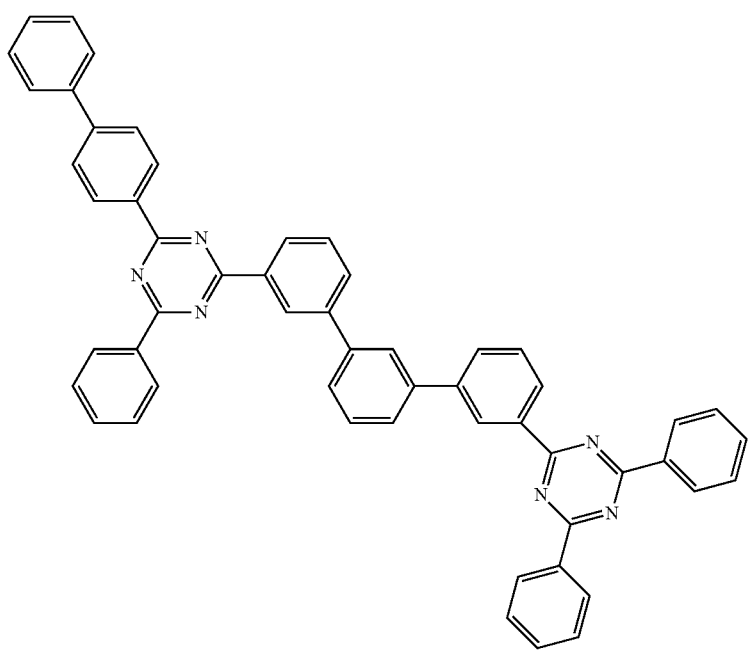

-continued
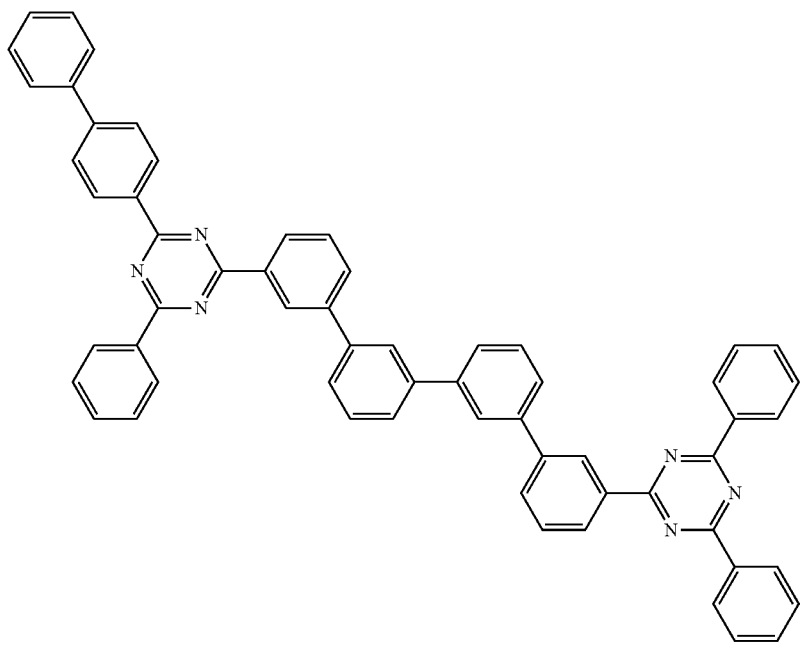
6
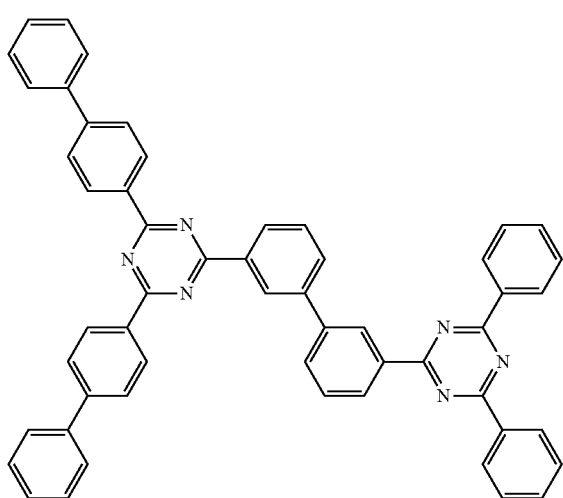
7

-continued
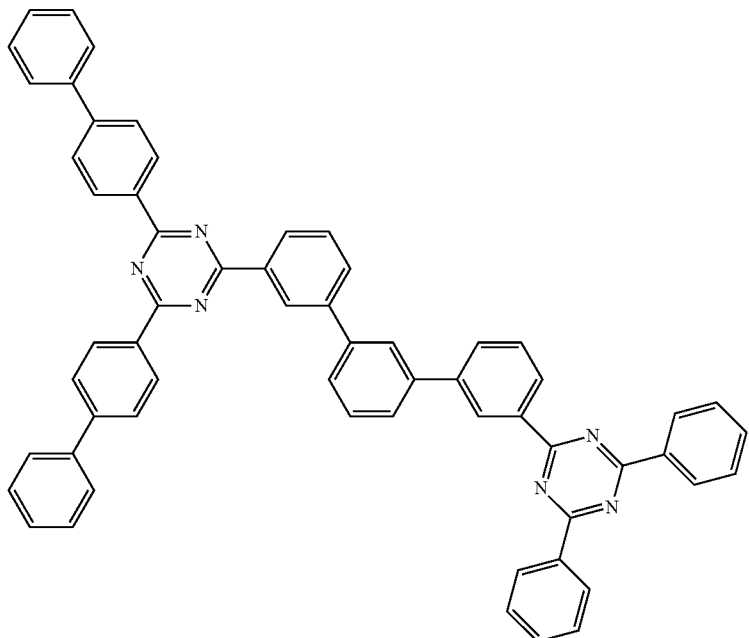
8
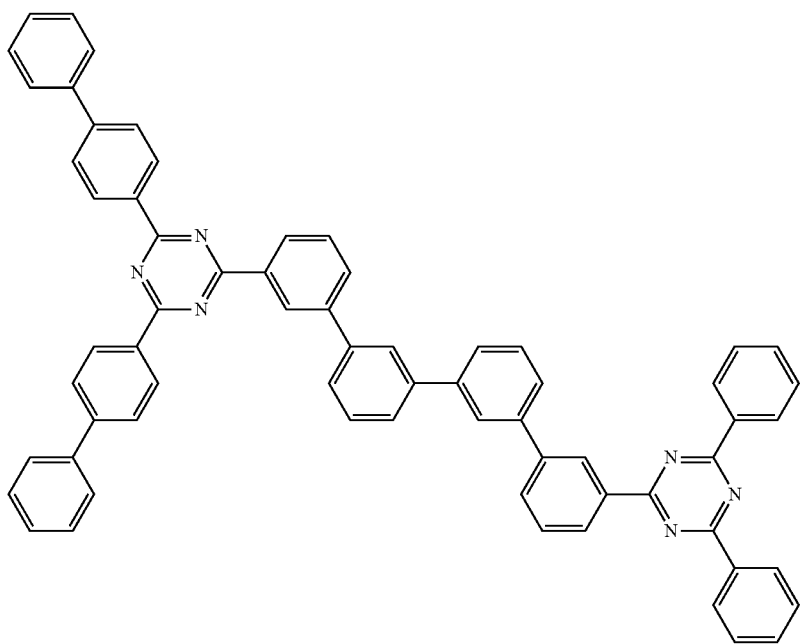
9

-continued
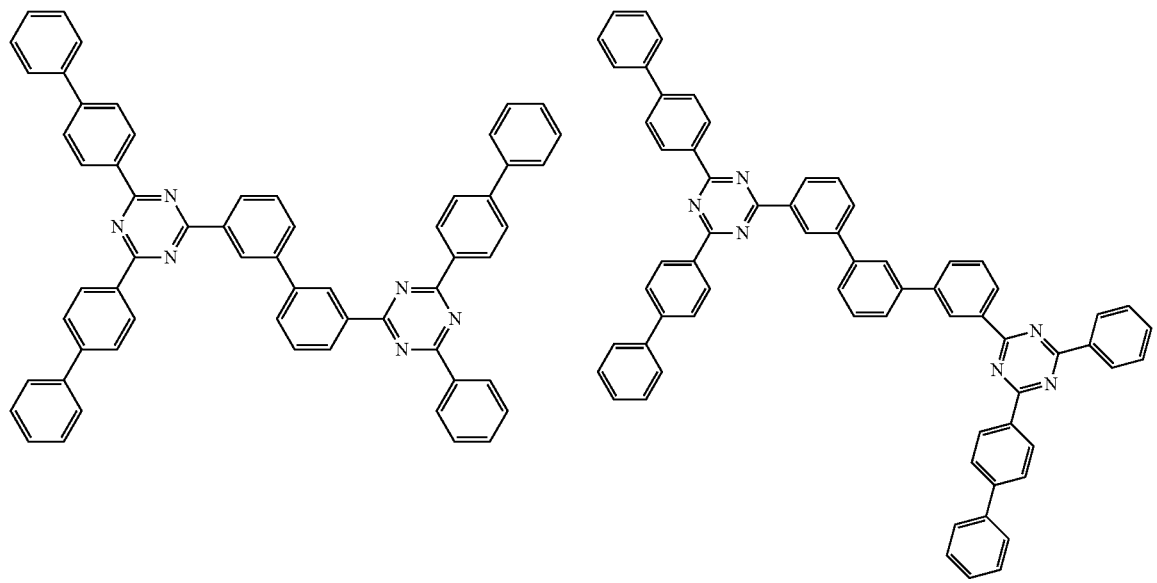
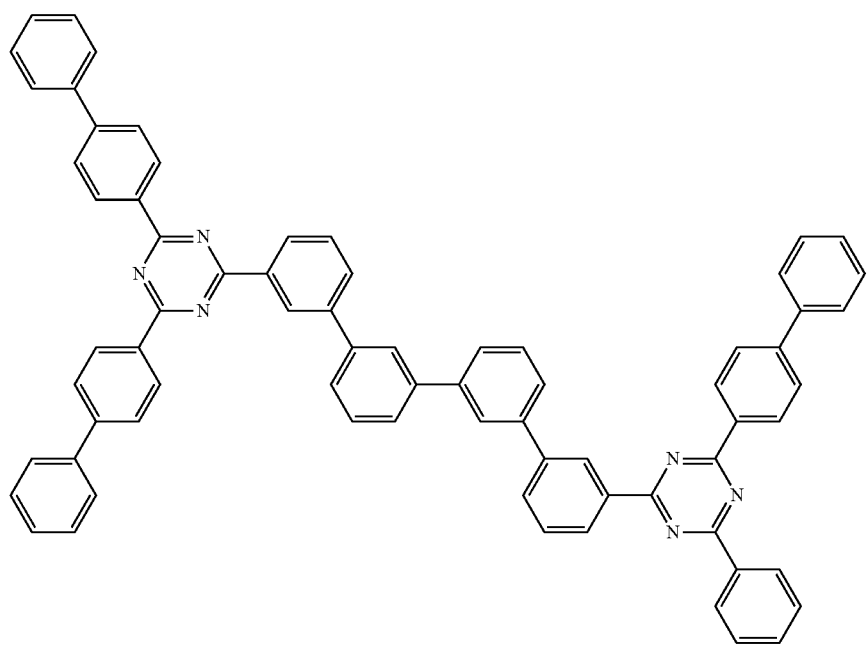

-continued
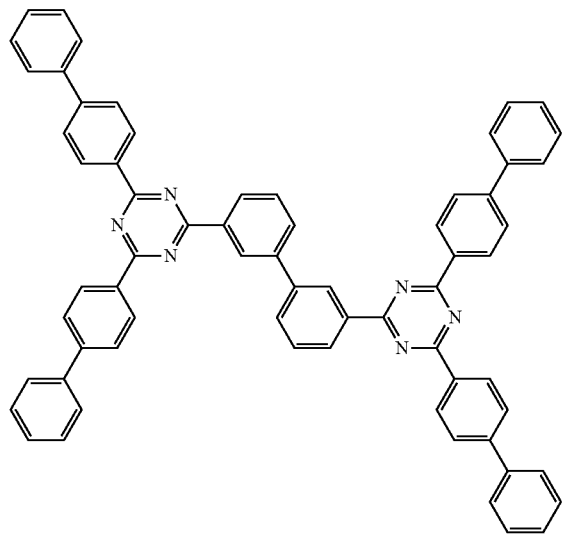
13
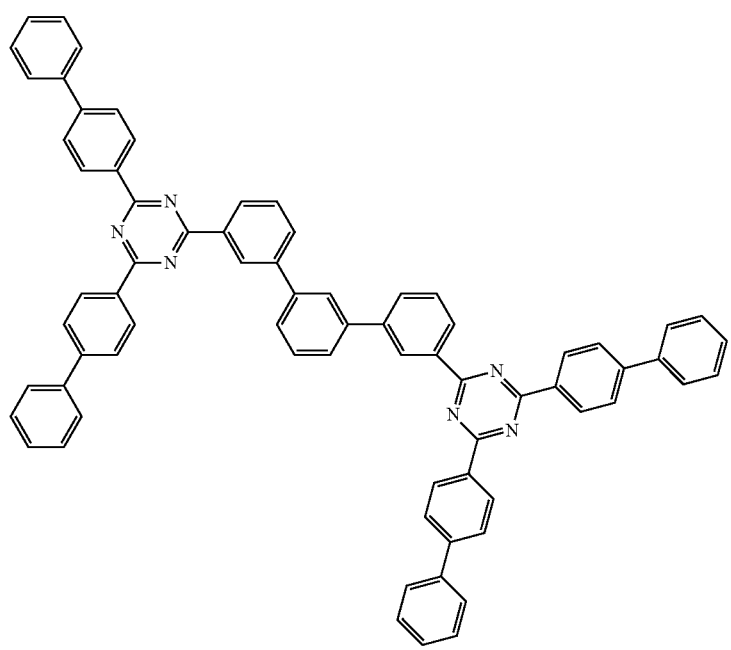
14

15
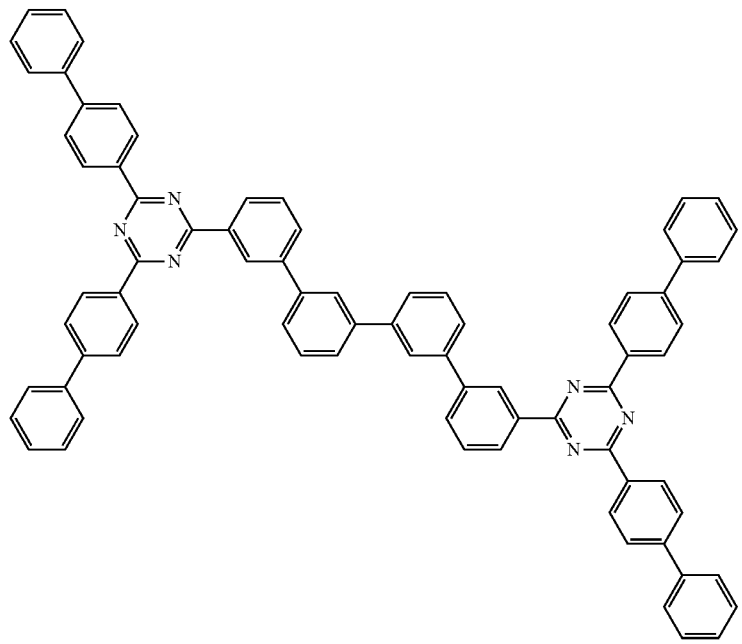
16
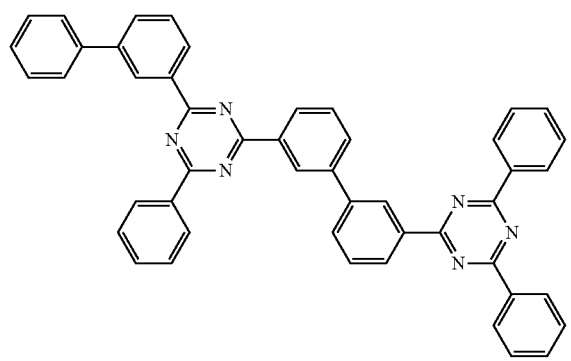
17
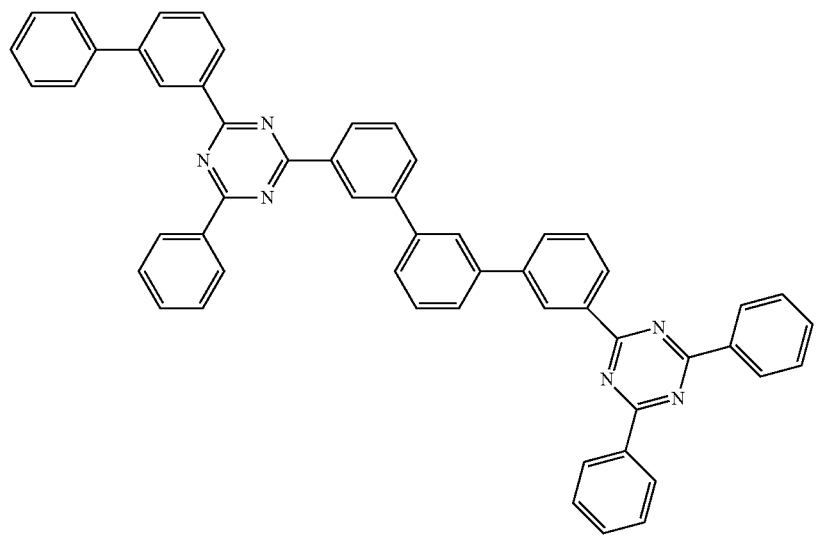

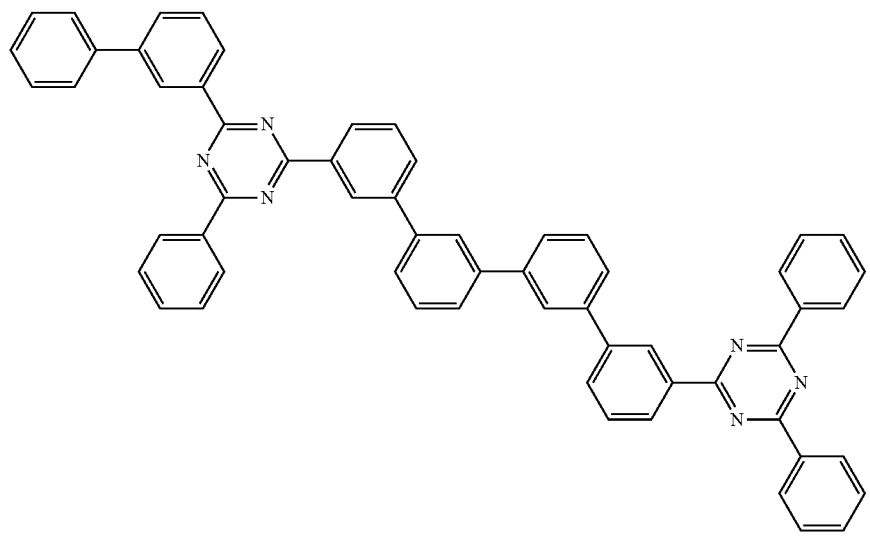
18
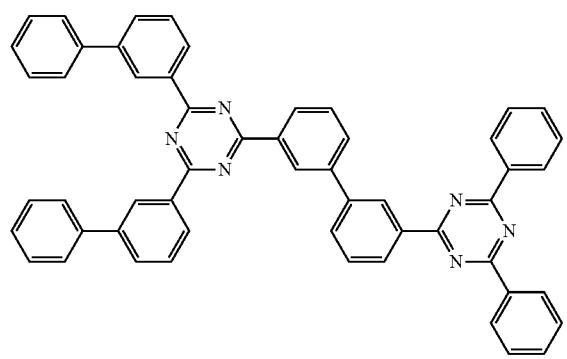
19
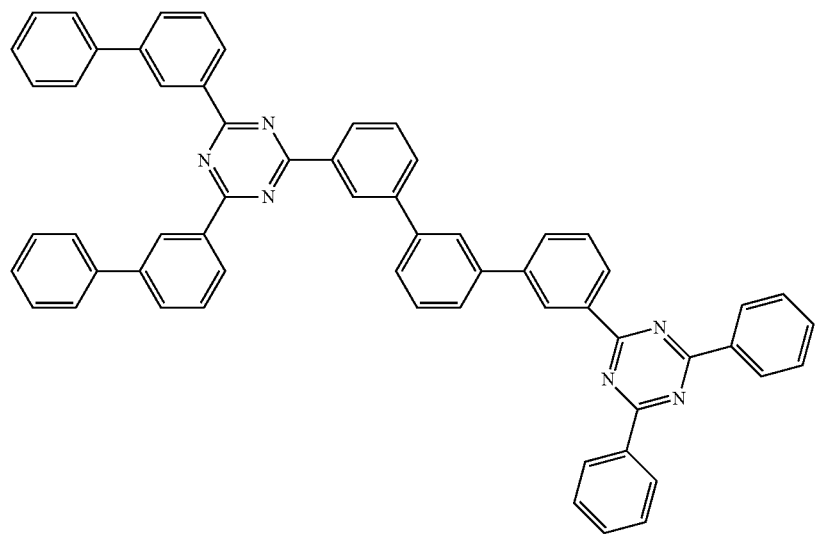
20

-continued
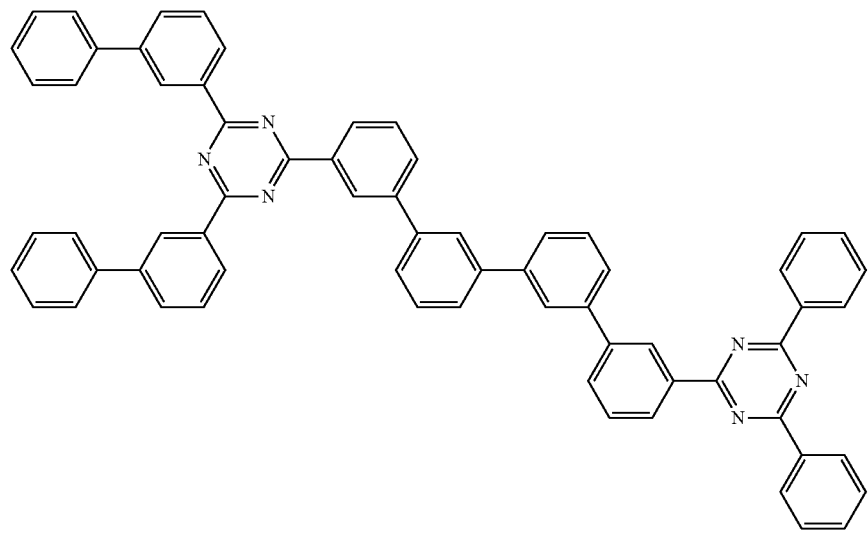
21
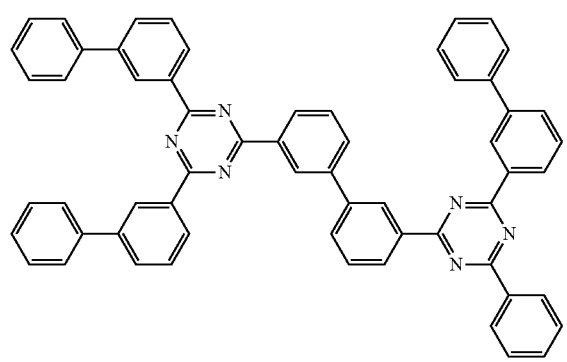
22
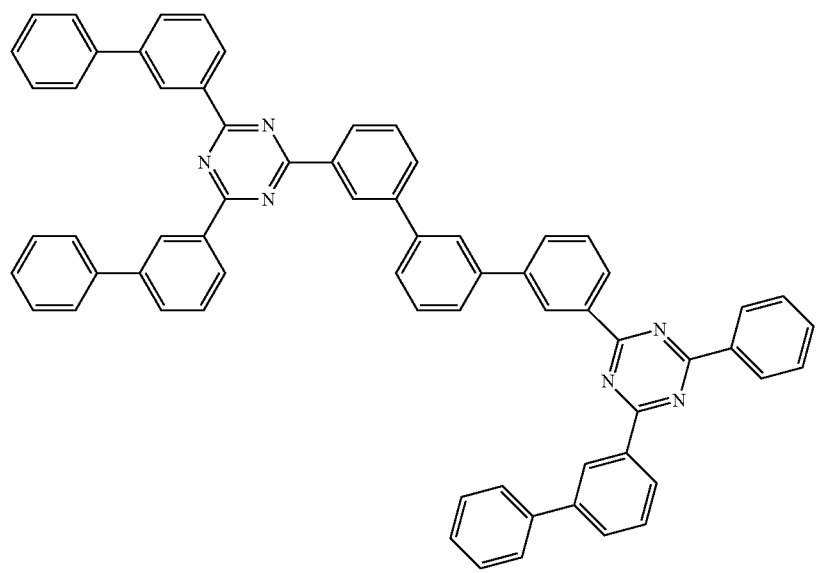
23

24
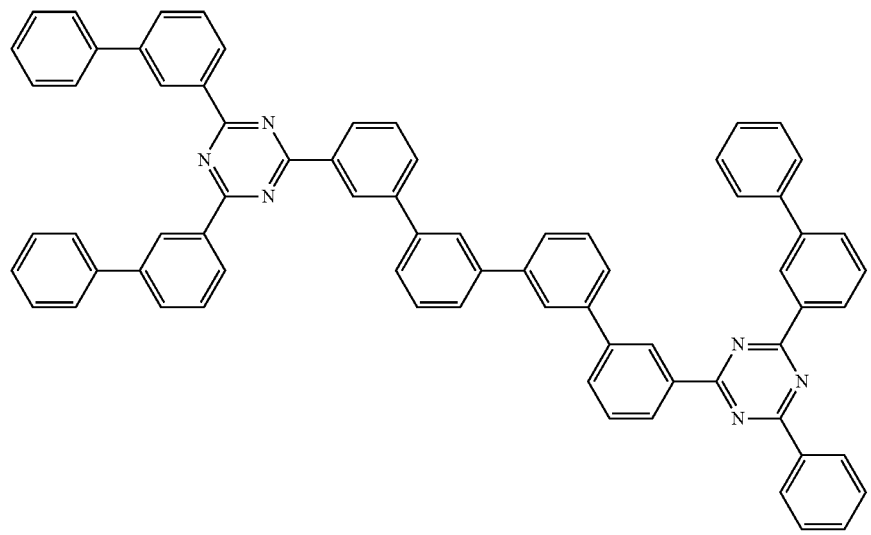
25
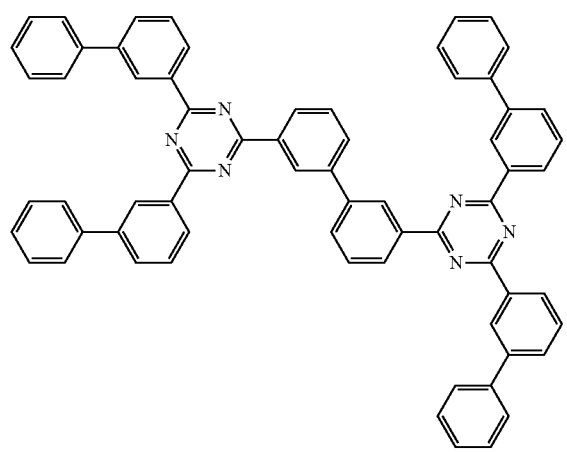
26
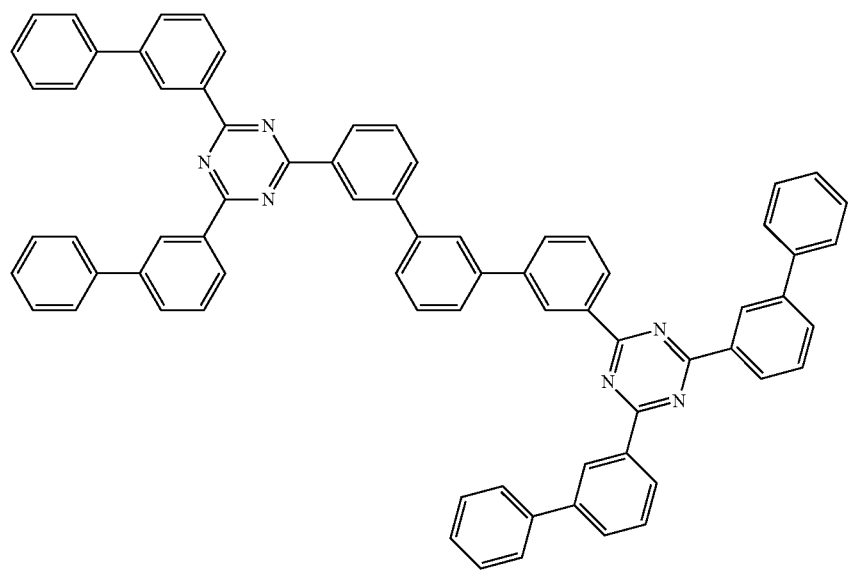

27
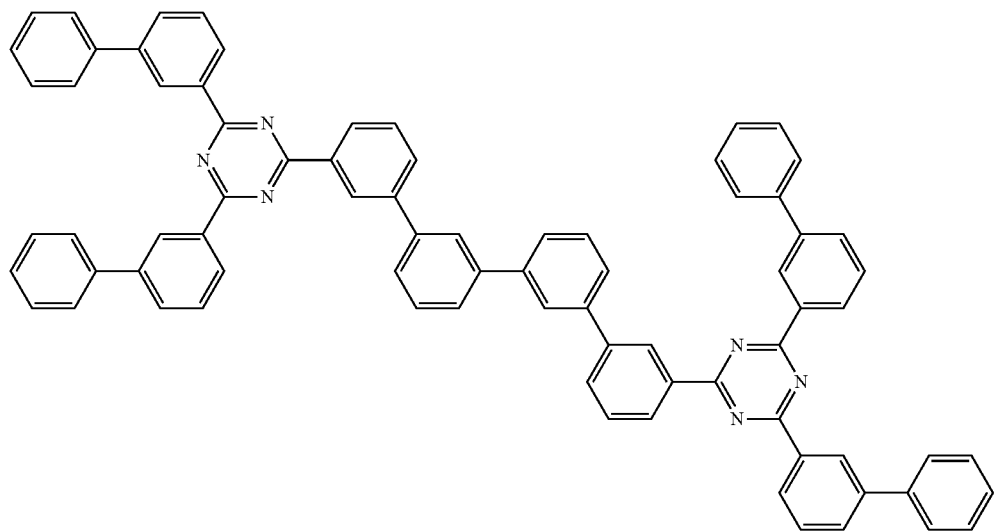
28
29
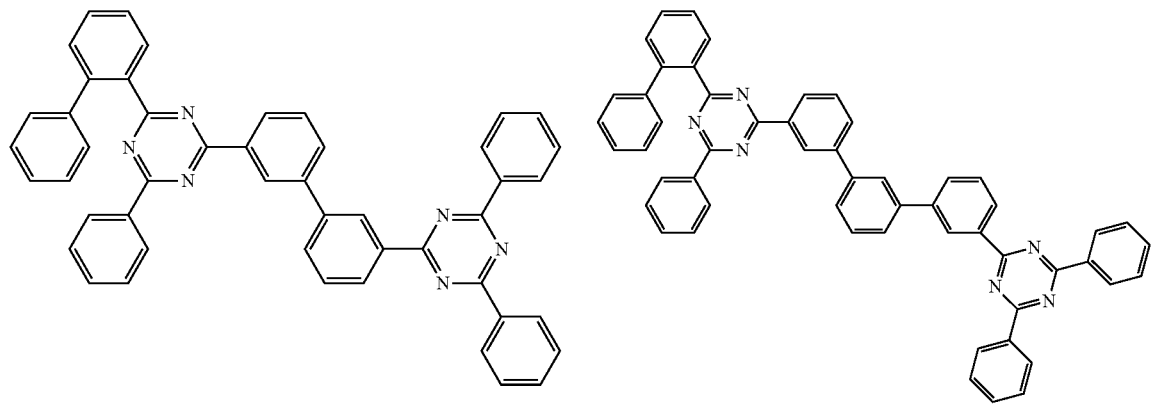
30
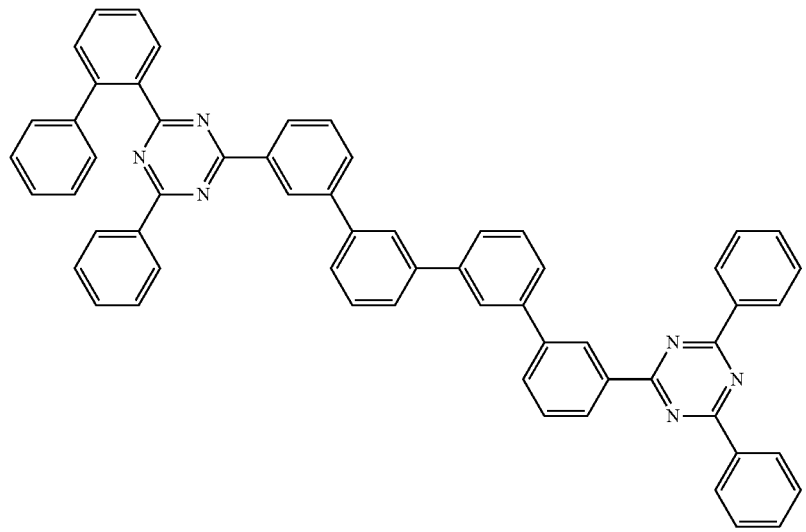

-continued
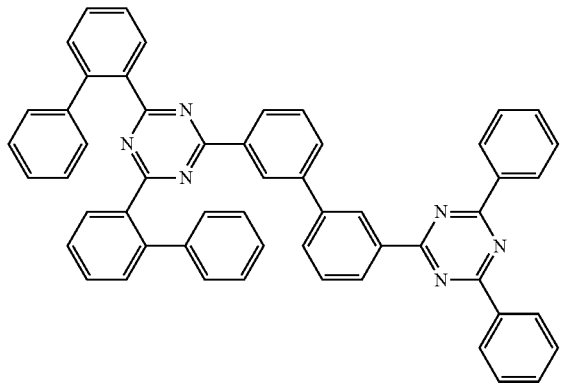
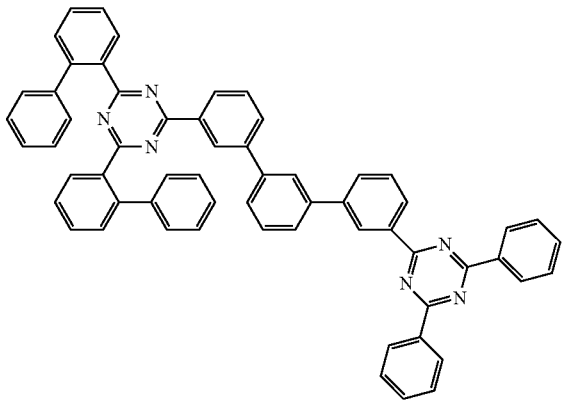
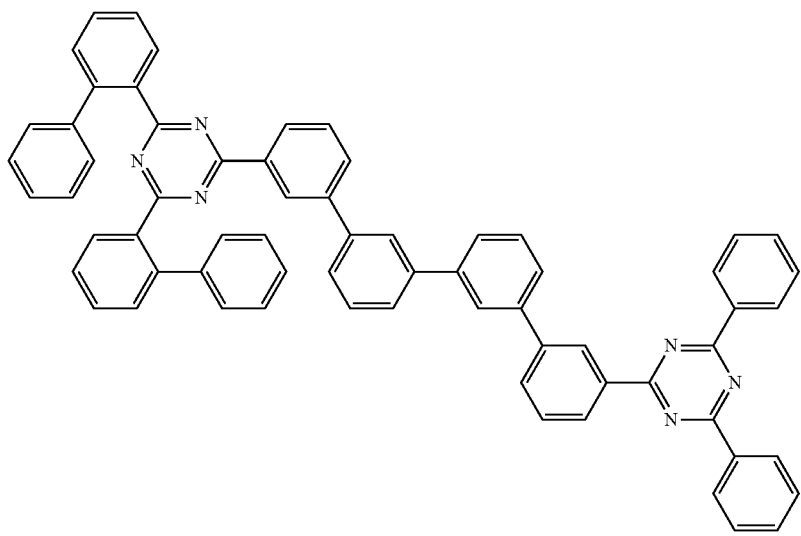
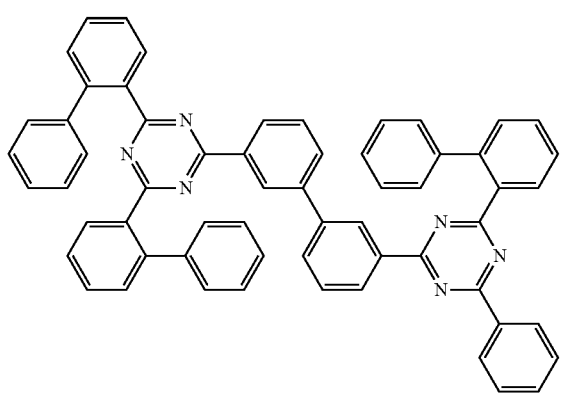
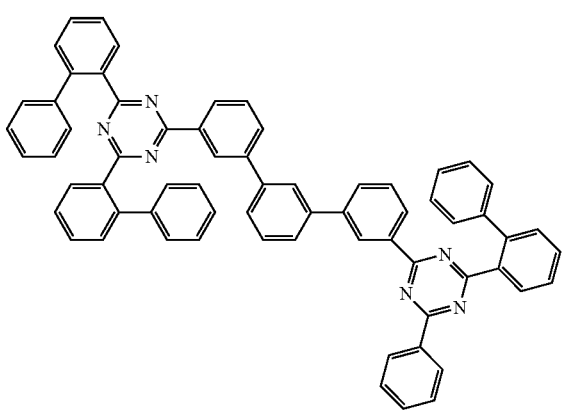

36
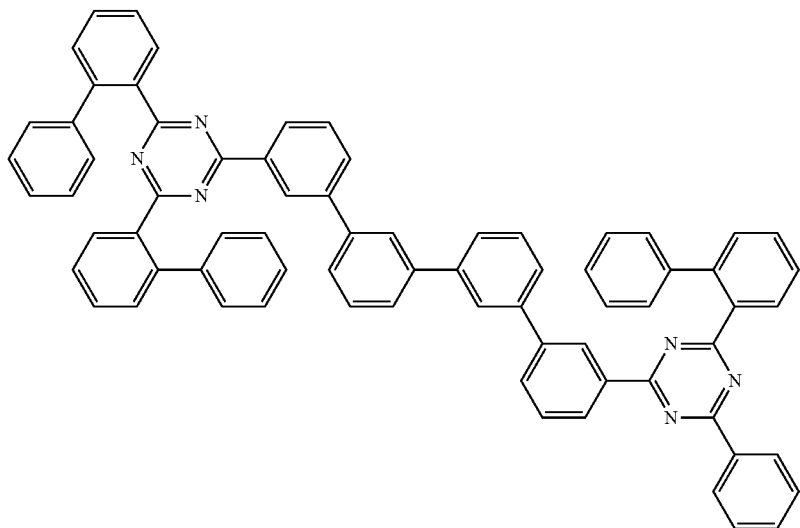
37 38
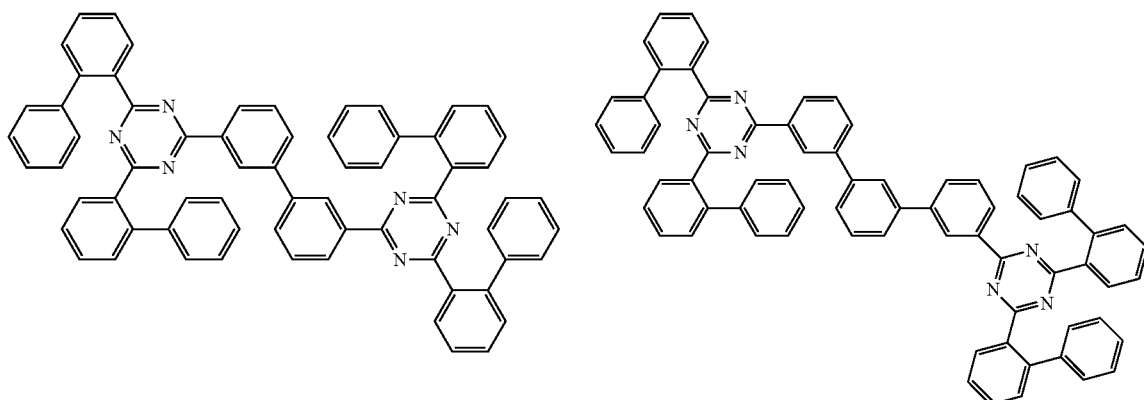
39
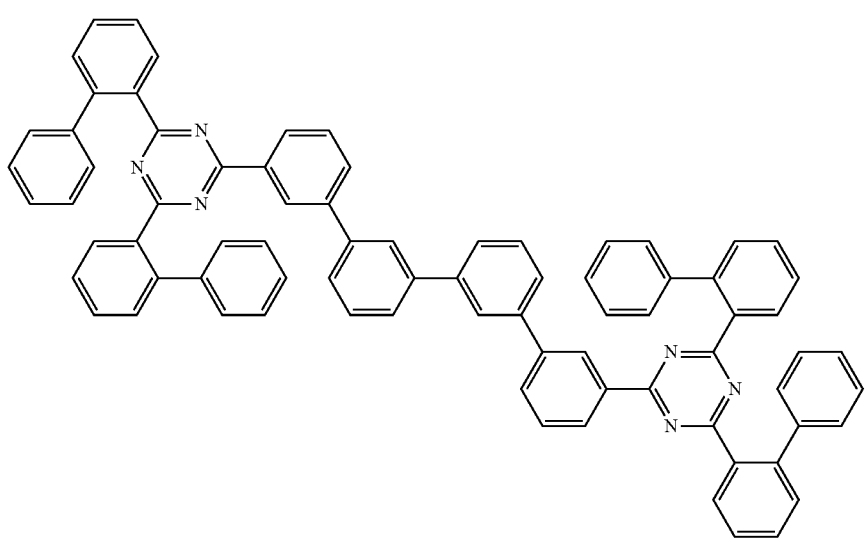

40
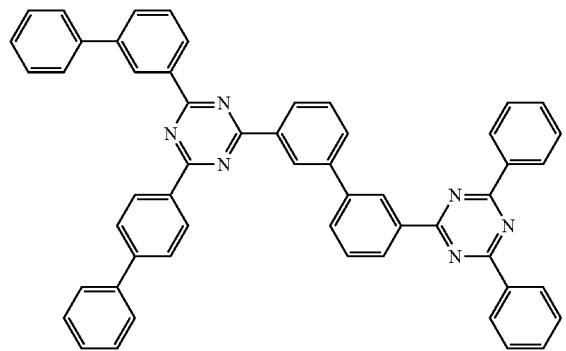
41
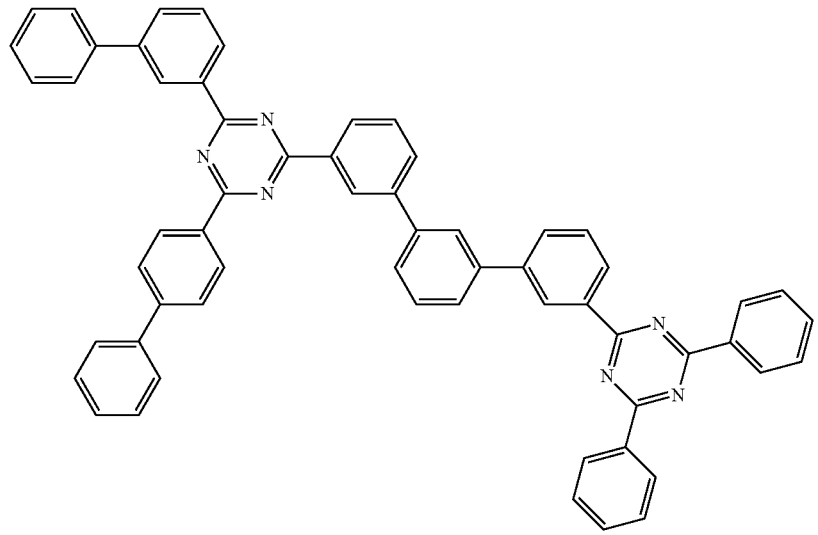
42
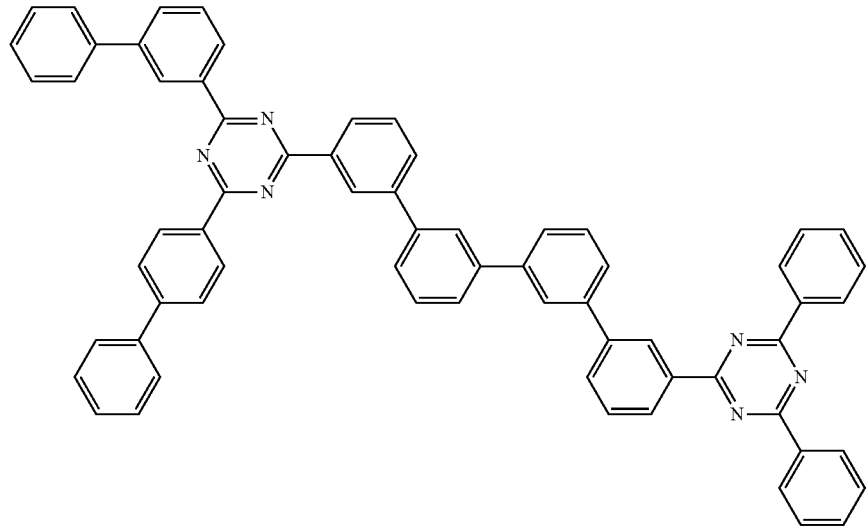

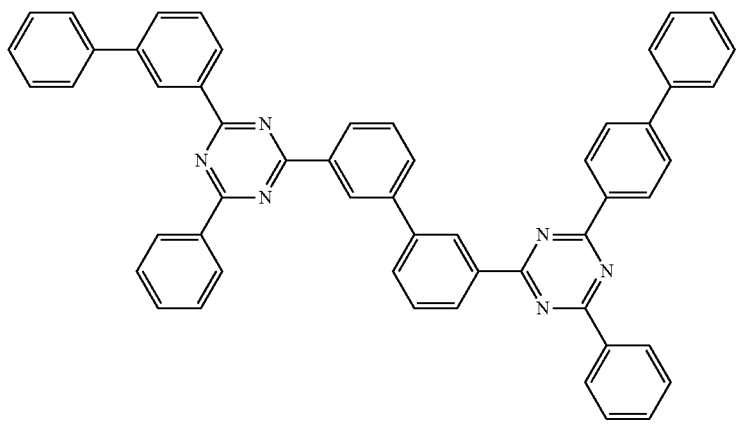
43
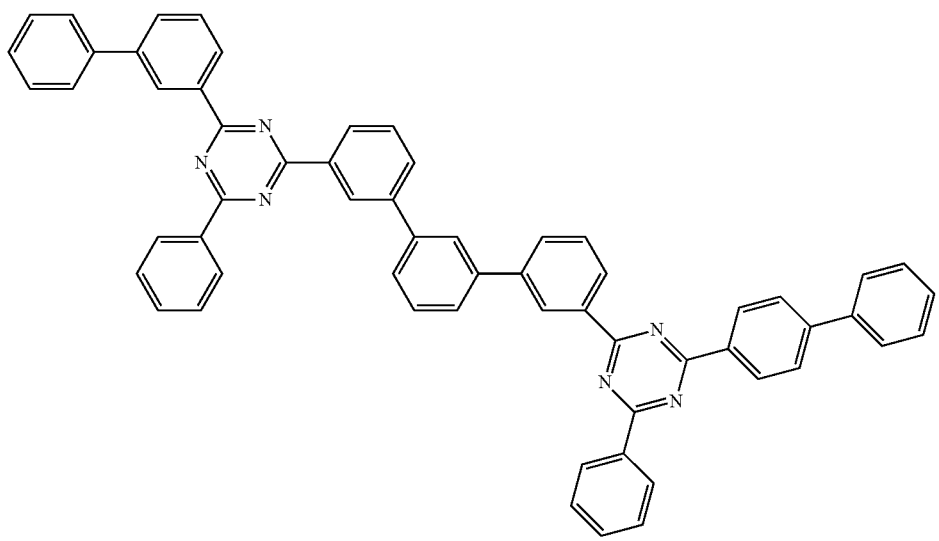
44
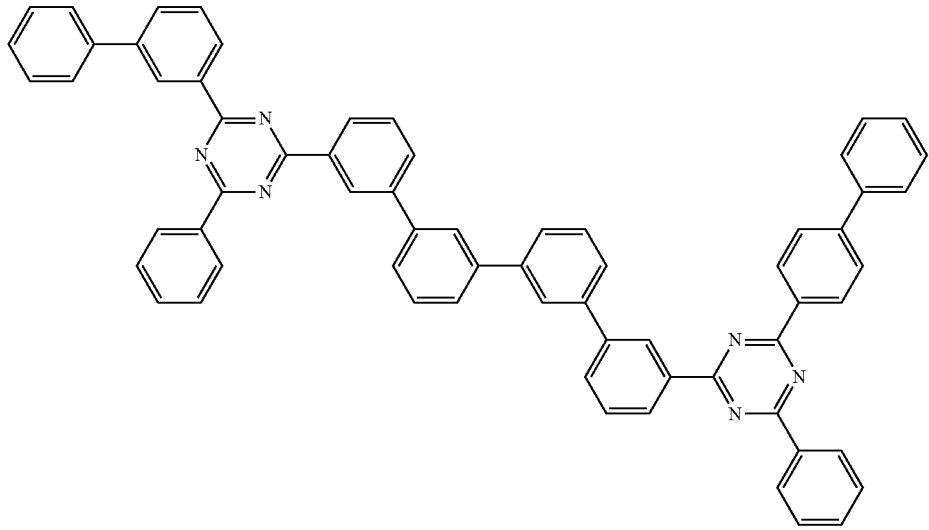
45

46
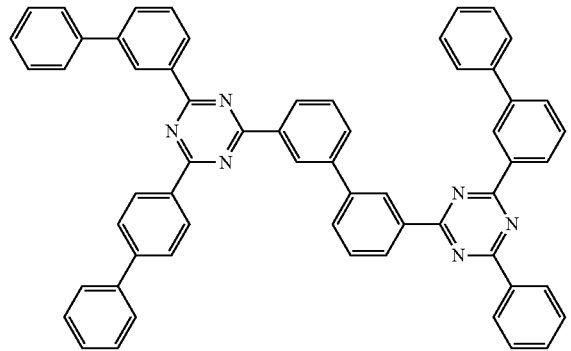
47
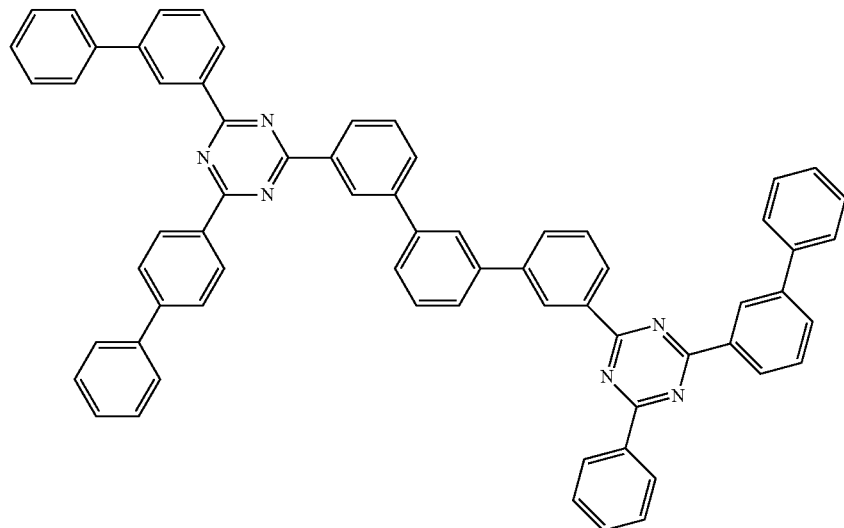
48
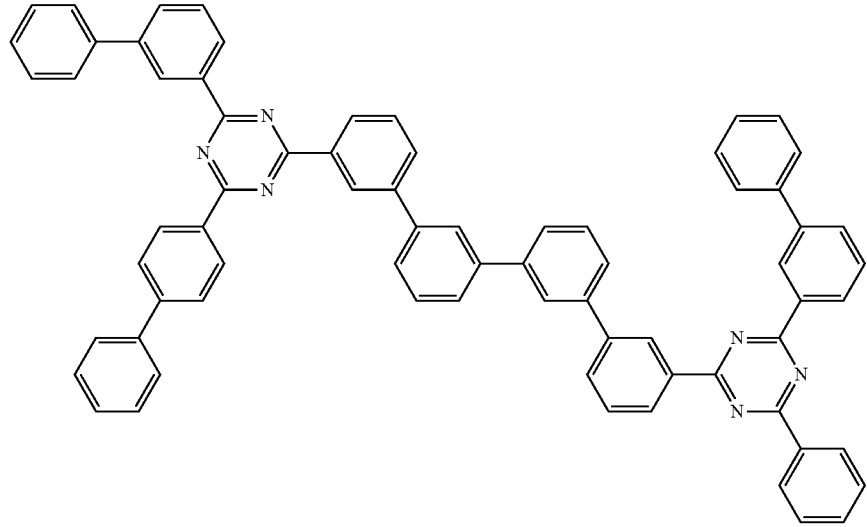

49
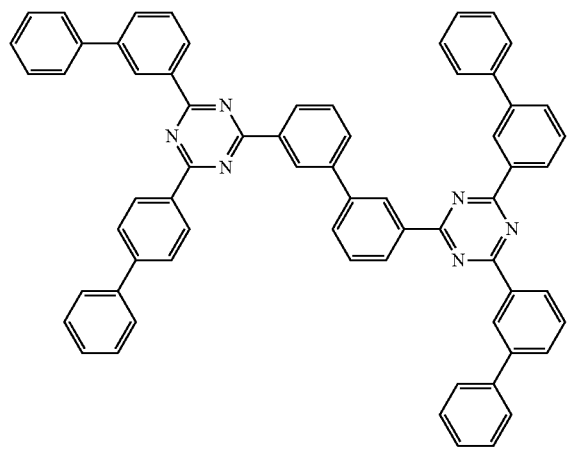
50
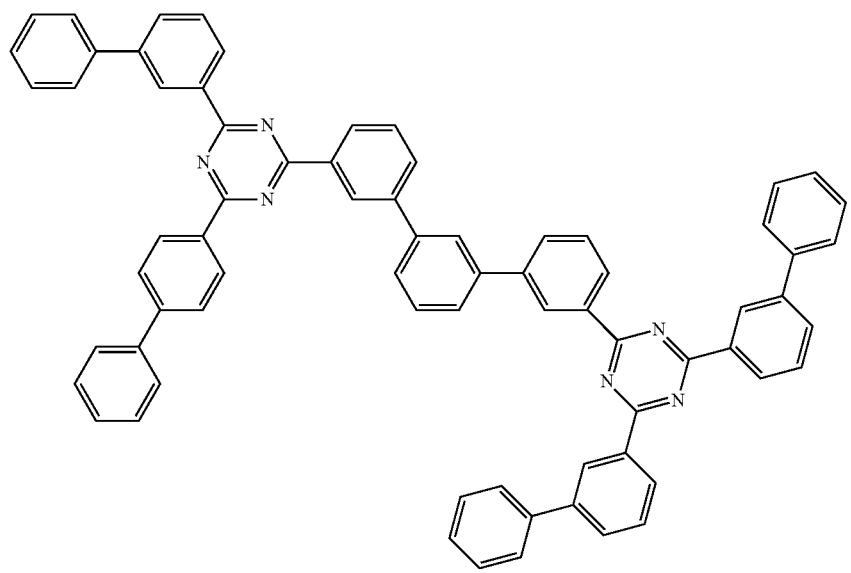
51
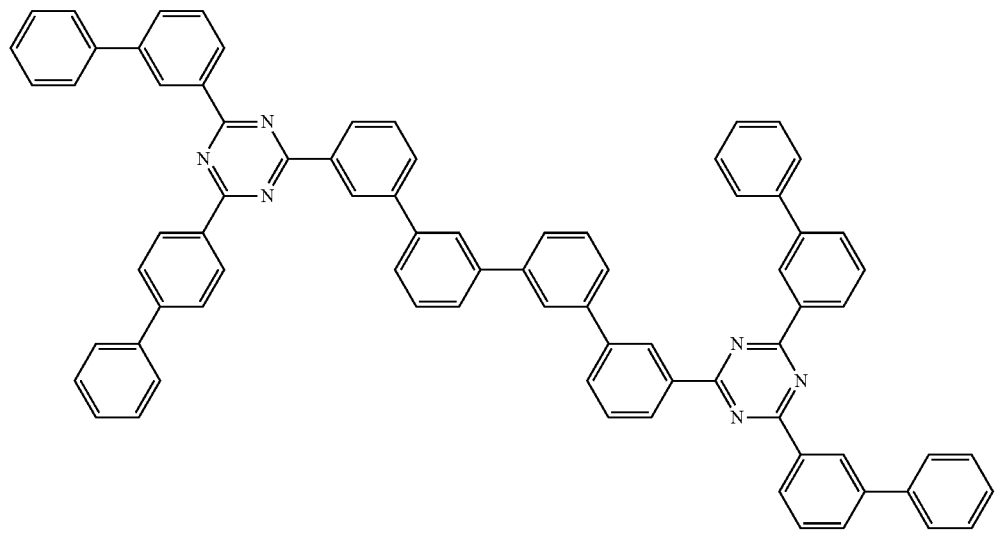

-continued
52
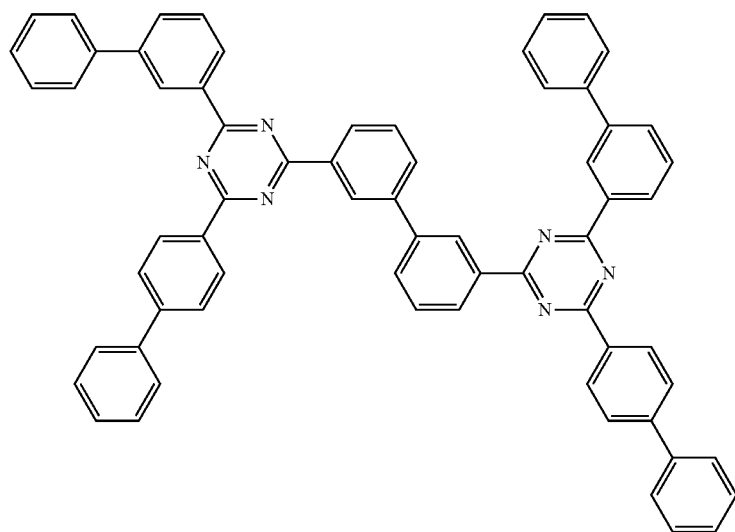
53
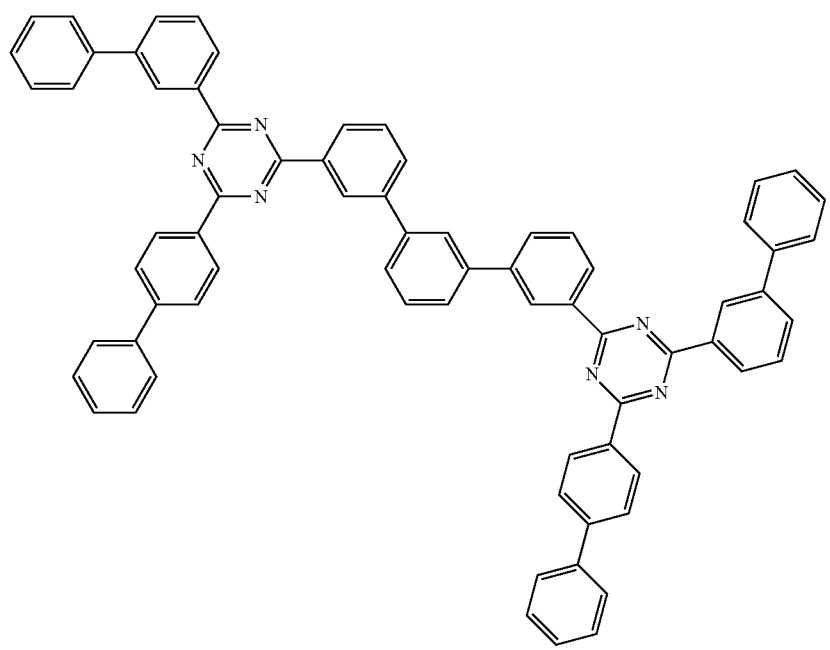

-continued
54
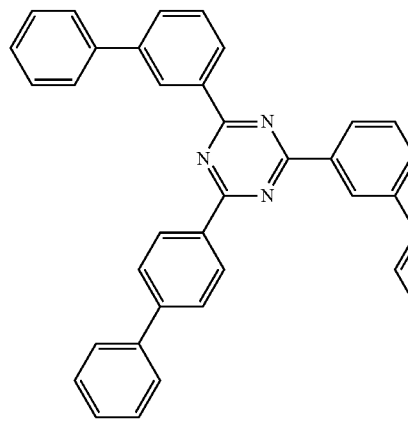
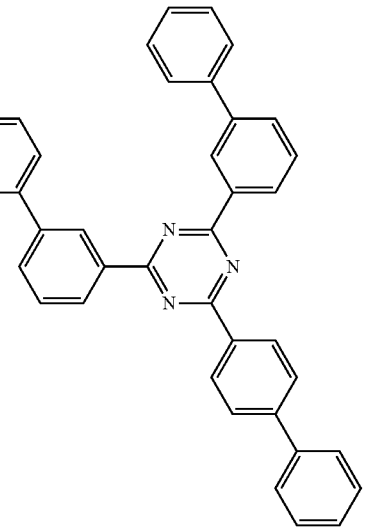
55
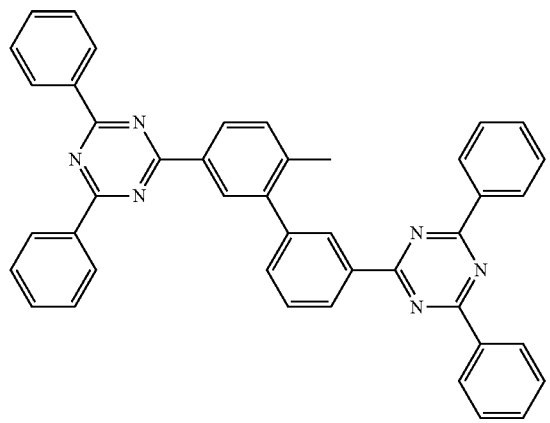
56
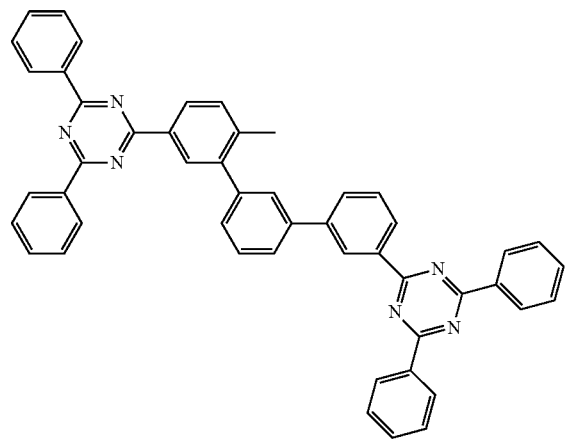
57
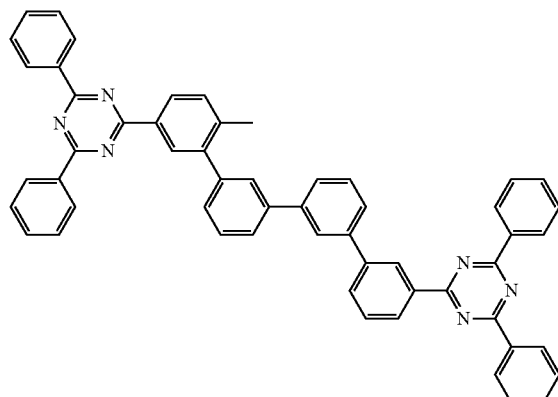
58
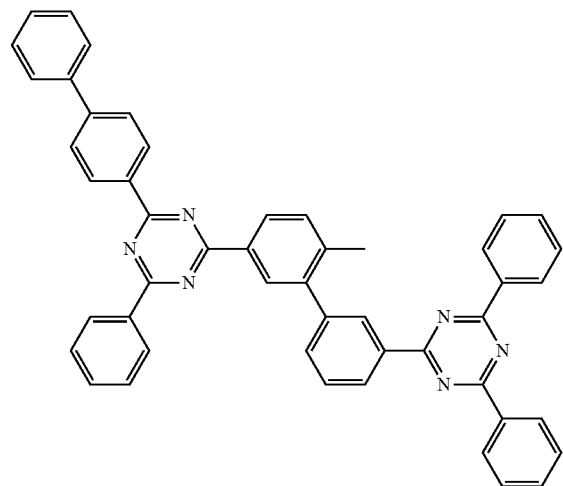

-continued
59
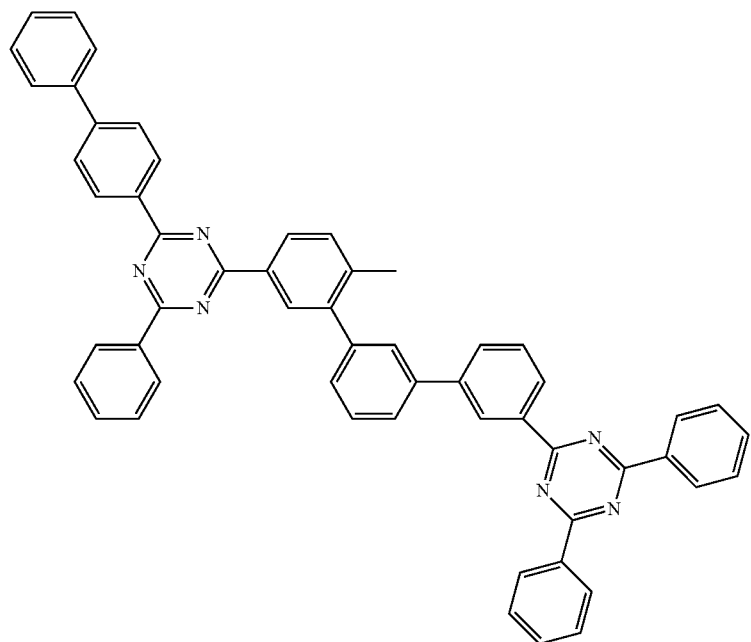
60
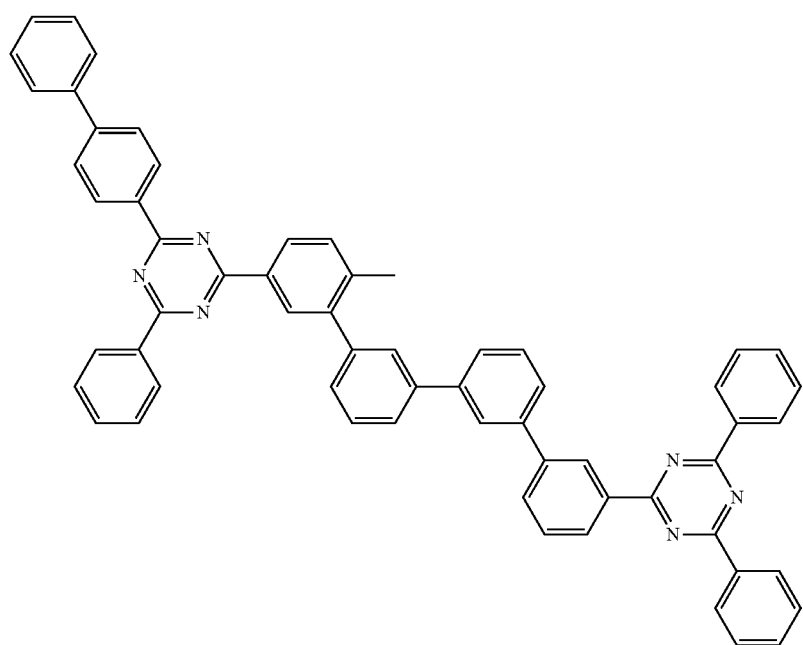
61
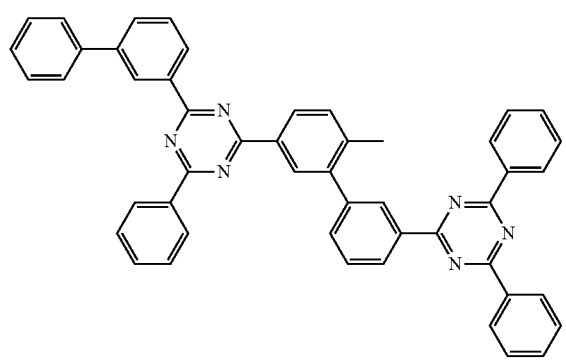

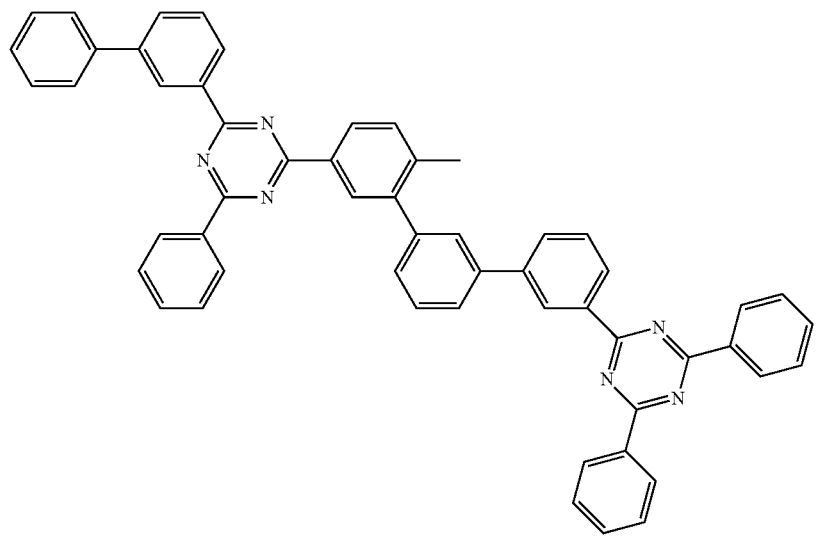
62
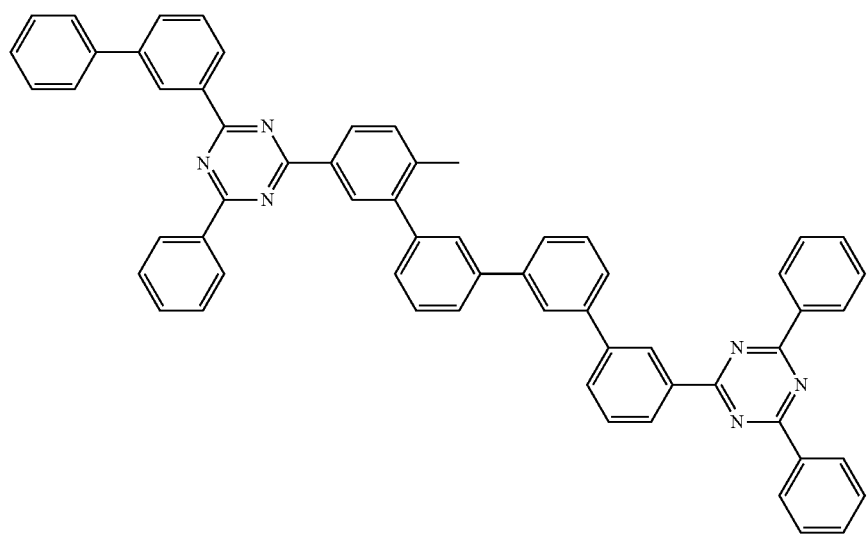
63
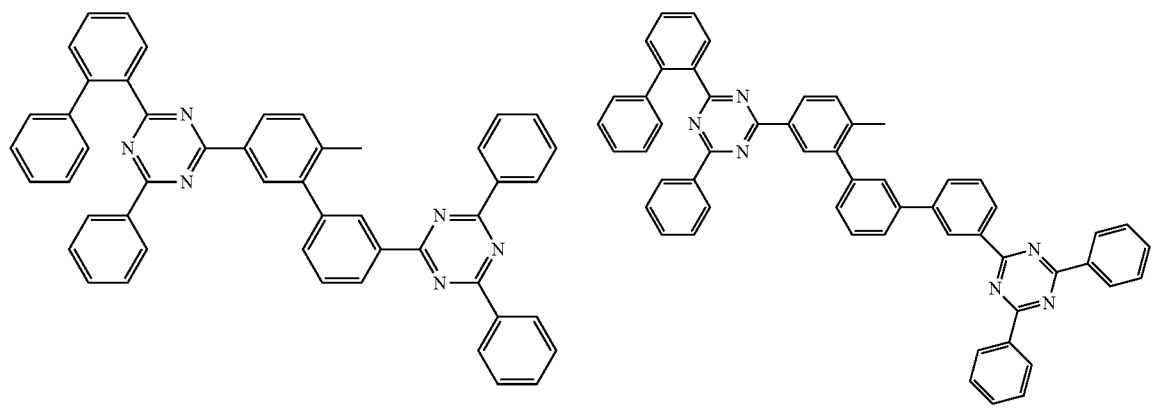
64 65

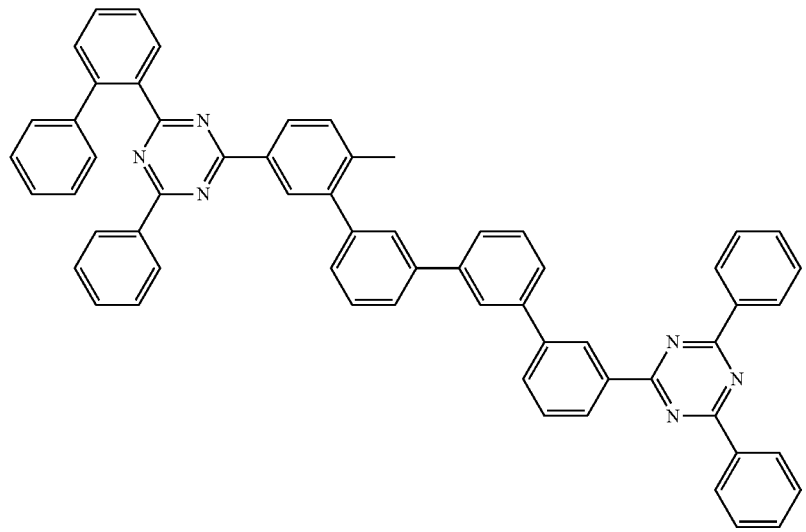
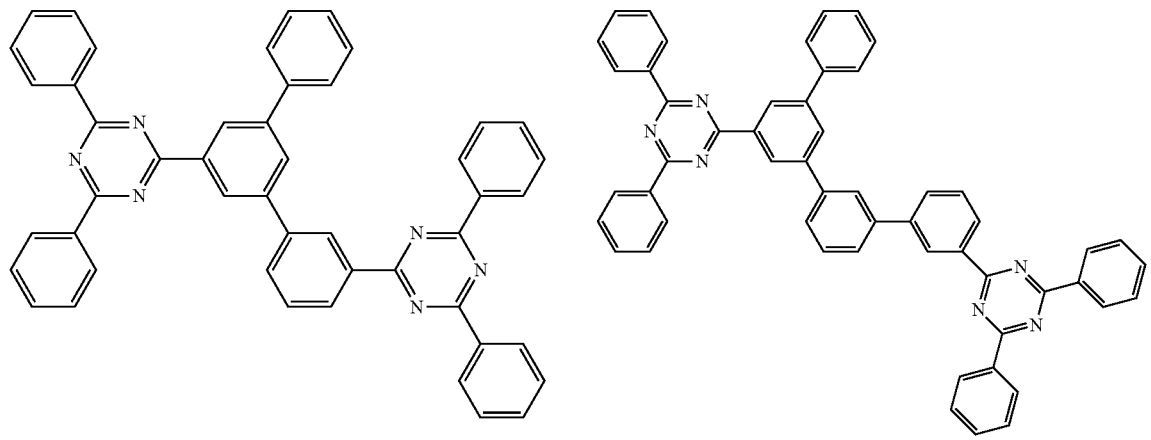
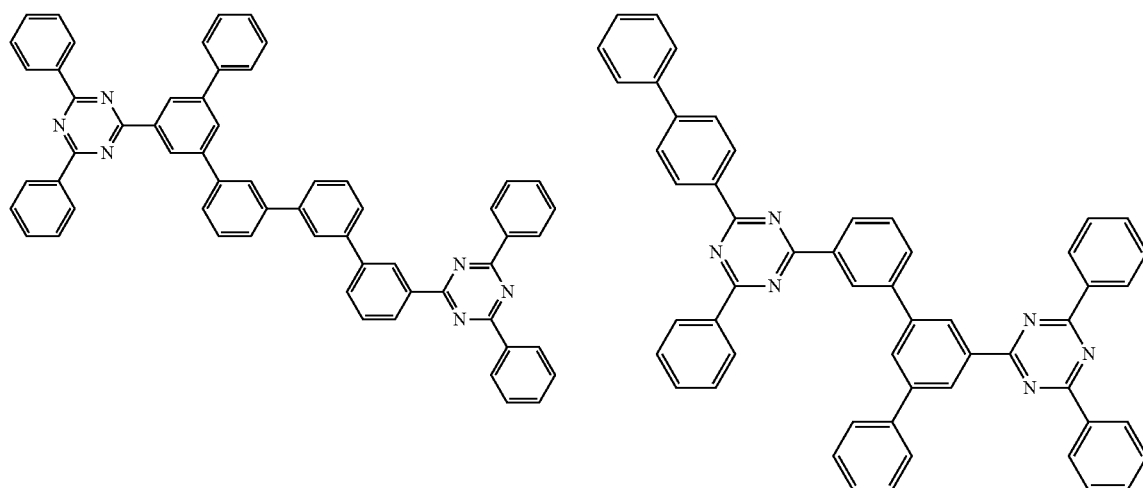

-continued
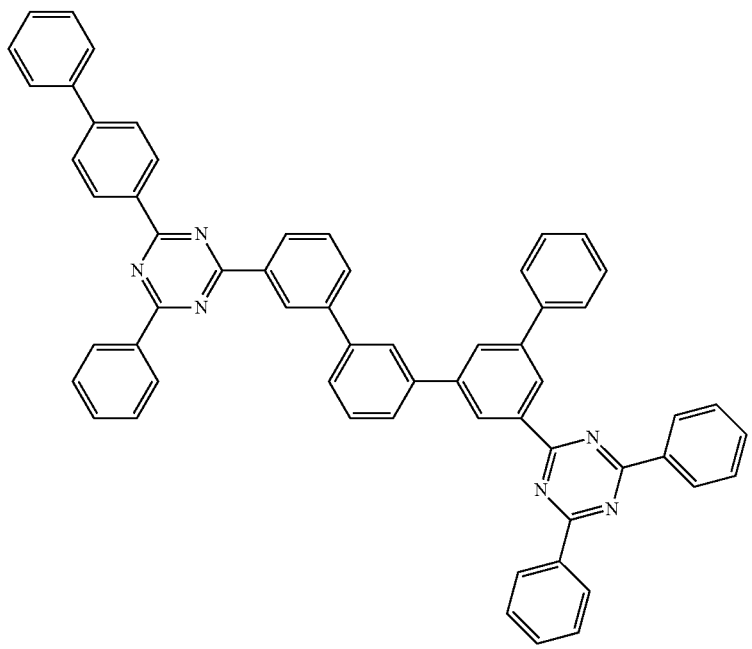
71
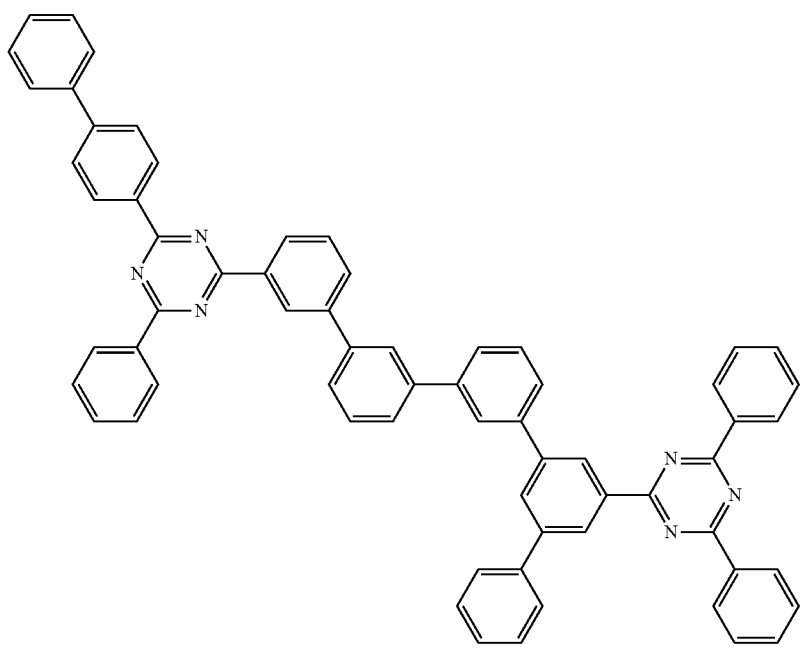
72
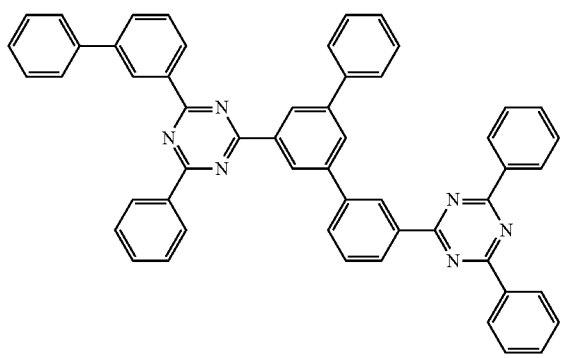
73

74
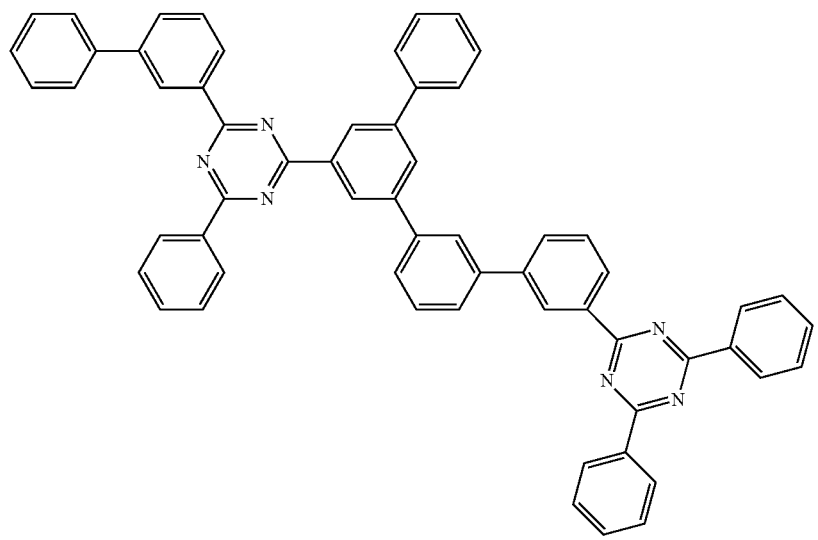
75
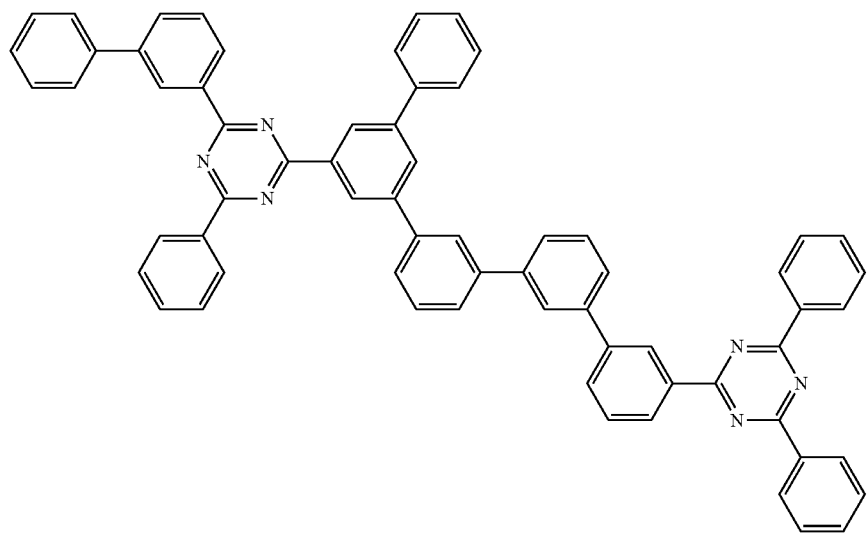
76 77
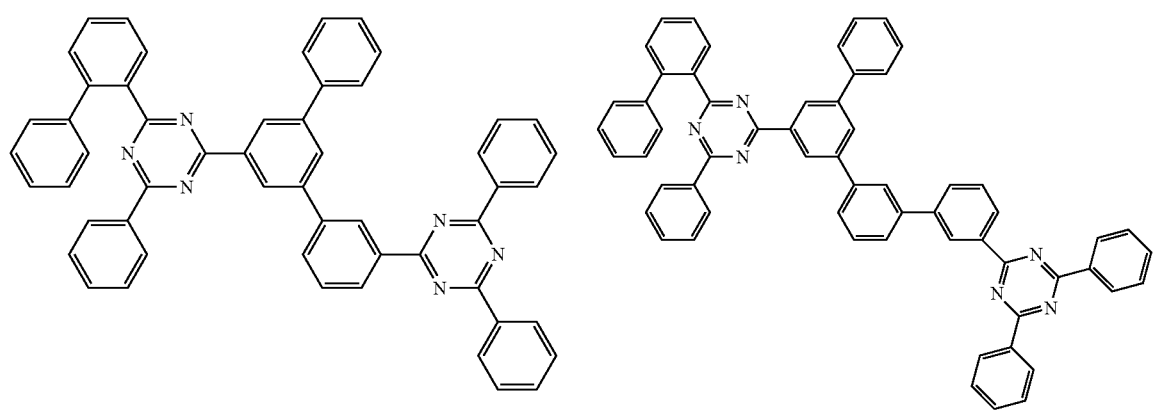

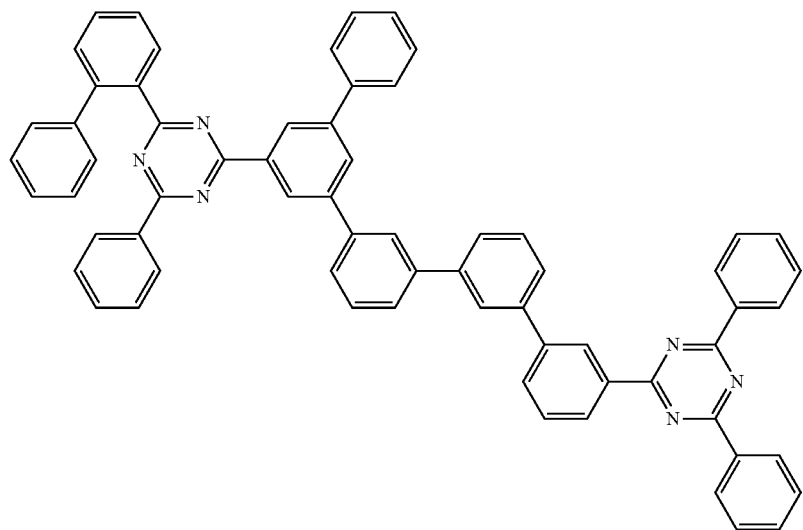
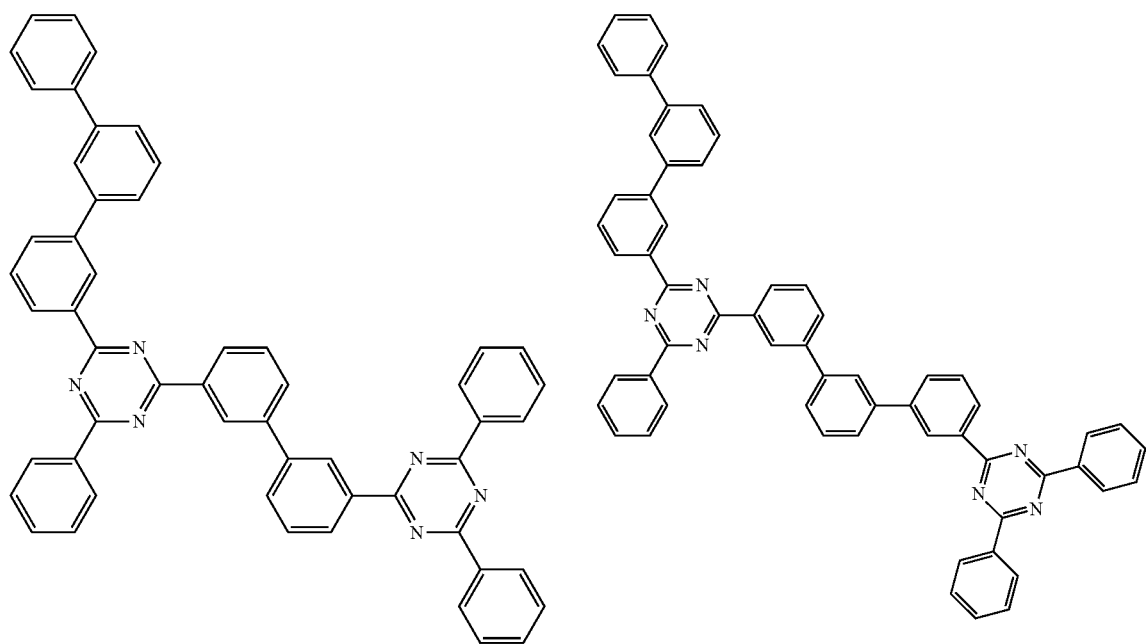

-continued
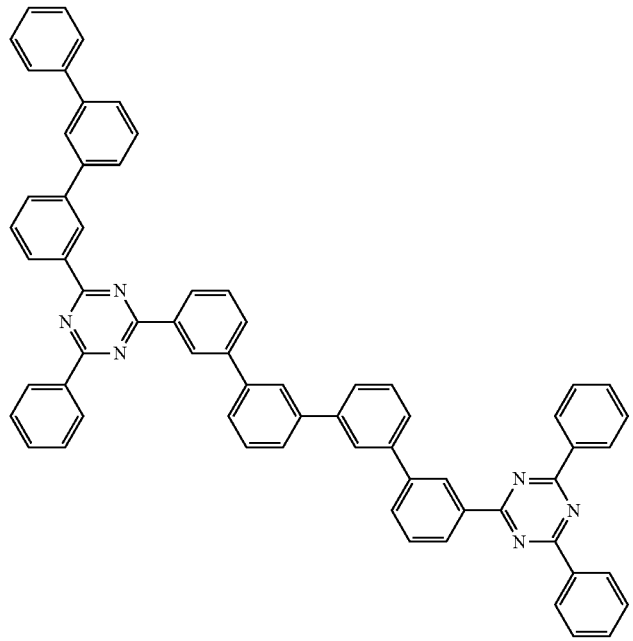
81
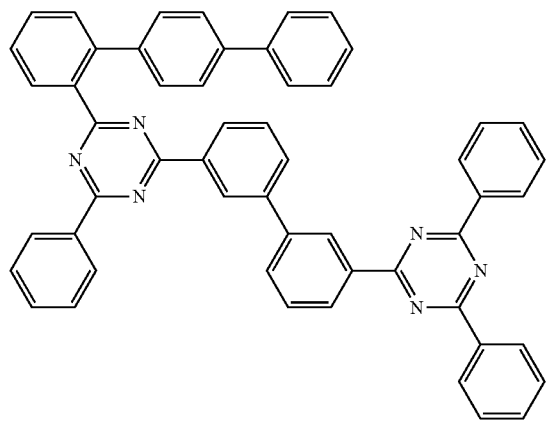
82
83

84
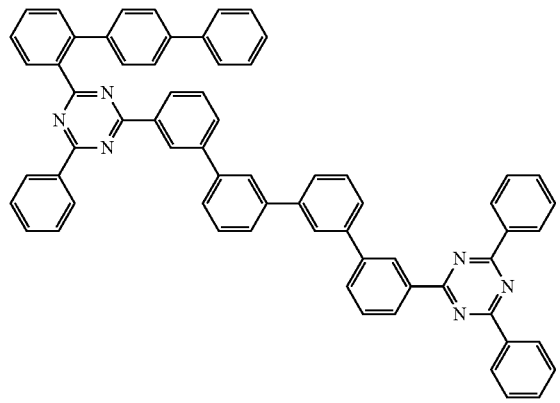
85
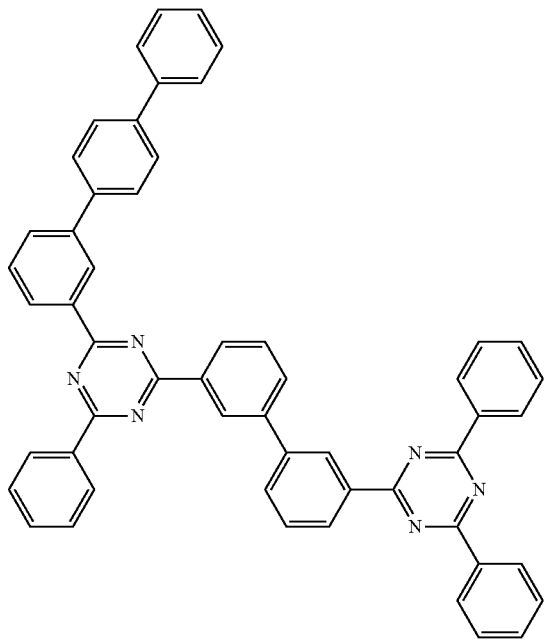
86
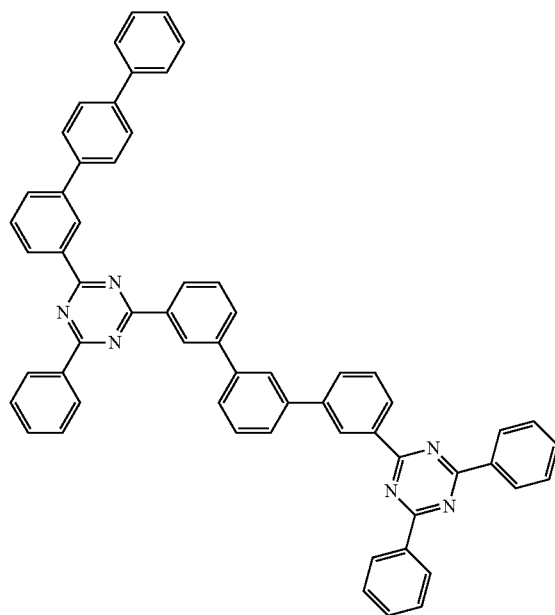
87
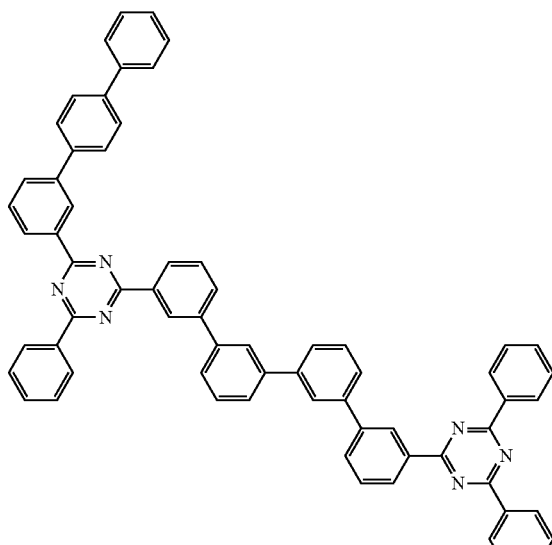

88
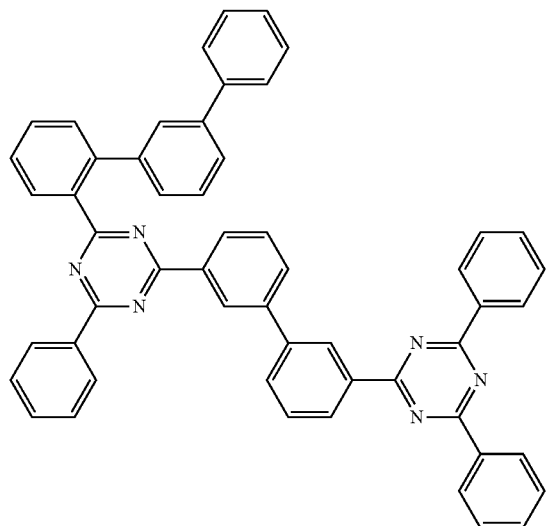
89
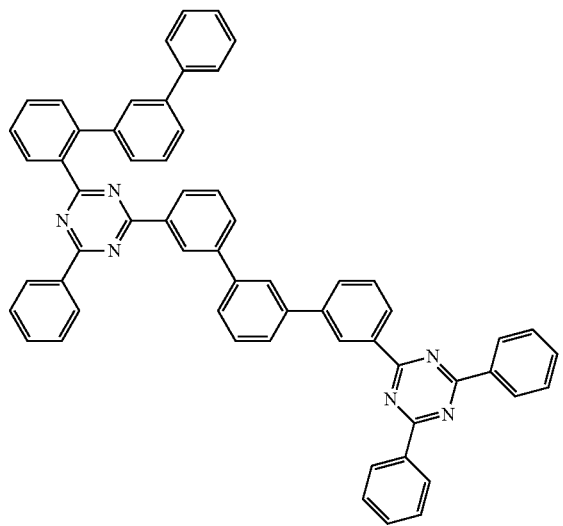
90
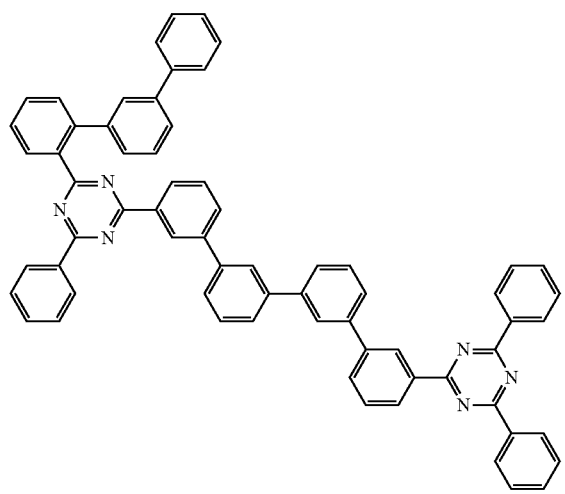
91
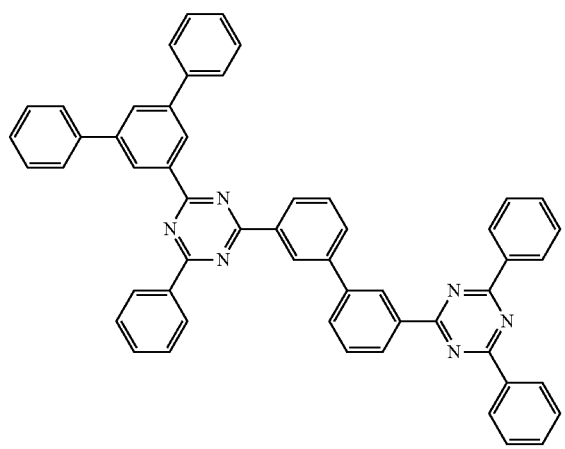

92
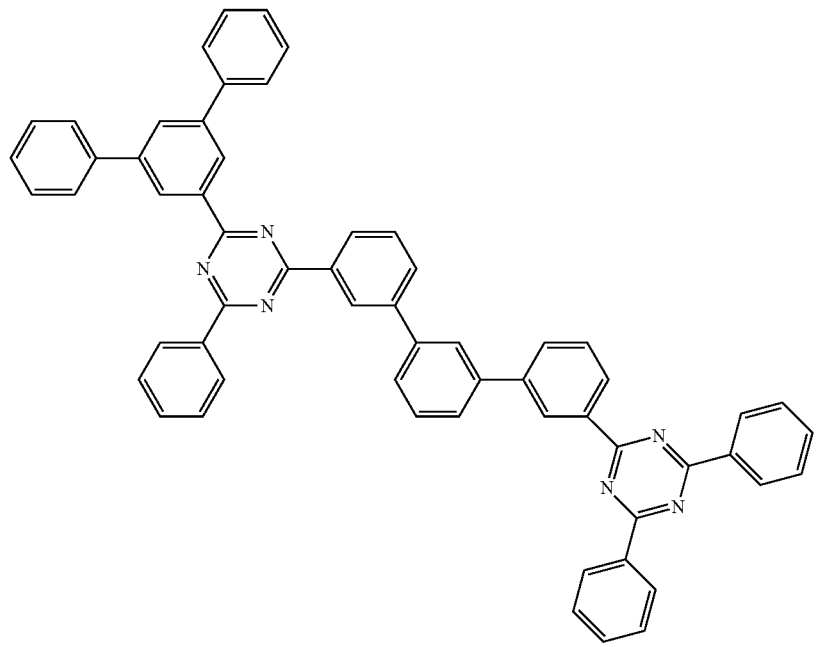
93
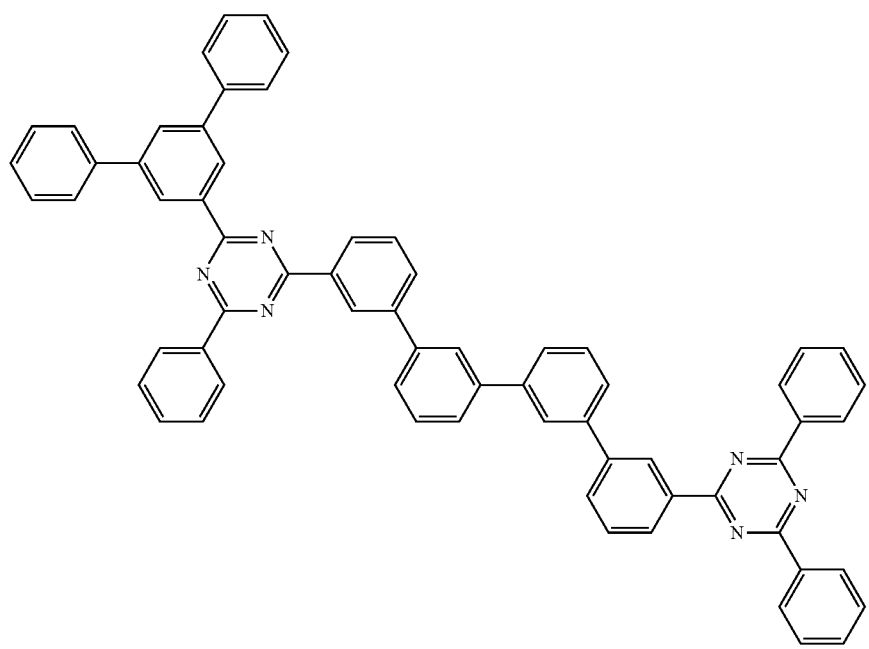

-continued
94
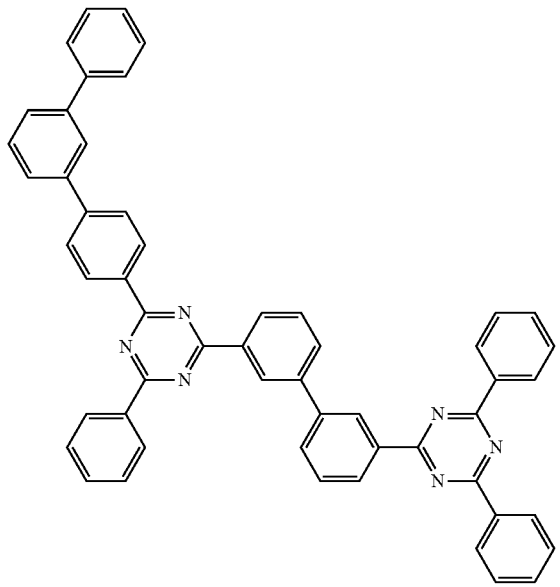
95
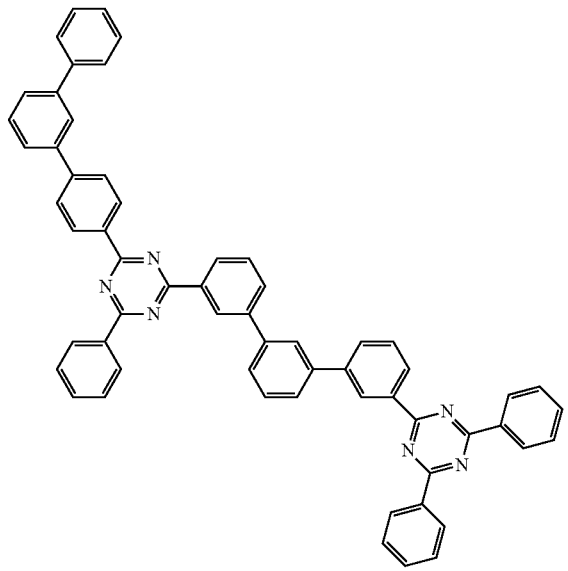
96
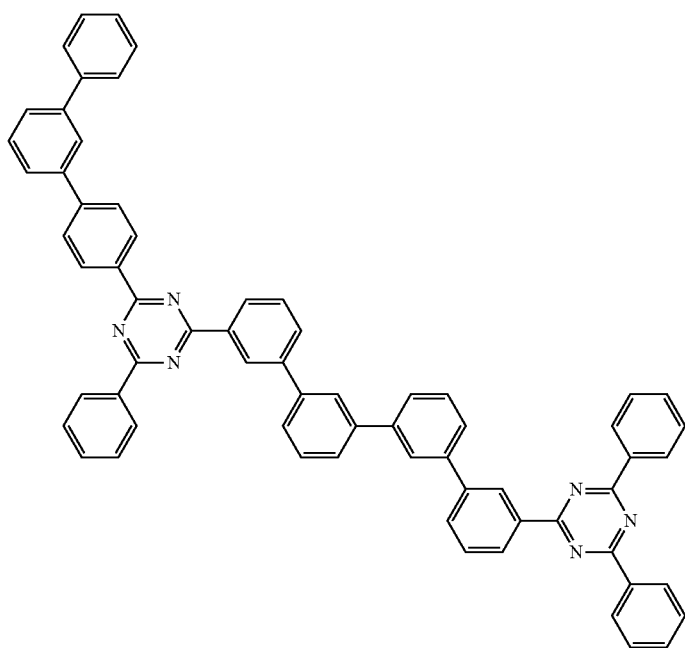

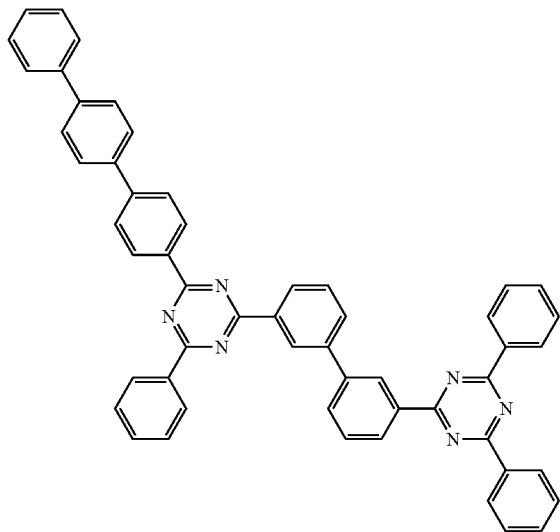
97
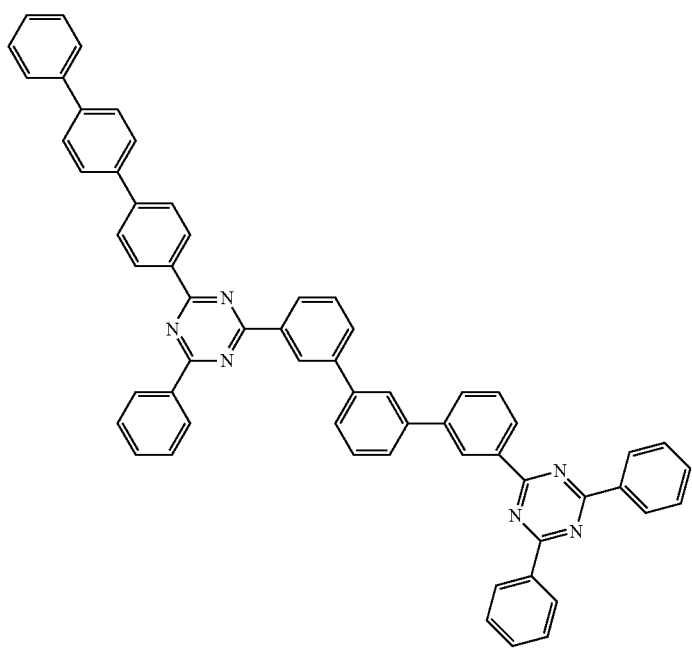
98

-continued
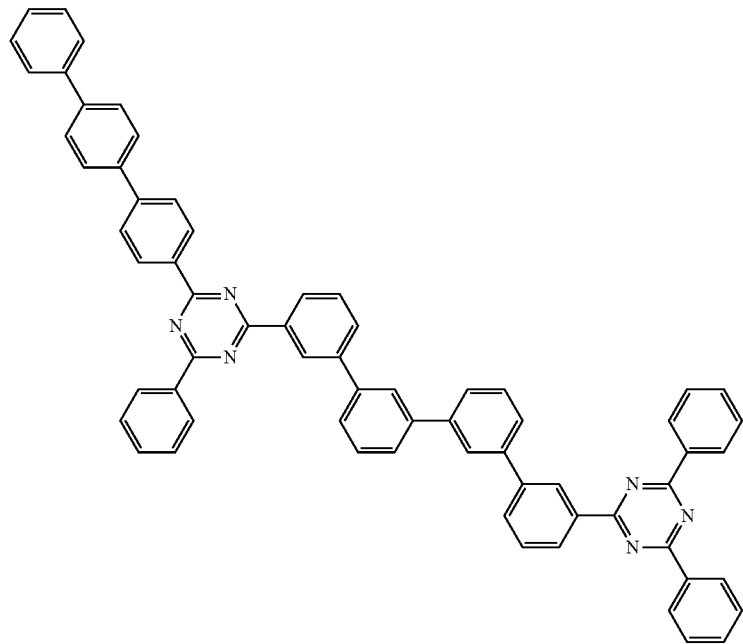
99
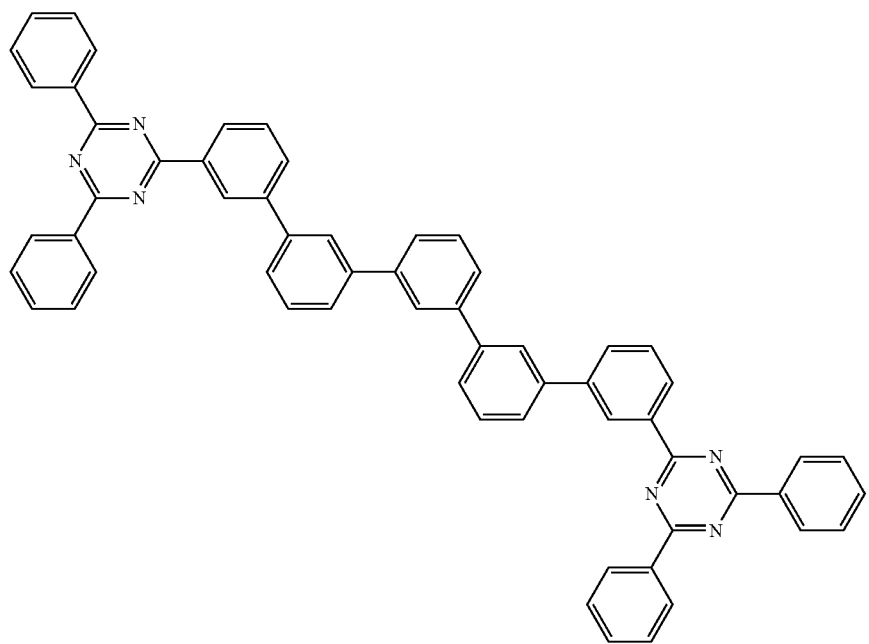
100

-continued
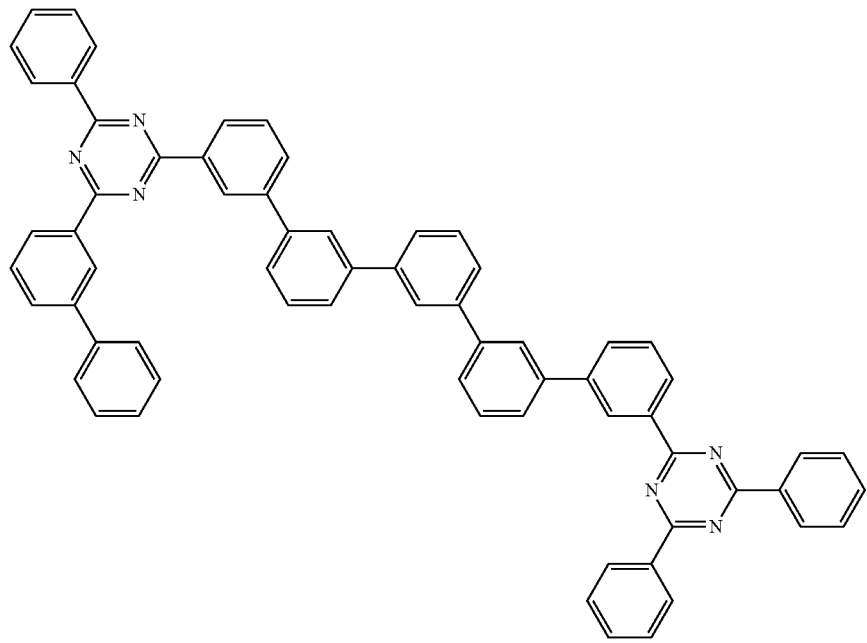
101
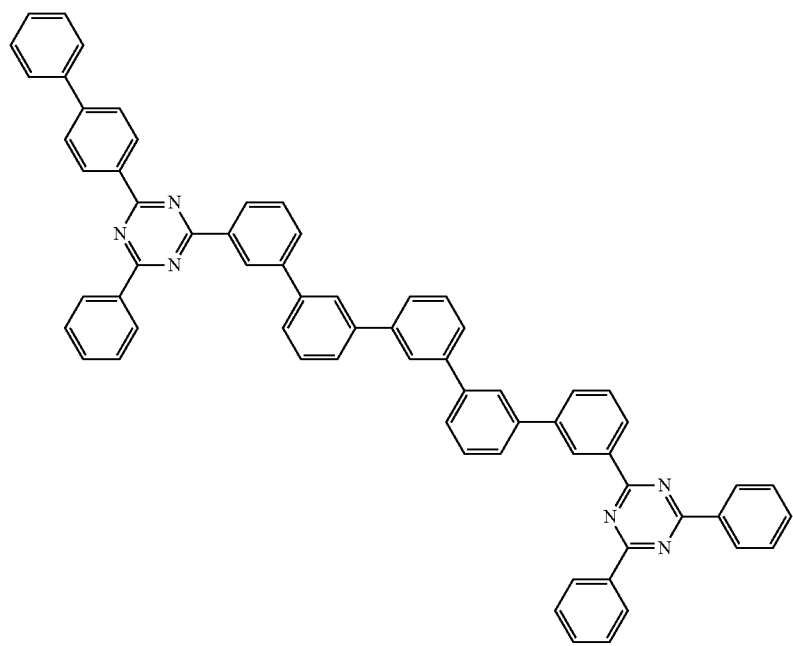
102

-continued
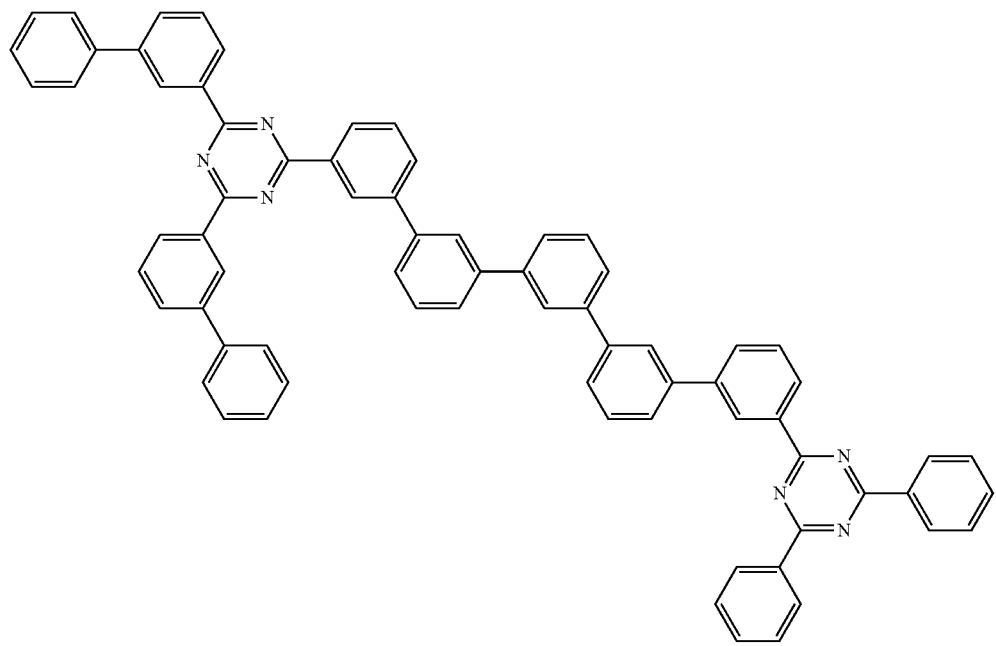
103
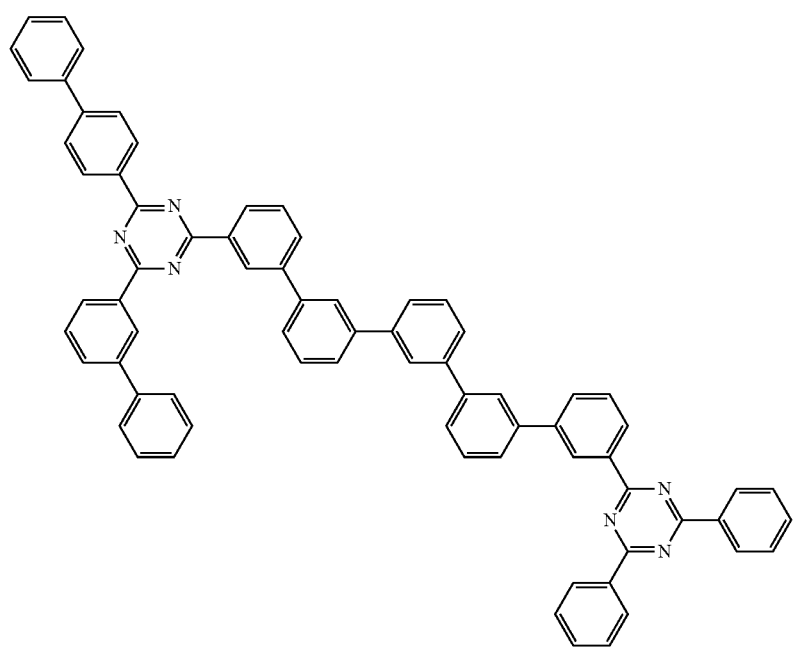
104

105
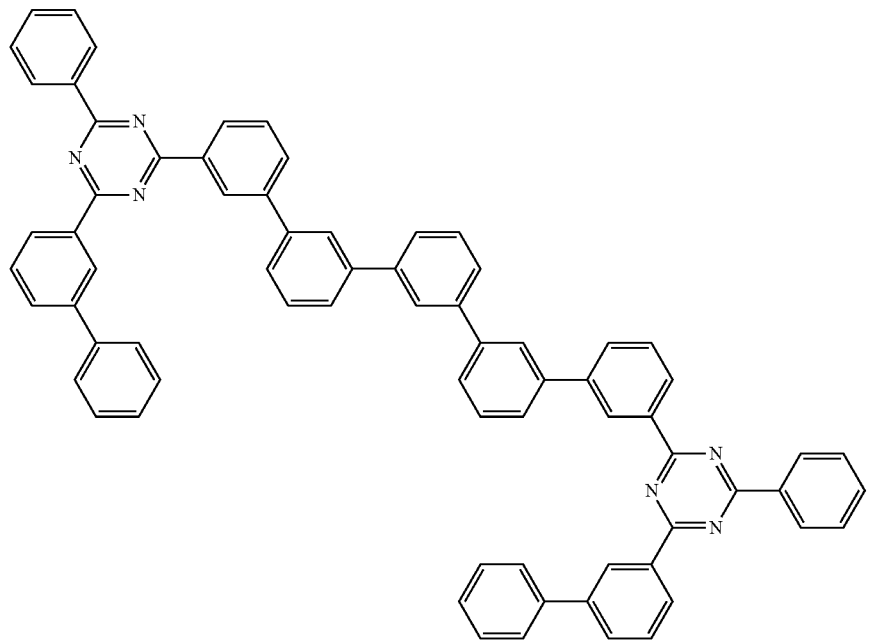
106
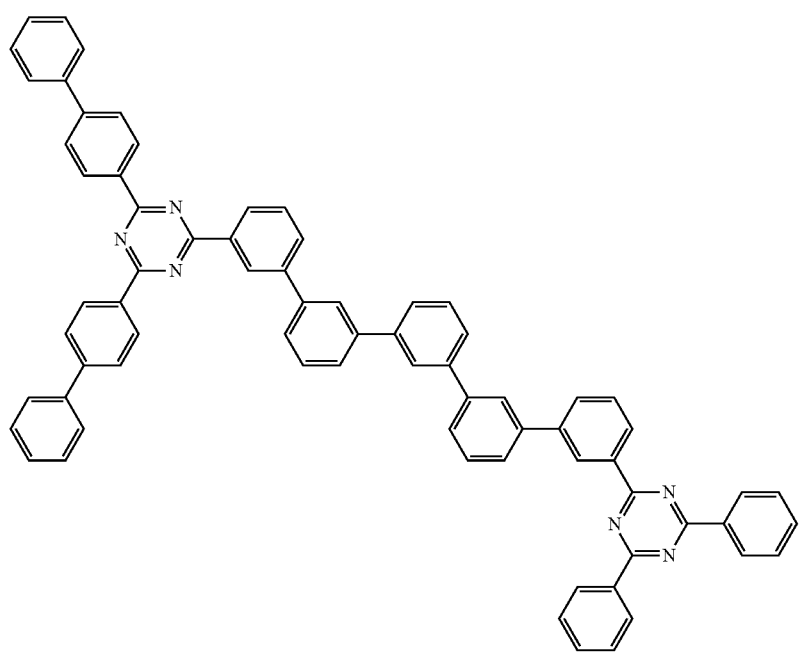

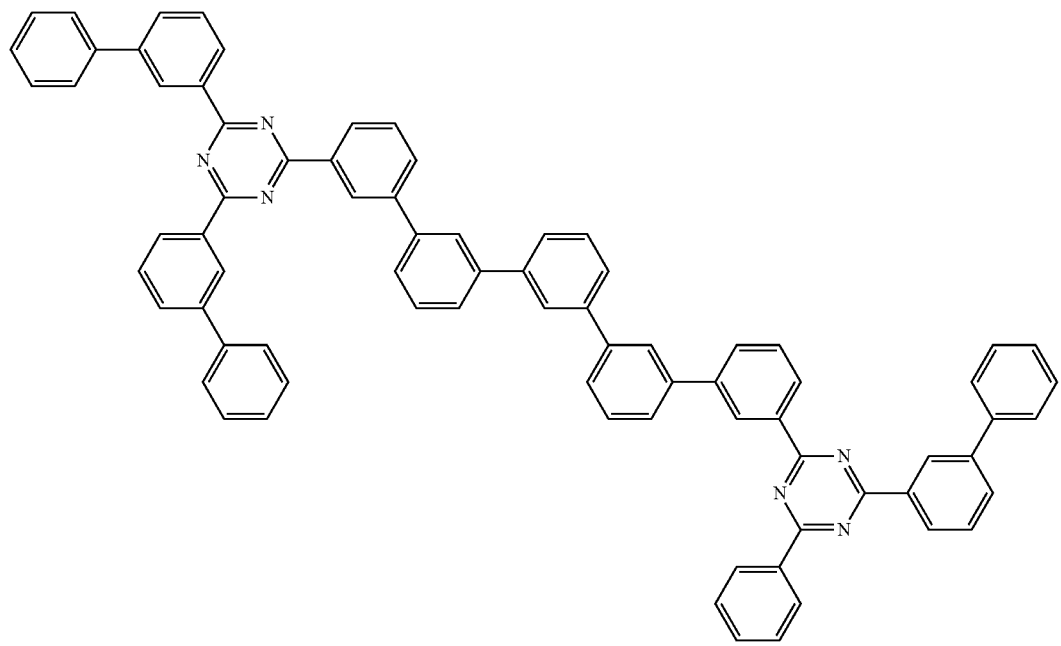
107
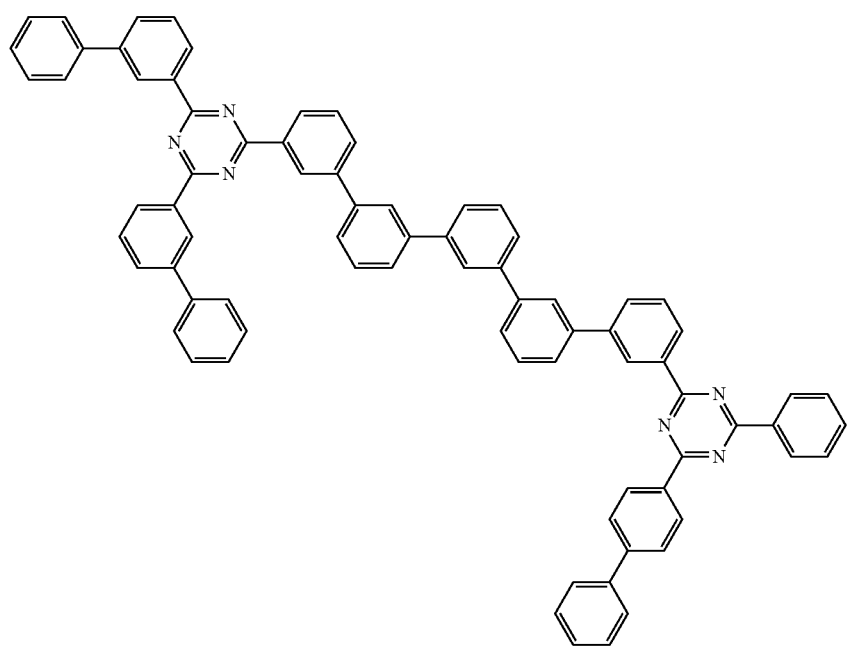
108

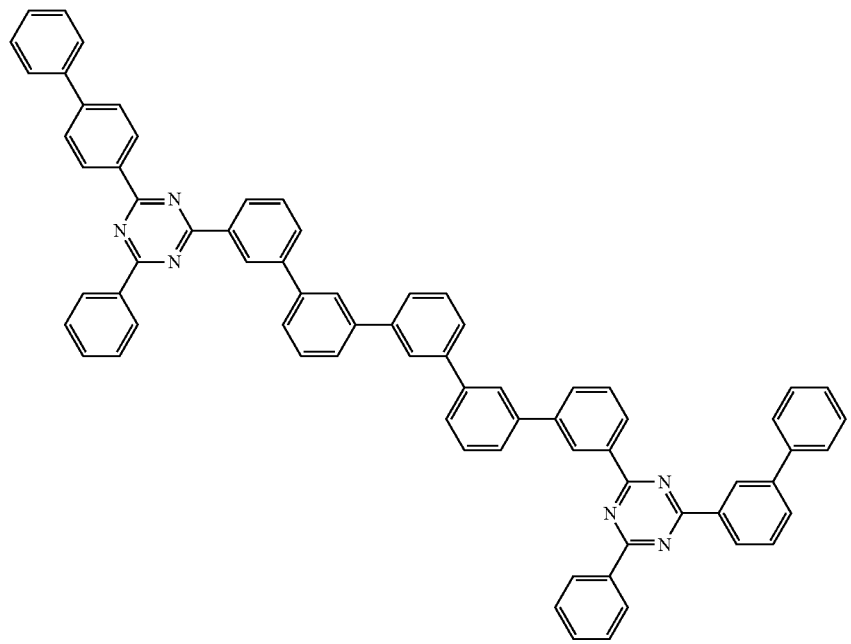
109
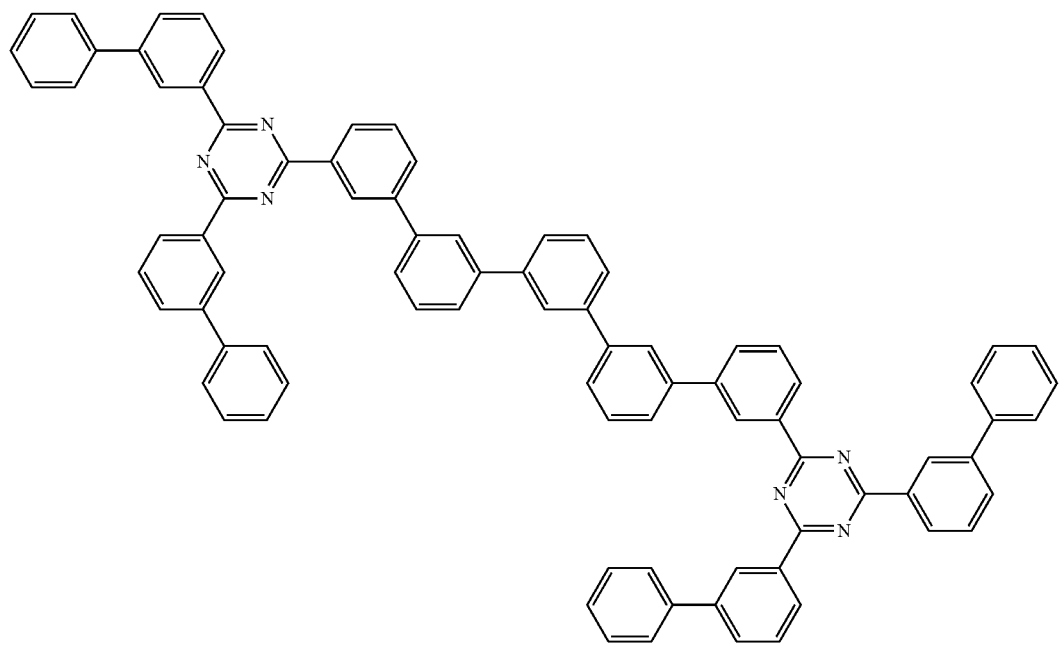
110

-continued

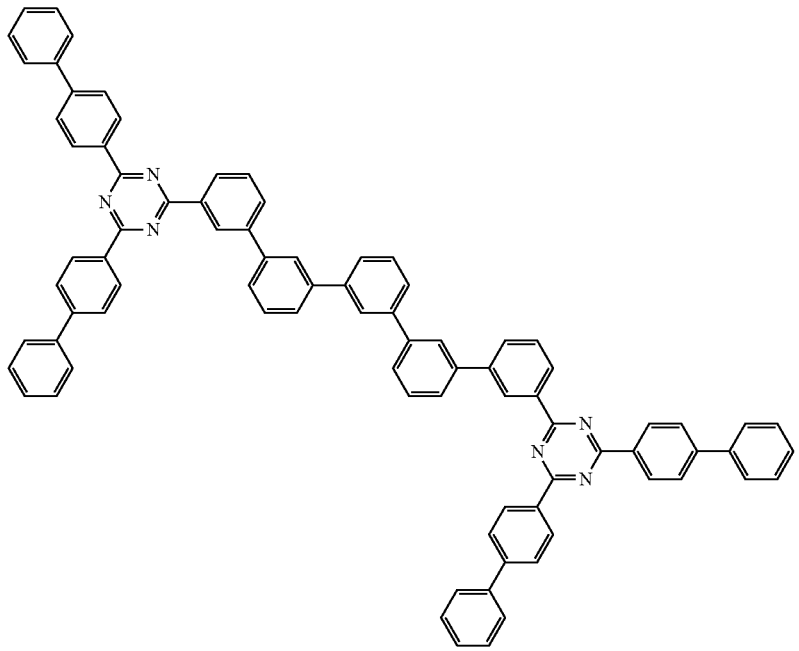

Hereinafter, an organic optoelectric device including the compound for an organic optoelectric device is described.

An organic optoelectric device according to another embodiment includes an anode and a cathode facing each other and at least one organic layer disposed between the anode and the cathode, wherein the organic layer includes the compound for an organic optoelectric device.

The organic layer may include a light emitting layer and the light emitting layer may include the compound for an organic optoelectric device. For example, it may be included as a host of the light emitting layer. As specific examples, it may be included as a green phosphorescent host.

In addition, the organic layer may further include at least one auxiliary layer selected from a hole blocking layer and an electron transport layer and the auxiliary layer may include the compound for an organic optoelectric device.

The auxiliary layer may further include an electron transport auxiliary layer that is adjacent to the light emitting layer and the electron transport auxiliary layer may include the compound for an organic optoelectric device.

The organic optoelectric device may be any device to convert electrical energy into photoenergy and vice versa without particular limitation, and may be, for example an organic photoelectric device, an organic light emitting diode, an organic solar cell, and an organic photo conductor drum.

Herein, an organic light emitting diode as one example of an organic optoelectric device is described referring to drawings.

FIG. 1 is a schematic cross-sectional view of an organic optoelectric device according to an embodiment.

Referring to FIG. 1, an organic optoelectric device according to an embodiment includes an anode 10 and a cathode 20 facing each other and an organic layer 30 between the anode 10 and the cathode 20.

The anode 10 may be made of a conductor having a large work function to help hole injection and may be for example made of a metal, a metal oxide and/or a conductive polymer.

The anode 10 may be for example a metal nickel, platinum, vanadium, chromium, copper, zinc, gold, and the like or an alloy thereof; metal oxide such as zinc oxide, indium oxide, indium tin oxide (ITO), indium zinc oxide (IZO), and the like; a combination of metal and oxide such as ZnO and Al or $SnO_2$ and Sb; a conductive polymer such as poly(3-methylthiophene), poly(3,4-(ethylene-1,2-dioxy)thiophene) (PEDT), polypyrrole, and polyaniline, but is not limited thereto.

The cathode 20 may be made of a conductor having a small work function to help electron injection, and may be for example made of a metal, a metal oxide and/or a conductive polymer. The cathode 20 may be for example a metal or an alloy thereof such as magnesium, calcium, sodium, potassium, titanium, indium, yttrium, lithium, gadolinium, aluminum silver, tin, lead, cesium, barium, and the like; a multi-layer structure material such as LiF/Al, $LiO_2$/Al, LiF/Ca, LiF/Al and $BaF_2$/Ca, but is not limited thereto.

The organic layer 30 includes a hole transport layer 31, a light emitting layer 32, and a hole transport auxiliary layer 33 between the hole transport layer 31 and the light emitting layer 32. In addition, an electron transport layer 34 and an electron transport auxiliary layer 35 between the electron transport layer 34 and the light emitting layer 32. The compound for an organic optoelectric device of the present invention may be included in these organic layers, for example an electron transport auxiliary layer. The organic light emitting diode may be manufactured by forming an anode or a cathode on a substrate, forming an organic layer using a dry film formation method such as a vacuum deposition method (evaporation), sputtering, plasma plating, and ion plating or a wet coating method such as spin coating, dipping, and flow coating, and forming a cathode or an anode thereon.

Referring to FIG. 2, the organic layer 30 may further include a hole injection layer 37 between the hole transport layer 31 and the anode 10 and an electron injection layer 36 between the electron transport layer 34 and the cathode 20.

The hole injection layer 37 between the hole transport layer 31 and the anode 10 may improve interface properties between ITO as an anode and an organic material used for the hole transport layer 31, and is applied on a non-planarized ITO and thus planarizes the surface of the ITO. For example, the hole injection layer 37 may include a material having a median value, particularly desirable conductivity between a work function of ITO and HOMO of the hole transport layer 31, in order to adjust a difference a work function of ITO as an anode and HOMO of the hole transport layer 31. In connection with the present invention, the hole injection layer 37 may include N4,N4'-diphenyl-N4,N4'-bis (9-phenyl-9H-carbazol-3-yl)biphenyl-4,4'-diamine), but is not limited thereto. In addition, the hole injection layer 37 may further include a conventional material, for example, copper phthlalocyanine (CuPc), aromatic amines such as N,N'-dinaphthyl-N,N'-phenyl-(1,1'-biphenyl)-4,4'-diamine (NPD), 4,4',4''-tris[methylphenyl(phenyl)amino] triphenyl amine (m-MTDATA), 4,4',4''-tris[1-naphthyl(phenyl) amino] triphenyl amine (1-TNATA), 4,4',4''-tris[2-naphthyl (phenyl)amino]triphenyl amine (2-TNATA), 1,3,5-tris[N-(4-diphenylaminophenyl)phenylamino] benzene (p-DPA-TDAB), and the like, compounds such as 4,4'-bis[N-[4-{N, N-bis(3-methylphenyl)amino}phenyl]-N-phenylamino] biphenyl (DNTPD), hexaazatriphenylene-hexacarbonitirile (HAT-CN), and the like, a polythiophene derivative such as poly(3,4-ethylenedioxythiophene)-poly(styrnesulfonate) (PEDOT) as a conductive polymer. The hole injection layer 37 may be for example coated on ITO as an anode in a thickness of 10 to 300 Å.

The electron injection layer 36 is disposed on an electron transport layer and may play a role of facilitating an electron injection from a cathode and ultimately improving power efficiency and be formed by using any material used in a related art without a particular limit, for example, LiF, Liq, NaCl, CsF, Li$_2$O, BaO, and the like.

The hole transport layer 31 may facilitate hole transport from the anode 10 to the light emitting layer 32 and may include for example an amine compound, but is not limited thereto.

The amine compound may include for example at least one aryl group and/or heteroaryl group. The amine compound may be for example represented by Chemical Formula a or Chemical Formula b, but is not limited thereto.

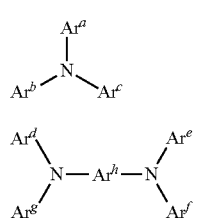

[Chemical Formula a]

[Chemical Formula b]

In Chemical Formula a or Chemical Formula b, $Ar^a$ to $Ar^g$ are independently hydrogen, deuterium, a substituted or unsubstituted C1 to C20 alkyl group, a substituted or unsubstituted C6 to C30 aryl group, a substituted or unsubstituted C2 to C30 heteroaryl group, or a combination thereof, at least one of $Ar^a$ to $Ar^c$ and at least one of $Ar^d$ to $Ar^g$ are a substituted or unsubstituted C6 to C30 aryl group, a substituted or unsubstituted C2 to C30 heteroaryl group, or a combination thereof, and $Ar^h$ is a single bond, a substituted or unsubstituted C1 to C20 alkylene group, a substituted or unsubstituted C6 to C30 arylene group, a substituted or unsubstituted C2 to C30 heteroarylene group, or a combination thereof.

The electron transport layer 34 facilitates electron transport from the cathode 20 into the light emitting layer 32, and may include an organic compound having an electron accepting functional group (electron withdrawing group), a metallic compound capable of accepting electrons well, or a mixture thereof. For example, as an electron transport layer material, it may include aluminum trihydroxyquinoline (Alq$_3$), 2-(4-biphenylyl)-5-phenyl-1,3,4-oxadiazole (PBD) that is a 1,3,4-oxadiazole derivative, 1,3,4-tris[(3-phenyl-6-trifluoromethyl)quinoxaline-2-yl] benzene (TPQ) that is a quinoxaline derivative, a triazole derivative, and 8-(4-(4-(naphthalen-2-yl)-6-(naphthalen-3-yl)-1,3,5-triazin-2-yl) phenyl)quinoline) that is a triazine derivative, and the like, but is not limited thereto.

In addition, the electron transport layer may use an organometallic compound represented by Chemical Formula c alone or as a mixture with the electron transport layer material.

$$Y_m\text{-}M\text{-}(OA)_n \qquad \text{[Chemical Formula c]}$$

In Chemical Formula c,

Y includes a moiety consisting a single bond by a direct bond between one of C, N, O, and S, and M and a moiety consisting of a coordination bond between one of C, N, O, and S, and M and is a ligand chelated by the single bond and the coordination bond, M is an alkali metal, an alkali earth metal, aluminum (Al), or a boron (B) atom. OA is a monovalent ligand capable of single-bonding or coordination-bonding with M, O is oxygen.

A is one of a substituted or unsubstituted C1 to C30 alkyl group, a substituted or unsubstituted C5 to C50 aryl group, a substituted or unsubstituted C2 to C30 alkenyl group, a substituted or unsubstituted C2 to C20 alkynyl group, a substituted or unsubstituted C3 to C30 cycloalkyl group, a substituted or unsubstituted C5 to C30 cycloalkenyl group, and a substituted or unsubstituted C2 to C50 heteroaryl group having O, N, or S as a heteroatom, when M is one metal selected from the alkali metal, m=1 and n=0, when M is one metal selected from the alkali earth metal, m=1 and n=1 or m=2 and n=0, when M is boron or aluminum, m is an integer ranging from 1 to 3 and n is an integer of 0 to 2, and m+n=3, and 'substituted' in the 'substituted or unsubstituted' refers to substitution with one or more substituent selected from deuterium, a cyano group, a halogen, a hydroxy group, a nitro group, an alkyl group, an alkoxy group, an alkylamino group, an arylamino group, a heteroaryl amino group, an alkylsilyl group, an arylsilyl group, an aryloxy group, an aryl group, a heteroaryl group, germanium, phosphorus, and boron.

In the present invention, Y may be the same or different and may independently be selected from Chemical Formula c1 to Chemical Formula c39, but is not limited thereto.

[Chemical Formula c1]
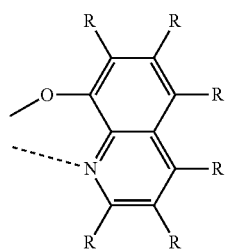
[Chemical Formula c2]
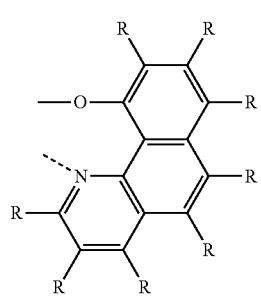
[Chemical Formula c3]
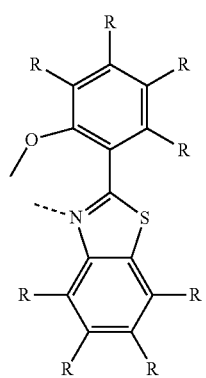
[Chemical Formula c4]
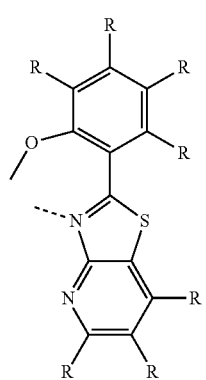
[Chemical Formula c5]
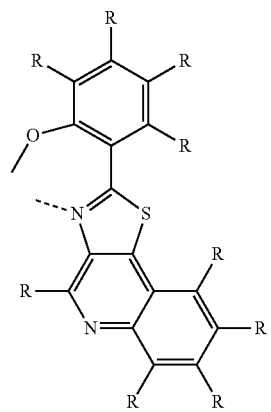
[Chemical Formula c6]
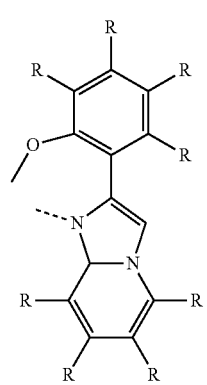
[Chemical Formula c7]
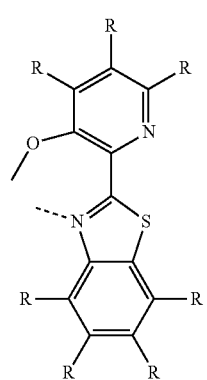
[Chemical Formula c8]
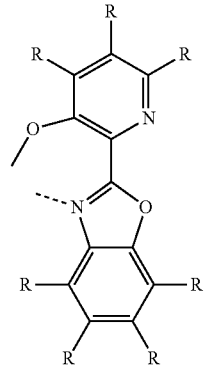

[Chemical Formula c9]
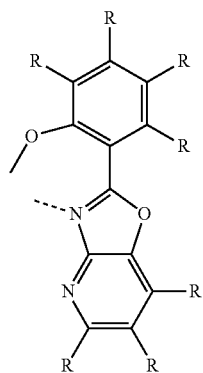
[Chemical Formula c10]
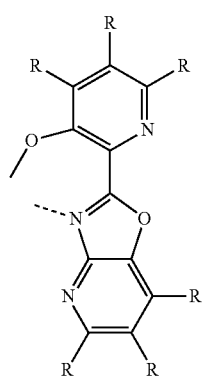
[Chemical Formula c11]
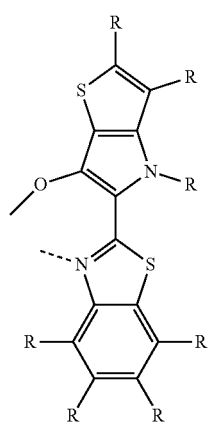
[Chemical Formula c12]
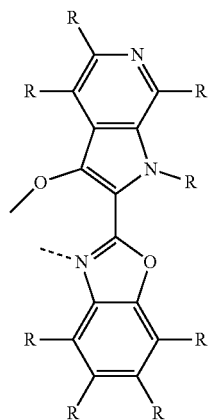
[Chemical Formula c13]
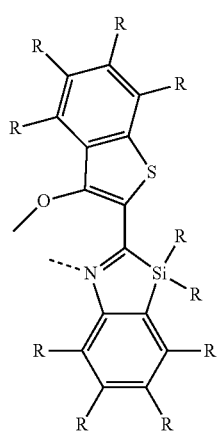
[Chemical Formula c14]
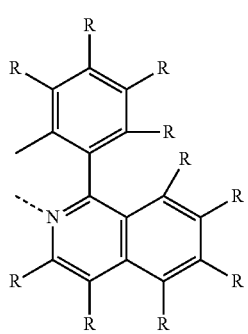
[Chemical Formula c15]
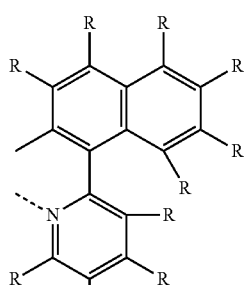
[Chemical Formula c16]
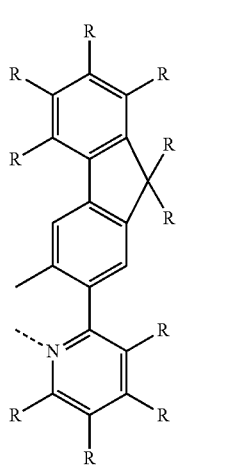

[Chemical Formula c17]
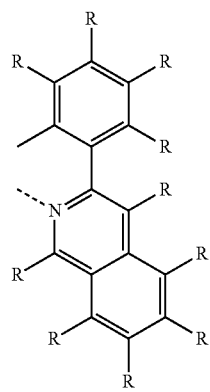
[Chemical Formula c18]
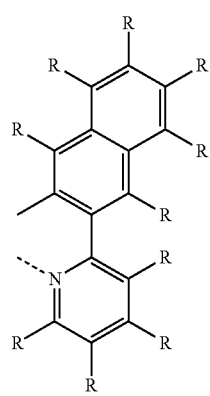
[Chemical Formula c19]
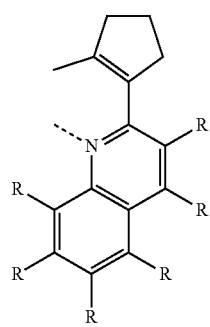
[Chemical Formula c20]
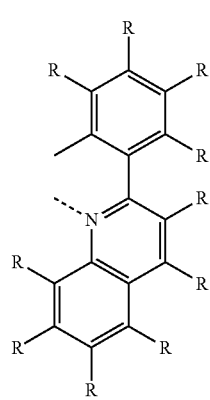
[Chemical Formula c21]
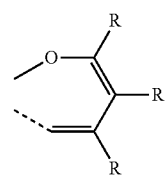
[Chemical Formula c22]
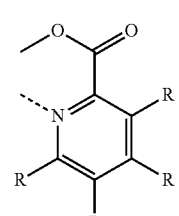
[Chemical Formula c23]
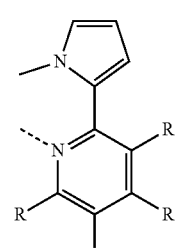
[Chemical Formula c24]
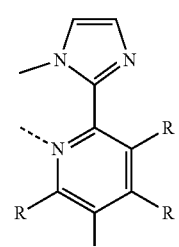
[Chemical Formula c25]
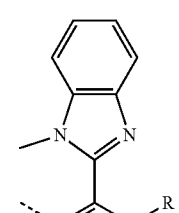
[Chemical Formula c26]
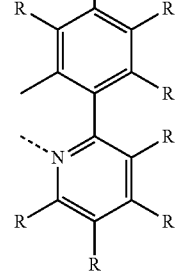

93
-continued
[Chemical Formula c27]
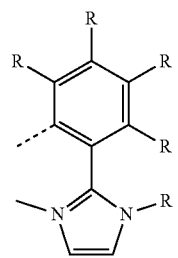
[Chemical Formula c28]
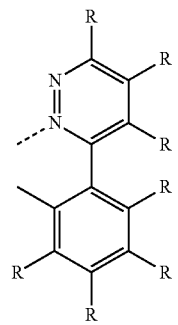
[Chemical Formula c29]
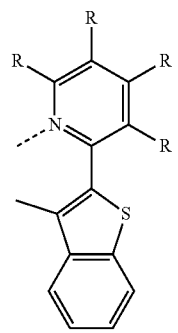
[Chemical Formula c30]
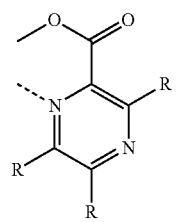
[Chemical Formula c31]
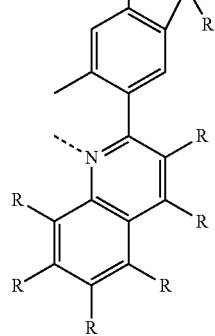
94
-continued
[Chemical Formula c32]
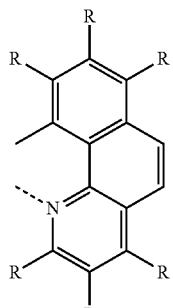
[Chemical Formula c33]
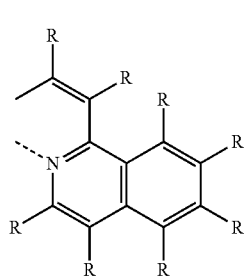
[Chemical Formula c34]
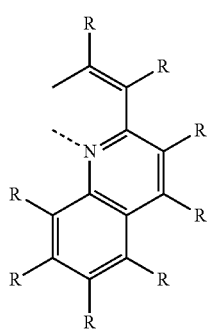
[Chemical Formula c35]
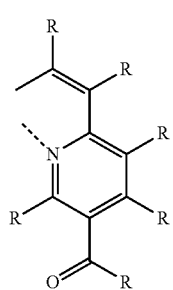
[Chemical Formula c36]
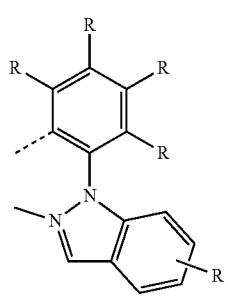

-continued

[Chemical Formula c37]

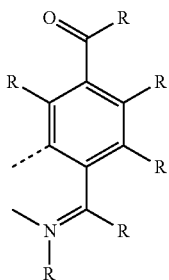

[Chemical Formula c38]

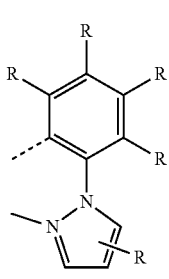

[Chemical Formula c39]

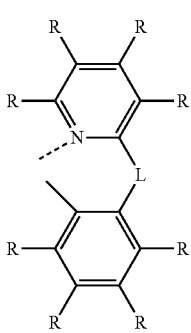

In Chemical Formula c1 to Chemical Formula c39,
R is the same or different and is independently selected from hydrogen, deuterium, a halogen, a cyano group, a substituted or unsubstituted C1 to C30 alkyl group, a substituted or unsubstituted C6 to C30 aryl group, a substituted or unsubstituted C3 to C30 heteroaryl group, a substituted or unsubstituted C1 to C30 alkoxy group, a substituted or unsubstituted C3 to C30 cycloalkyl group, a substituted or unsubstituted C2 to C30 alkenyl group, a substituted or unsubstituted C1 to C30 alkylamino group, a substituted or unsubstituted C1 to C30 alkylsilyl group, a substituted or unsubstituted C6 to C30 arylamino group and a substituted or unsubstituted C6 to C30 arylsilyl group, or is linked to an adjacent substitutent with alkylene or alkenylene to from a spiro ring or a fused ring.

The light emitting layer 32 is an organic layer capable of emitting light and includes a host and a dopant when a doping system is adopted. Herein, the host mainly promotes a recombination of electrons and confines and holds excitons in a light emitting layer, while the dopant efficiently emits light from the excitons obtained from the recombination.

The organic light emitting diode may be applied to an organic light emitting display device.

Hereinafter, the embodiments are illustrated in more detail with reference to examples. These examples, however, are not in any sense to be interpreted as limiting the scope of the invention.

(Synthesis of Compound for Organic Optoelectric Device)

Hereinafter, a starting material and a reactant used in Examples and Synthesis Examples were purchased from Sigma-Aldrich Co. Ltd. or TCI Inc. as far as there is no particular description.

Synthesis Example 1: Synthesis of Compound 1

Synthesis of Intermediate 1-1

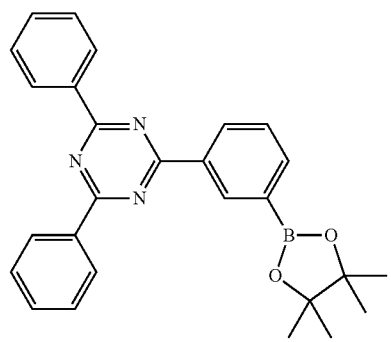

1-1

20 g (51.51 mmol) of 2-(3-bromophenyl)-4,6-diphenyl-1,3,5-triazine was dissolved in 250 mL of toluene in a 500 mL round-bottomed flask. 0.05 equivalents of dichlorodiphenylphosphinoferrocene palladium, 1.2 equivalents of bis(pinacolato diboron), and 2 equivalents of potassium acetate were added thereto, and the mixture was heated and refluxed under a nitrogen atmosphere for 18 hours. The reaction solution was cooled down, and 100 mL of water was added thereto to extract an organic layer. The organic layer was gathered and treated with activated carbon and then, filtered with silica gel, and a filtrate was concentrated. The concentrated residue was gathered and crystallized in 200 mL of toluene and 50 mL of acetone to obtain 19.1 g of Intermediate 1-1.

Synthesis of Compound 1

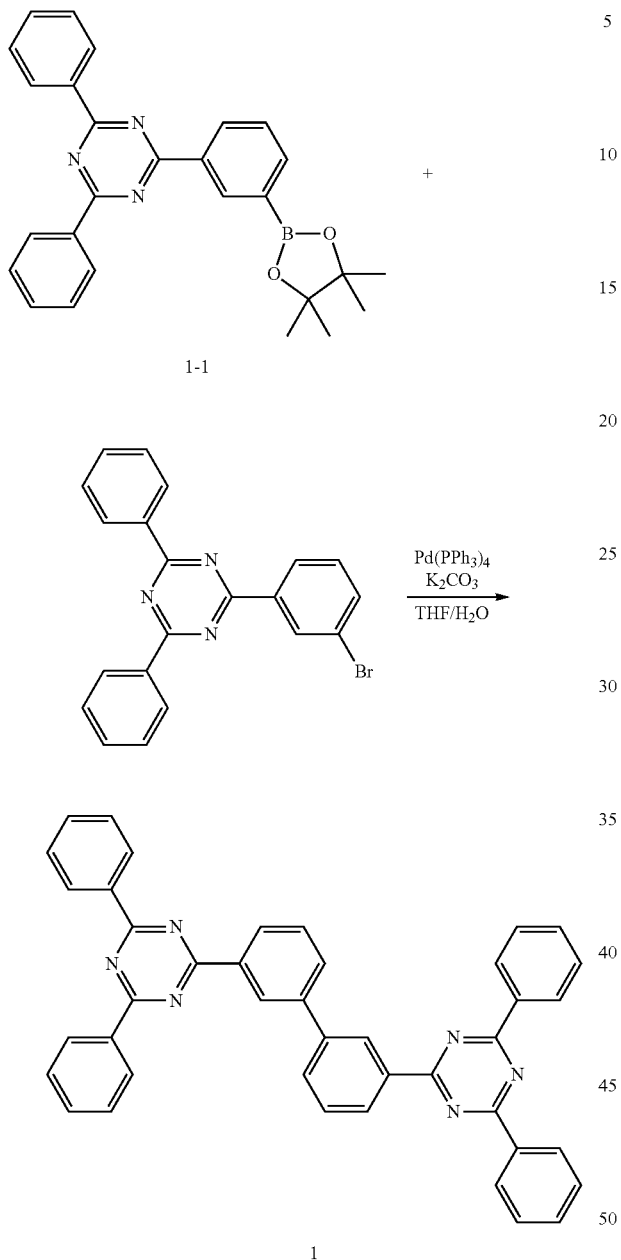

1

19 g (43.79 mmol) of Intermediate 1-1, 200 mL of tetrahydrofuran, and 50 mL of distilled water were put in a 500 mL round-bottomed flask, 1 equivalent of 2-(3-bromophenyl)-4,6-diphenyl-1,3,5-triazine, 0.03 equivalents of tetrakistriphenylphosphine palladium, and 2 equivalents of potassium carbonate were added thereto, and the mixture was heated and refluxed under a nitrogen atmosphere. After 18 hours, the reaction solution was cooled down, and a solid precipitated therein was filtered and washed with 500 mL of water. The solid was recrystallized with 500 mL of monochlorobenzene to obtain 22.41 g of Compound 1.

LC/MS calculated for: C42H28N6 Exact Mass: 616.2375 found for: 617.24 [M+H].

Synthesis Example 2: Synthesis of Compound 2

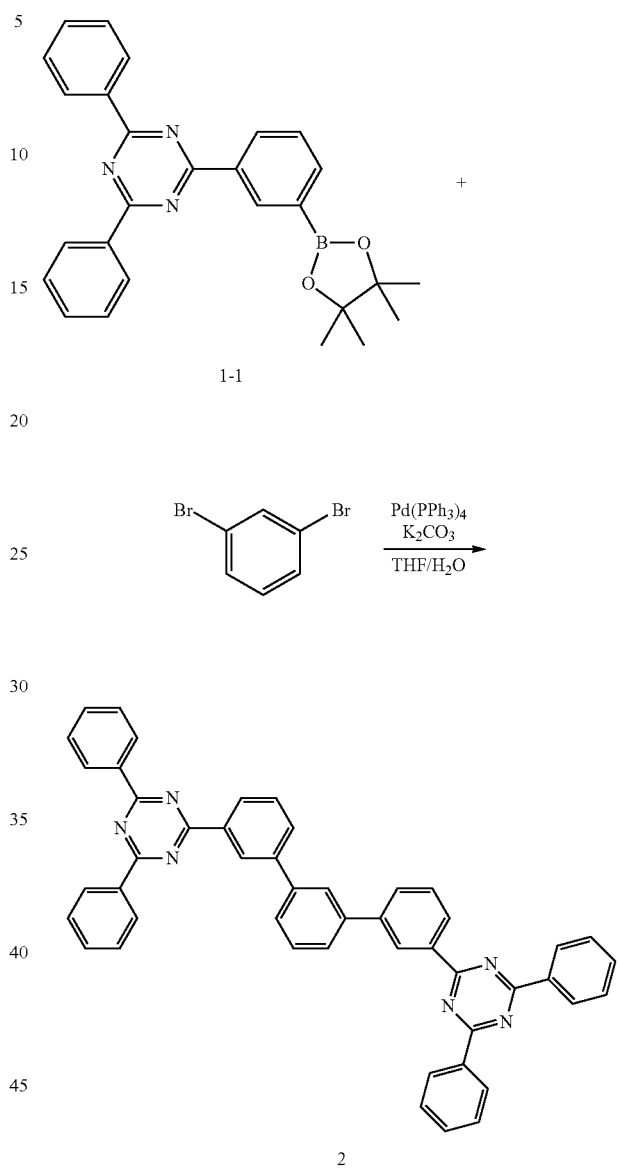

2

15 g (34.46 mmol) of Intermediate 1-1, 0.5 equivalents of 1,3-dibromobenzene, 0.03 equivalents of tetrakistriphenylphosphine palladium, 2 equivalents of potassium carbonate, 200 mL of tetrahydrofuran, and 50 mL of distilled water were put in a 500 mL round-bottomed flask and then, heated and refluxed under a nitrogen atmosphere. After 20 hours, the reaction solution was cooled down, and a solid precipitated therein was filtered and washed with 500 mL of water. The solid was recrystallized with 400 mL of dichlorobenzene to obtain 9.2 g of Compound 2.

LC/MS calculated for: C48H32N6 Exact Mass: 692.2688 found for: 693.27 [M+H].

Synthesis Example 3: Synthesis of Compound 3

Synthesis of Intermediate 3-1

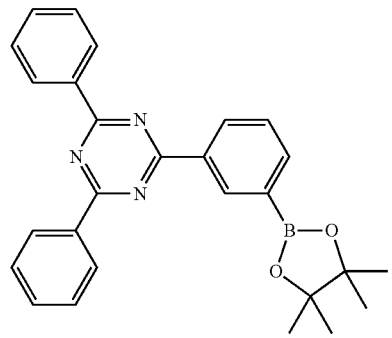

1-1

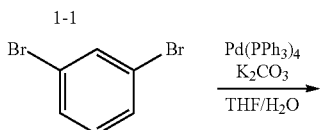

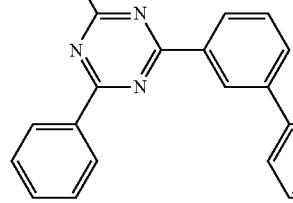

3-1

30 g (68.92 mmol) of Intermediate 1-1, 1.2 equivalents of 1,3-dibromobenzene, 0.03 equivalents of tetrakistriphenyl phosphine palladium, 2 equivalents of potassium carbonate, 300 mL of tetrahydrofuran, and 100 mL of distilled water were put in a 500 mL round-bottomed flask and then, heated and refluxed under a nitrogen atmosphere. After 18 hours, the reaction solution was cooled down, suspended in 1 L of methanol, stirred and filtered, and then, washed with 500 mL of water. The solid was recrystallized with 400 mL of dichlorobenzene to obtain 32 g of Intermediate 3-1.

Synthesis of Intermediate 3-2

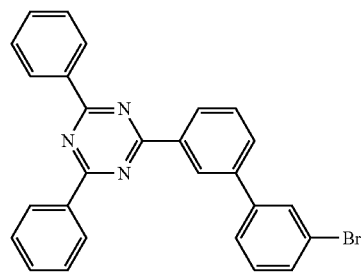

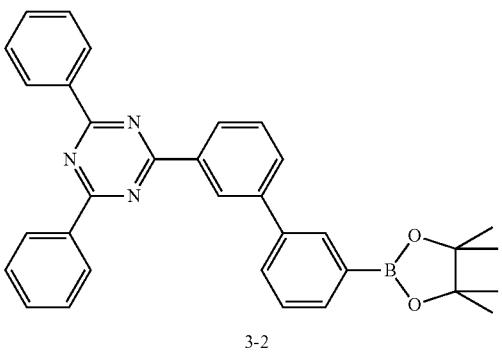

3-2

32 g (68.91 mmol) of Intermediate 3-1 and toluene 350 mL 500 mL round-bottomed flask, 0.05 equivalents of dichlorodiphenylphosphinoferrocene palladium, 1.2 equivalents of bis(pinacolato diboron), and 2 equivalents of potassium acetate were added thereto, and the mixture was heated and refluxed under a nitrogen atmosphere for 18 hours. The reaction solution was cooled down, and 100 mL of water was added thereto to extract an organic layer. The organic layer was gathered and treated with activated carbon and then, filtered with silica gel, and a filtrate therefrom was concentrated. The concentrated residue was gathered, heated and dissolved in 1 L of toluene, treated with activated carbon, and filtered with silica gel. The obtained filtrate was cooled down and stirred to precipitate a solid. The precipitated solid was filtered to obtain 29.96 g of Intermediate 3-2.

Synthesis of Compound 3

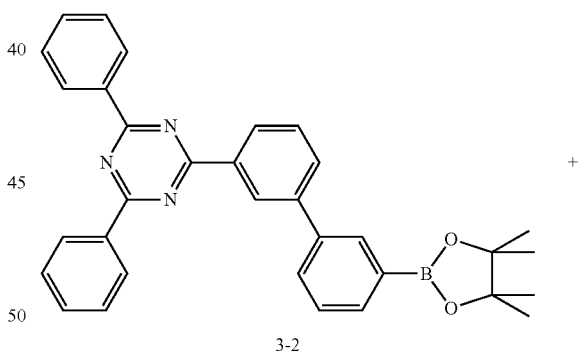

3-2

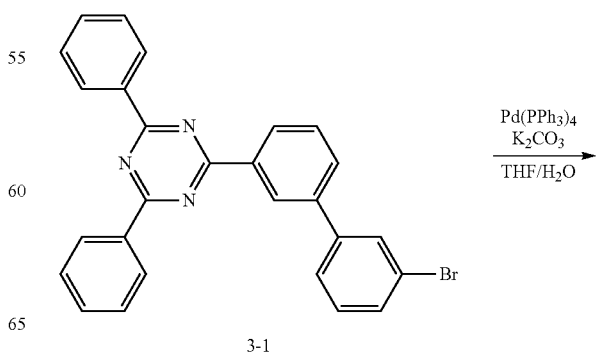

3-1

-continued

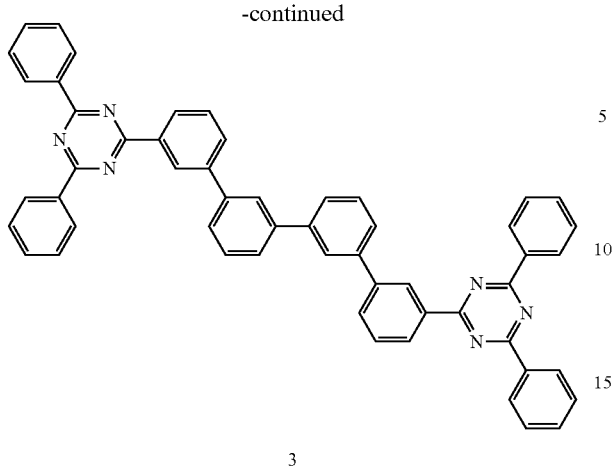

3

15 g (29.33 mmol) of Intermediate 3-2, 1 equivalent of Intermediate 3-1, 0.03 equivalents of tetrakistriphenylphosphine palladium, 2 equivalents of potassium carbonate, 200 mL of tetrahydrofuran, and 50 mL of distilled water were put in a 500 mL round-bottomed flask and then, heated and refluxed under a nitrogen atmosphere. After 18 hours, the reaction solution was cooled down and then, filtered and washed with 500 mL of water. The solid was recrystallized with 500 mL of dichlorobenzene to obtain 16.01 g of Compound 3.

LC/MS calculated for: C54H36N6 Exact Mass: 768.3001 found for: 769.3 [M+H].

Synthesis Example 4: Synthesis of Compound 100

Synthesis of Intermediate 100-1

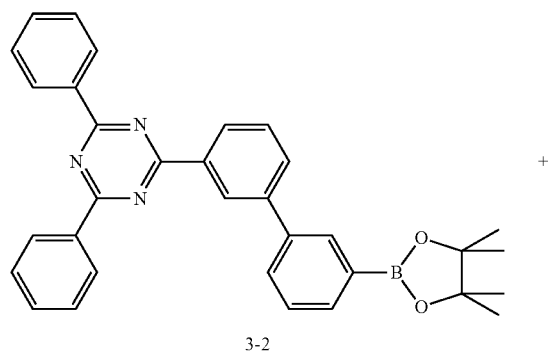

-continued

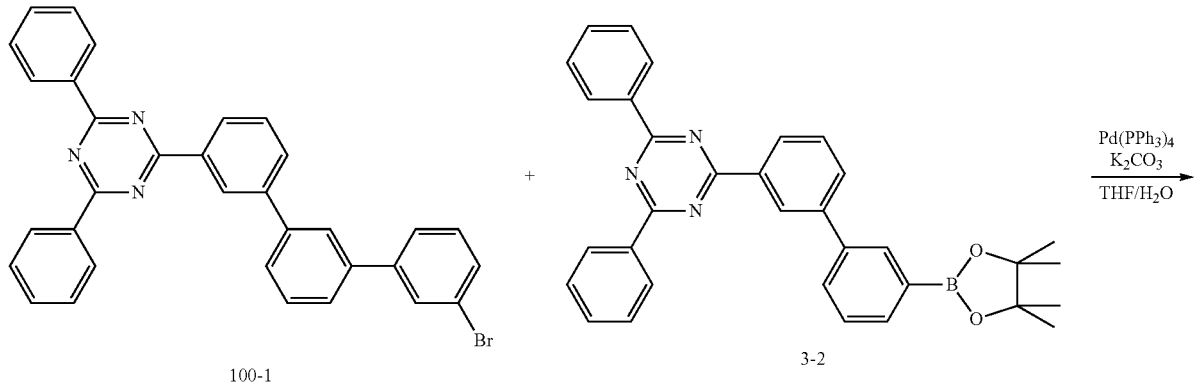

15 g (29.33 mmol) of Intermediate 3-2, 1.2 equivalents of 1,3-dibromobenzene, 0.03 equivalents of tetrakistriphenylphosphine palladium, 2 equivalents of potassium carbonate, 300 mL of tetrahydrofuran, and 100 mL of distilled water were put in a 500 mL round-bottomed flask and then, heated and refluxed under a nitrogen atmosphere. After 18 hours, the reaction solution was cooled down, suspended in 1 L of methanol 1 L, stirred and filtered, and then, washed with 500 mL of water. The solid was recrystallized with 300 mL of dichlorobenzene to obtain 12.84 g of Intermediate 100-1.

Synthesis of Compound 100

-continued

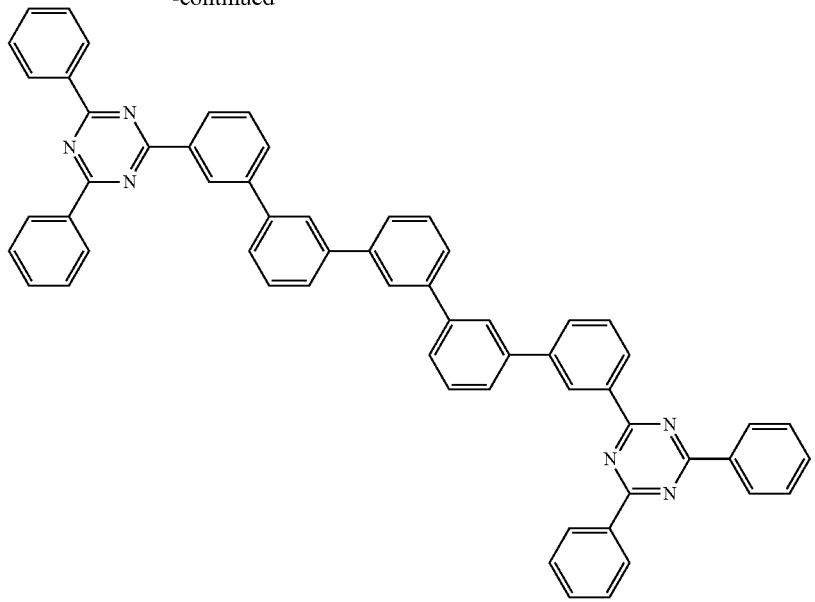

100

12 g (22.2 mmol) of Intermediate 100-1, 1.2 equivalents of Intermediate 3-2, 0.03 equivalents of tetrakistriphenylphosphine palladium, 2 equivalents of potassium carbonate, 150 mL of tetrahydrofuran, and 50 mL of distilled water were put in a 500 mL round-bottomed flask and then, heated and refluxed under a nitrogen atmosphere. After 18 hours, the reaction solution was cooled down, suspended in 1 L of methanol, stirred and filtered, and then, washed with 500 mL of water. The obtained solid was recrystallized with 500 mL of dichlorobenzene to obtain 13.3 g of Compound 100.

LC/MS calculated for: C60H40N6 Exact Mass: 844.3314 found for 845.34 [M+H].

Synthesis Example 5: Synthesis of Compound 4

Synthesis of Intermediate 4-2

15 g (81.34 mmol) of cyanuric chloride was dissolved in 200 mL of anhydrous tetrahydrofuran in a 500 mL round-bottomed flask, 1 equivalent of a 4-biphenyl magnesium bromide solution (0.5 M tetrahydrofuran) was added thereto in a dropwise fashion at 0° C. under a nitrogen atmosphere, and the mixture was slowly heated up to room temperature. The reaction solution was stirred at room temperature for 1 hour and then, added to 500 mL of ice water to separate layers. An organic layer was separated therefrom and then, treated with anhydrous magnesium sulfate and concentrated. The concentrated residue was recrystallized with tetrahydrofuran and methanol to obtain 17.2 g of Intermediate 4-2.

Synthesis of Intermediate 4-1

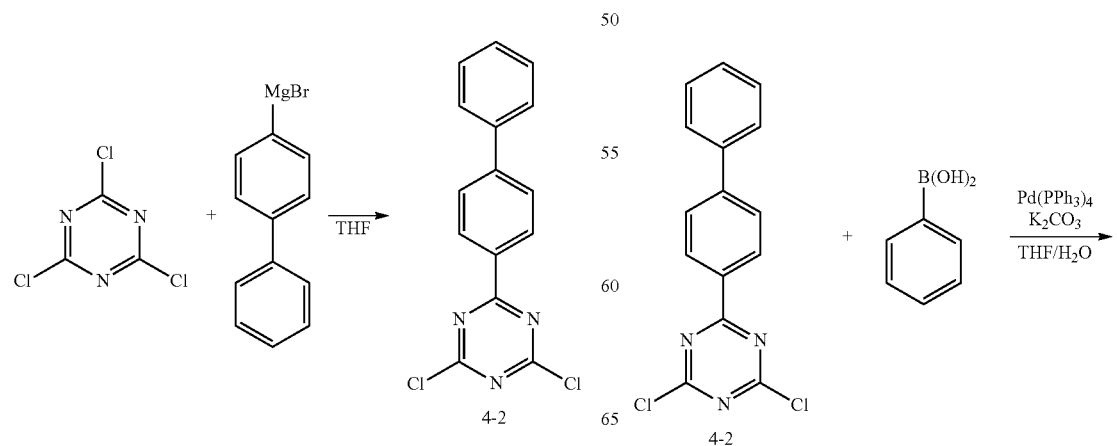

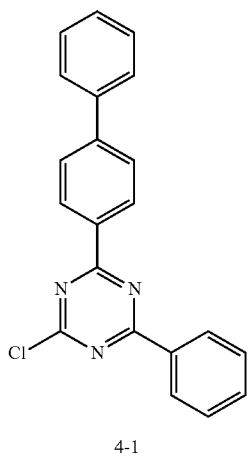

4-1

17 g (56.26 mmol) of Intermediate 4-2 was put in a 500 mL round-bottomed flask, 1 equivalent of phenylboronic acid, 0.03 equivalents of tetrakistriphenylphosphine palladium, 2 equivalents of potassium carbonate, 150 mL of tetrahydrofuran water, and 50 mL of distilled water were added thereto, and the mixture was heated and refluxed under a nitrogen atmosphere. After 18 hours, the reaction solution was cooled down, suspended in 1 L of methanol, stirred and filtered, washed with 500 mL of water, and dried to obtain 12.57 g of Intermediate 4-1.

Synthesis of Compound 4

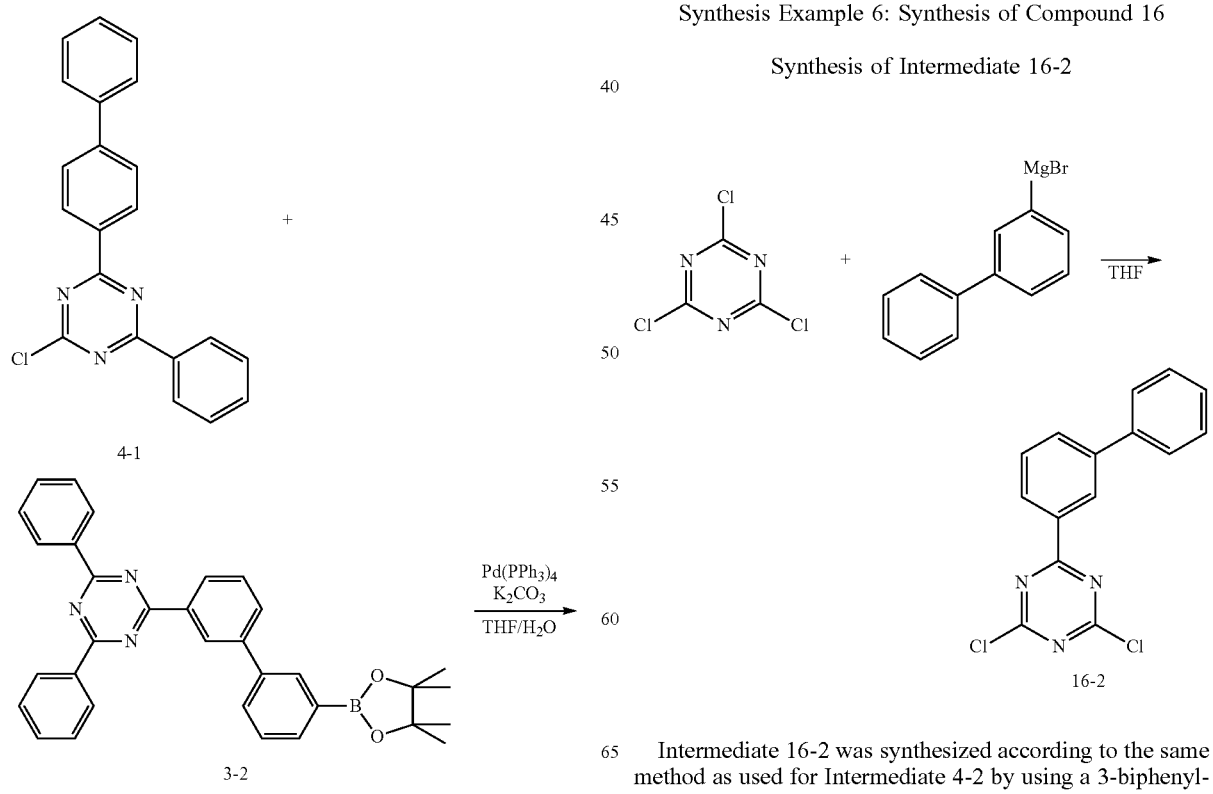

4-1

3-2

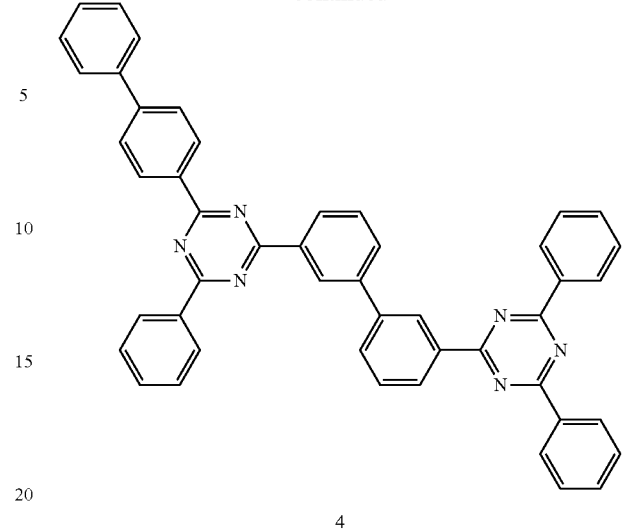

4

12 g (34.9 mmol) of Intermediate 4-1 was put in a 500 mL round-bottomed flask, 1.1 equivalents of Intermediate 3-2, 0.03 equivalents of tetrakistriphenylphosphine palladium, 2 equivalents of potassium carbonate, 150 mL of tetrahydrofuran, and 50 mL of distilled water were added thereto, and the mixture was heated and refluxed under a nitrogen atmosphere. After hours, the reaction solution was cooled down, suspended in 1 L of methanol, stirred and filtered, and then, washed with 500 mL of water. The produced solid was recrystallized with 500 mL of dichlorobenzene to obtain 17.8 g of Compound 4.

LC/MS calculated for: C48H32N6 Exact Mass: 692.2688 found for 692.27 [M+H].

Synthesis Example 6: Synthesis of Compound 16

Synthesis of Intermediate 16-2

16-2

Intermediate 16-2 was synthesized according to the same method as used for Intermediate 4-2 by using a 3-biphenyl-magnesiumbromide solution (0.5 M tetrahydrofuran).

Synthesis of Intermediate 16-1

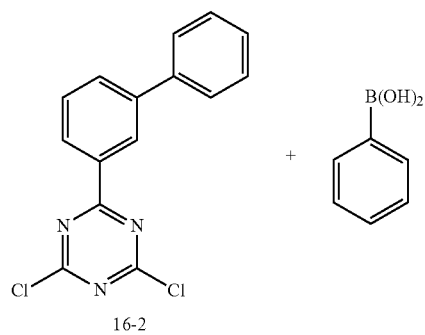

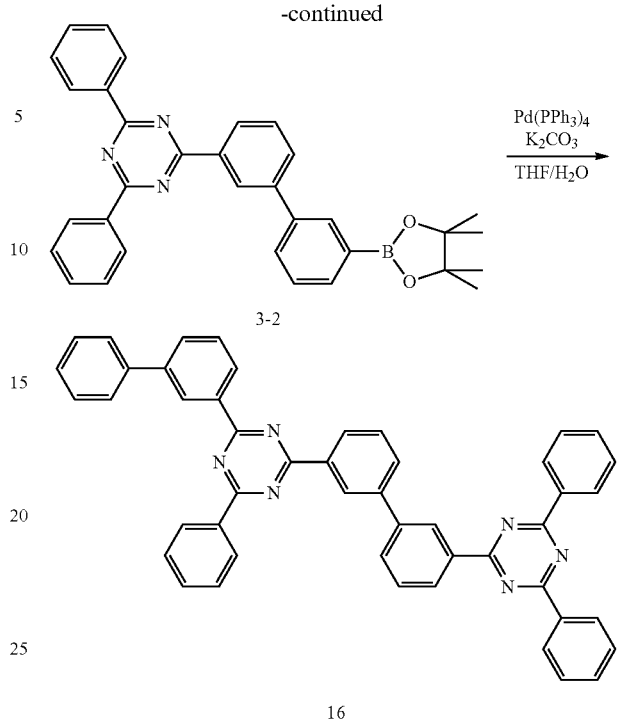

Intermediate 16-1 was synthesized according to the same method as used for Intermediate 4-1 by using Intermediate 16-2.

Synthesis of Compound 16

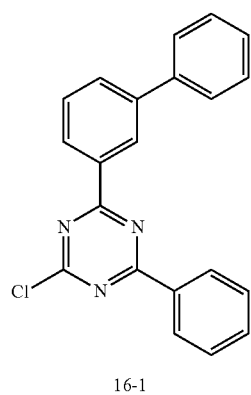

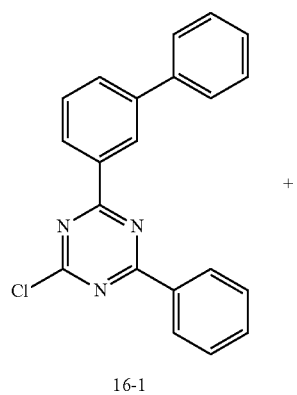

Compound 16 was synthesized according to the same method as used for Compound 4 by using Intermediate 16-1.

LC/MS calculated for: C48H32N6 Exact Mass: 692.2688 found for 692.27 [M+H].

Manufacture of Organic Light Emitting Diode

Example 1

An organic light emitting diode was manufactured by using Compound 1 according to Synthesis Example 1 as a host and Ir(PPy)$_3$ as a dopant.

A 1000 Å-thick ITO was used as an anode and a 1000 Å-thick aluminum (Al) as a cathode. Specifically, the organic light emitting diode was manufactured in a method of cutting an ITO glass substrate having sheet resistance of 15 Ω/cm$^2$ into a size of 50 mm×50 mm×0.7 mm, ultrasonic wave-cleaning it in acetone, isopropyl alcohol, and pure water respectively for 15 minutes and UV ozone-cleaning it for 30 minutes.

On the substrate, an 800 Å-thick hole transport layer was formed by depositing N4,N4'-di(naphthalen-1-yl)-N4,N4'-diphenylbiphenyl-4,4'-diamine (NPB) (80 nm) under a vacuum degree of 650×10$^{-7}$ Pa at a deposition rate of 0.1 to 0.3 nm/s. Subsequently, a 300 Å-thick film as a light emitting layer was formed by using the compound 1 according to Synthesis Example 1 under the same vacuum deposition condition as above, and Ir(PPy)$_3$ as a phosphorescent dopant was simultaneously deposited. Herein, the phosphorescent dopant was deposited in an amount of 7 wt % based on 100 wt % of the total amount of the light emitting layer by adjusting a deposition rate.

On the light emitting layer, a 50 Å-thick film as a hole blocking layer was formed by depositing bis(2-methyl-8-quinolinolate)-4-(phenylphenolato)aluminium (BAlq) under the same vacuum deposition condition as above. Subsequently, a 200 Å-thick film as an electron transport layer was formed by depositing Alq3 under the same vacuum deposition condition as above. On the electron transport layer. LiF and Al were sequentially deposited as a cathode, manufacturing the organic photoelectric device.

A structure of the organic photoelectric device was ITO/NPB (80 nm)/EML (Compound 1 (93 wt %)+Ir(PPy)$_3$ (7 wt %), 30 nm)/BAlq (5 nm)/Alq$_3$ (20 nm)/LiF (1 nm)/Al (100 nm).

Example 2

A device was manufactured according to the same method as Example 1 by using Compound 2 of Synthesis Example 2 as a host.

Example 3

A device was manufactured according to the same method as Example 1 by using Compound 3 of Synthesis Example 3 as a host.

Example 4

A device was manufactured according to the same method as Example 1 by using Compound 100 of Synthesis Example 4 as a host.

Example 5

A device was manufactured according to the same method as Example 1 by using Compound 4 of Synthesis Example 5 as a host.

Example 6

A device was manufactured according to the same method as Example 1 by using Compound 16 of Synthesis Example 6 as a host.

Comparative Example 1

A device was manufactured according to the same method as Example 1 by using the compound of Comparative Example 1 as a host.

Comparative Example 2

A device was manufactured according to the same method as Example 1 by using the compound of Comparative Example 2 as a host.

Comparative Example 3

A device was manufactured according to the same method as Example 1 by using the compound of Comparative Example 3 as a host.

Comparative Example 4

A device was manufactured according to the same method as Example 1 by using the compound of Comparative Example 4 as a host.

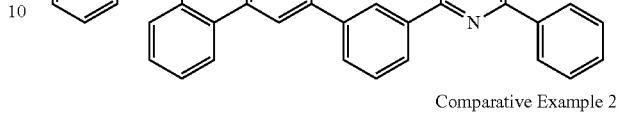

Comparative Example 1

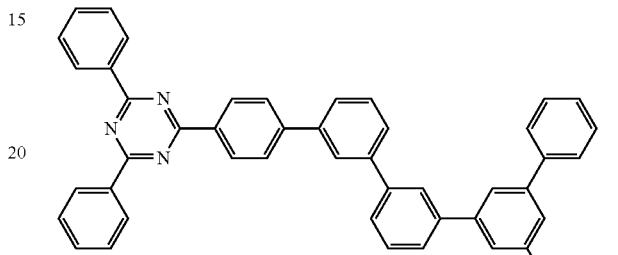

Comparative Example 2

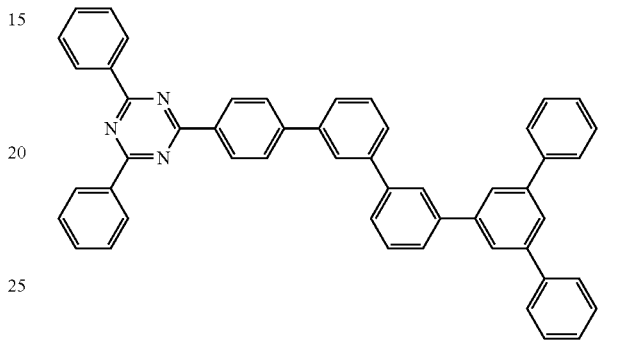

Comparative Example 3

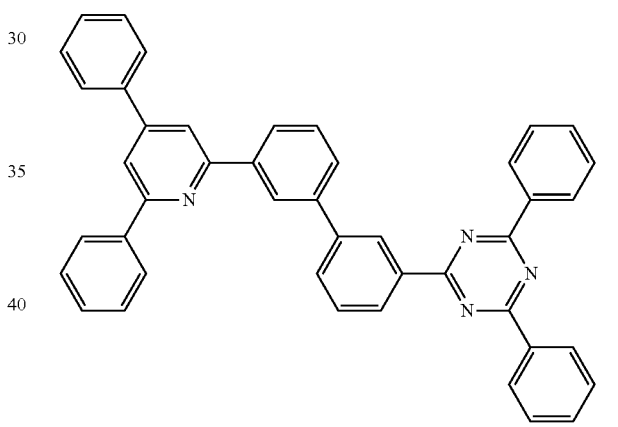

Comparative Example 4

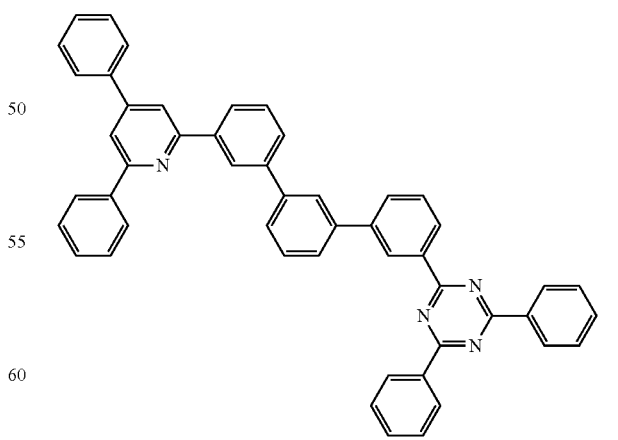

NPB, BAlq, and Ir(PPy)$_3$ used to manufacture the organic light emitting diodes respectively have the following structures.

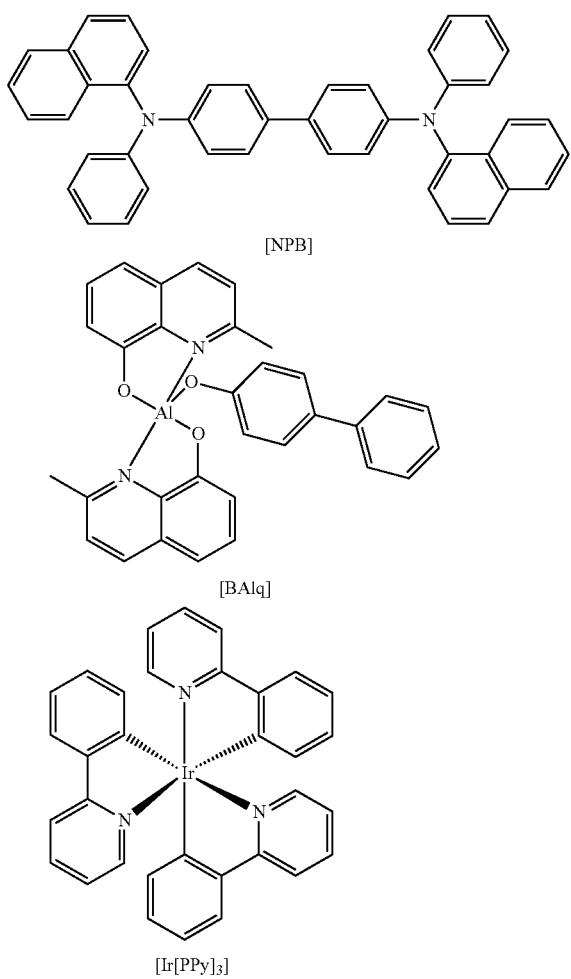

[NPB]

[BAlq]

[Ir[PPy]$_3$]

Evaluation

Current density change, luminance change, and luminous efficiency of each organic light emitting diode according to Examples 1 to 6 and Comparative Examples 1 to 4 were measured.

Specific measurement methods are as follows, and the results are shown in Table 1.

(1) Measurement of Current Density Change Depending on Voltage Change

The obtained organic light emitting diodes were measured regarding a current value flowing in the unit device, while increasing the voltage from 0 V to 10 V using a current-voltage meter (Keithley 2400), and the measured current value was divided by area to provide the results.

(2) Measurement of Luminance Change Depending on Voltage Change

Luminance was measured by using a luminance meter (Minolta Cs-1000A), while the voltage of the organic light emitting diodes was increased from 0 V to 10 V.

(3) Measurement of Luminous Efficiency

Current efficiency (cd/A) at the same current density (10 mA/cm$^2$) were calculated by using the luminance, current density, and voltages (V) from the items (1) and (2).

(4) Measurement of Life-Span

A life span was obtained by measuring a time when current efficiency (cd/A) was decreased down to 90%, while luminance (cd/m$^2$) was maintained to be 5000 cd/m$^2$.

TABLE 1

| Compounds | | Color (EL color) | Efficiency (cd/A) | T90 life-span (h) at 3000 cd/m$^2$ |
|---|---|---|---|---|
| Example 1 | Compound 1 | (0.35, 0.62) | 41 | 71 |
| Example 2 | Compound 2 | (0.38, 0.59) | 35 | 80 |
| Example 3 | Compound 3 | (0.37, 0.57) | 38 | 75 |
| Example 4 | Compound 100 | (0.37, 0.58) | 40 | 77 |
| Example 5 | Compound 4 | (0.39, 0.58) | 37 | 75 |
| Example 6 | Compound 16 | (0.39, 0.58) | 40 | 77 |
| Comparative Example 1 | Comparative Example 1 | (0.38, 0.60) | 33 | 17 |
| Comparative Example 2 | Comparative Example 2 | (0.38, 0.59) | 22 | 20 |
| Comparative Example 3 | Comparative Example 3 | (0.38, 0.60) | 32 | 21 |
| Comparative Example 4 | Comparative Example 4 | (0.38, 0.59) | 30 | 17 |

Referring to Table 1, when the compounds for an organic optoelectric device according to Examples as a dimer-shaped or ditriazine-shaped material having triazinyl groups bonded at both sides of two or more phenyl linkers linked at a meta position has two or more linking groups linked at the meta position compared with at a para position, the compounds may maintain charge mobility, reduce crystallinity, show improved processibility during deposition and solution processes for manufacturing a device, and maintain a long life-span due to an effect of suppressing life-span deterioration of the device by the crystallinity.

In addition, since the triazinyl group is included as a dimer-shape with a linker in a center, an effect of stabilizing a charge may be increased when electrons are injected, mobility of the electrons may be increased, and thus high efficiency relative to a driving voltage may be obtained.

While this invention has been described in connection with what is presently considered to be practical example embodiments, it is to be understood that the invention is not limited to the disclosed embodiments, but, on the contrary, is intended to cover various modifications and equivalent arrangements included within the spirit and scope of the appended claims. Therefore, the aforementioned embodiments should be understood to be exemplary but not limiting the present invention in any way.

DESCRIPTION OF SYMBOLS

10: anode
20: cathode
30: organic layer
31: hole transport layer
32: light emitting layer
33: hole transport auxiliary layer
34: electron transport layer
35: electron transport auxiliary layer
36: electron injection layer
37: hole injection layer

The invention claimed is:

1. A compound for an organic optoelectric device represented by Chemical Formula I:

[Chemical Formula I]

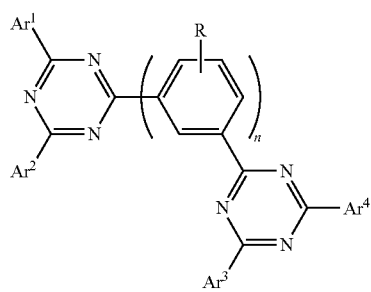

wherein, in Chemical Formula I, $Ar^1$ to $Ar^4$ are independently a substituted or unsubstituted C6 to C30 aryl group, R is independently hydrogen, deuterium, a substituted or unsubstituted C1 to C30 alkyl group, a substituted or unsubstituted C3 to C30 cycloalkyl group, a substituted or unsubstituted C6 to C30 aryl group, a substituted or unsubstituted C1 to C30 alkoxy group, a substituted or unsubstituted C3 to C40 silyl group, or a combination thereof, each of R is the same or different, n is an integer of 2 to 10, and wherein "substituted" refers to replacement of at least one hydrogen by deuterium, a cyano group, a nitro group, a halogen-substituted C1 to C10 alkyl group, a C1 to C40 silyl group, a C1 to C30 alkyl group, a C1 to C10 alkylsilyl group, a C6 to C30 arylsilyl group, a C3 to C30 cycloalkyl group, a C2 to C30 heterocycloalkyl group, a C6 to C30 aryl group, or a C1 to C20 alkoxy group.

2. The compound for an organic optoelectric device of claim 1, wherein n is an integer of 2 to 5.

3. The compound for an organic optoelectric device of claim 1, wherein Chemical Formula 1 is represented by one of Chemical Formulae I-1 to I-13:

[Chemical Formula I-1]

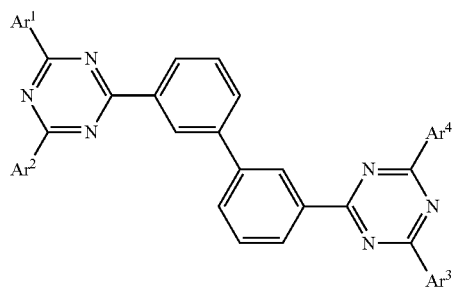

[Chemical Formula I-2]

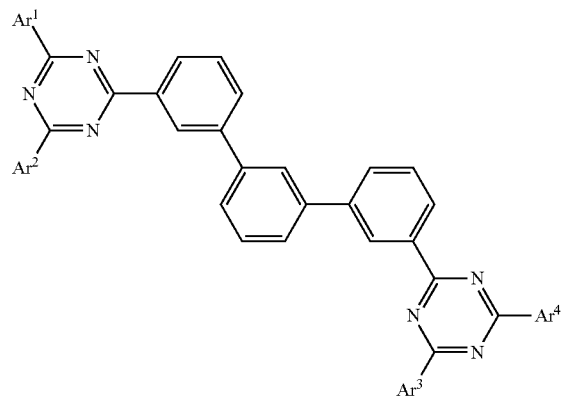

[Chemical Formula I-3]

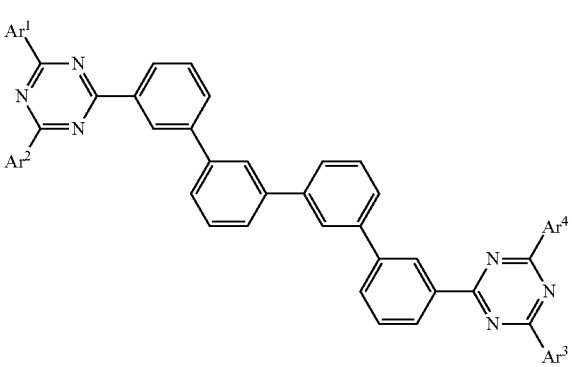

[Chemical Formula I-4]

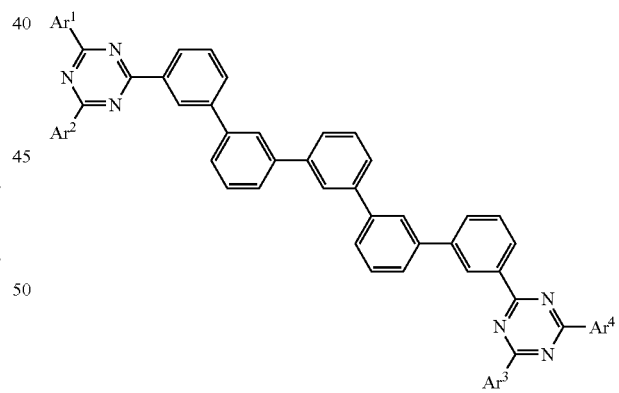

[Chemical Formula I-5]

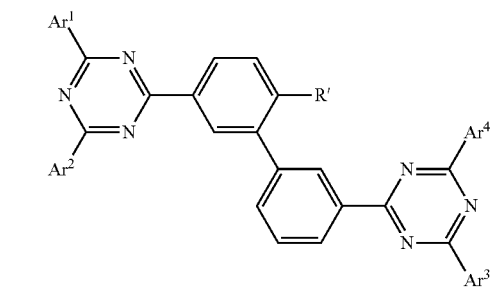

[Chemical Formula I-6]

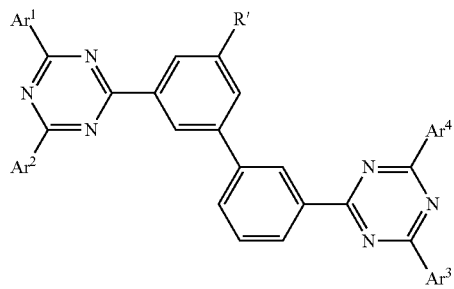

[Chemical Formula I-7]

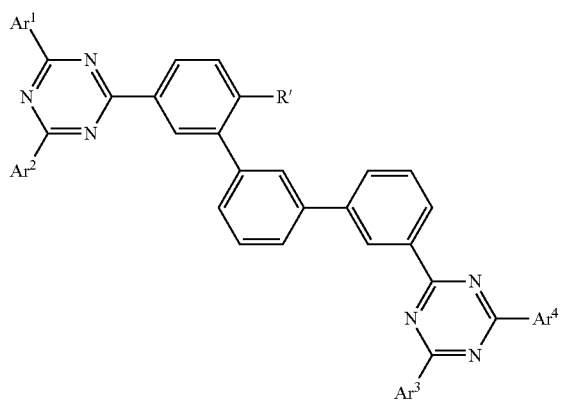

[Chemical Formula I-8]

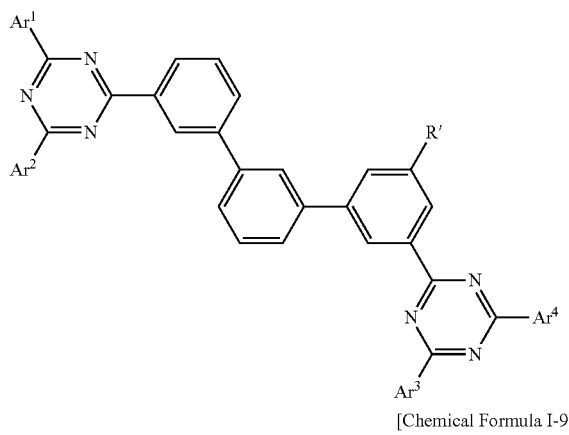

[Chemical Formula I-9]

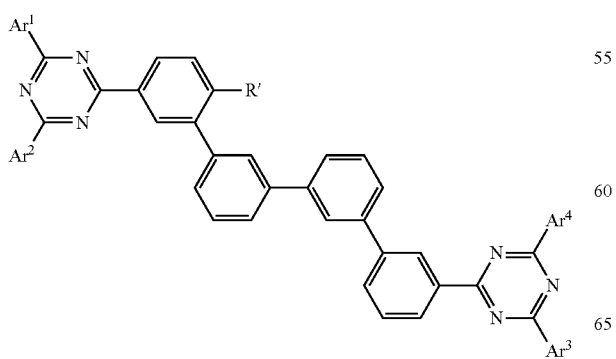

[Chemical Formula I-10]

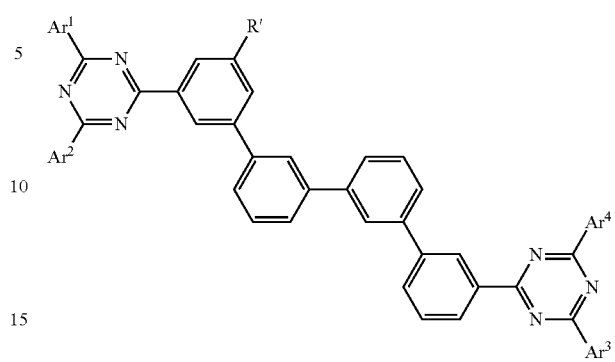

wherein, in Chemical Formulae I-1 to I-10,

Ar$^1$ to Ar$^4$ are independently a substituted or unsubstituted C6 to C30 aryl group, and R' is deuterium, a substituted or unsubstituted C1 to C10 alkyl group, or a substituted or unsubstituted C6 to C20 aryl group, wherein "substituted" is the same as defined in claim 1.

4. The compound for an organic optoelectric device of claim 1, wherein Ar$^1$ to Ar$^4$ are independently a substituted or unsubstituted phenyl group, a substituted or unsubstituted biphenyl group, a substituted or unsubstituted terphenyl group, or a substituted or unsubstituted quaterphenyl group.

5. The compound for an organic optoelectric device of claim 1, wherein Ar$^1$ to Ar$^4$ are independently selected from substituted or unsubstituted groups of Group I:

[Group I]

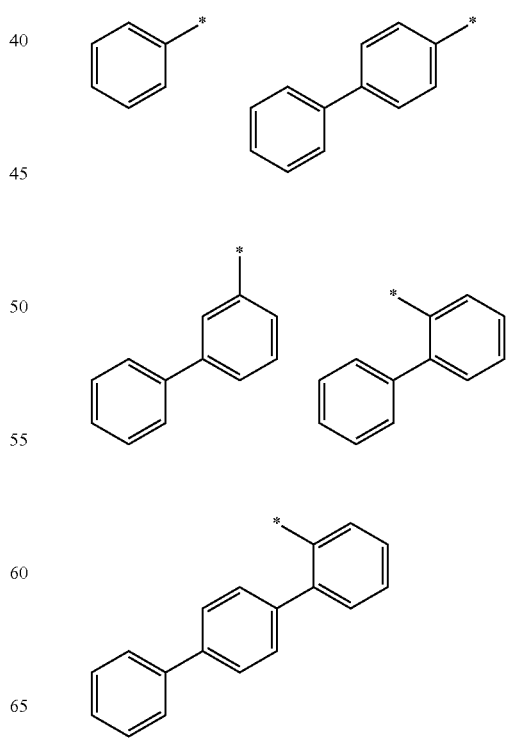

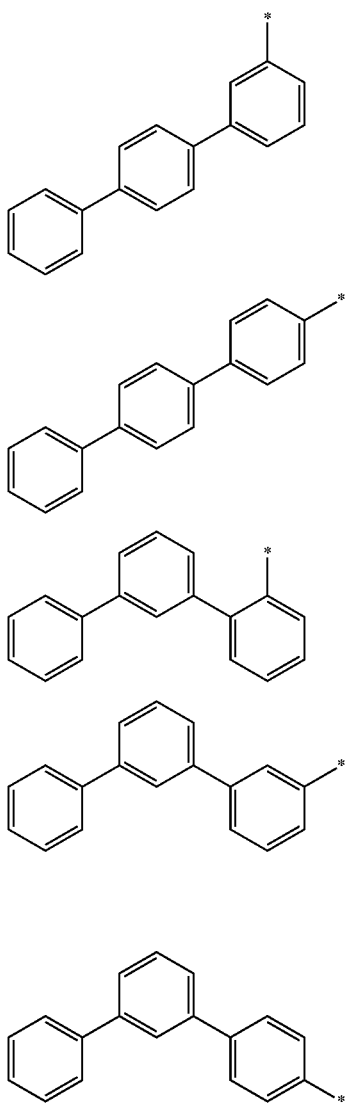
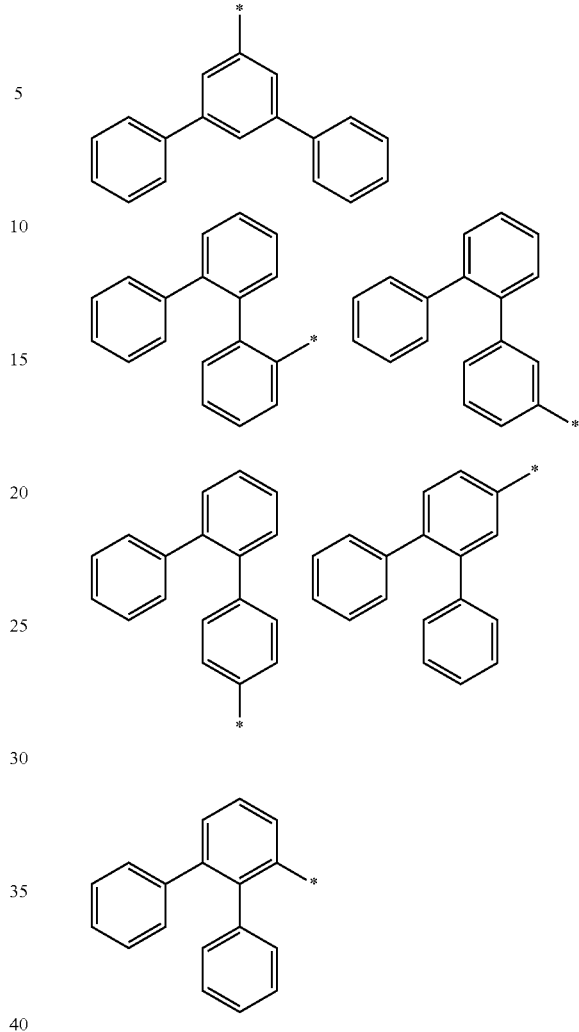
wherein, in Group I,
* indicates a binding site with an adjacent atom.
6. The compound for an organic optoelectric device of claim 1, which is one of compounds of Group II:
[Group II]
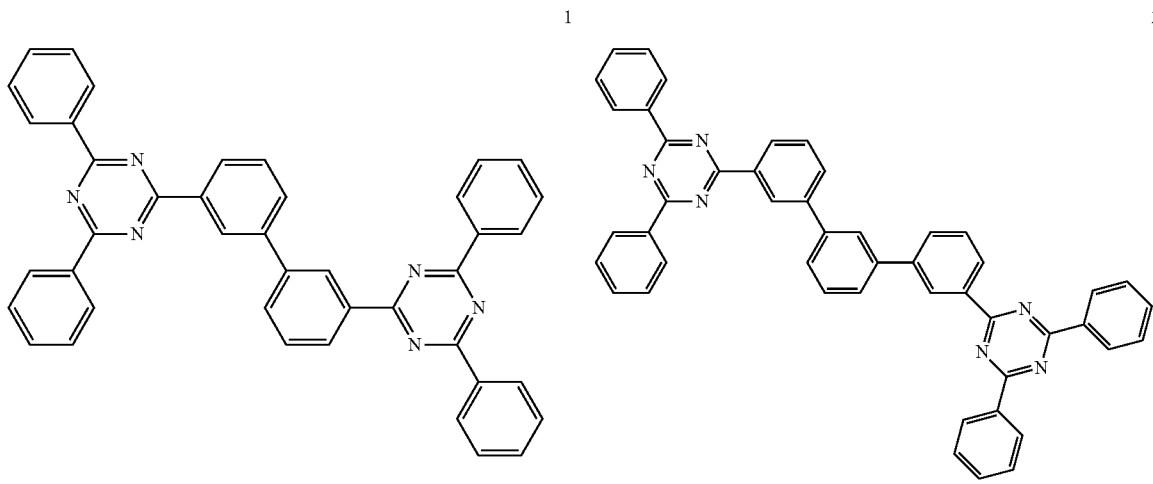

-continued
3
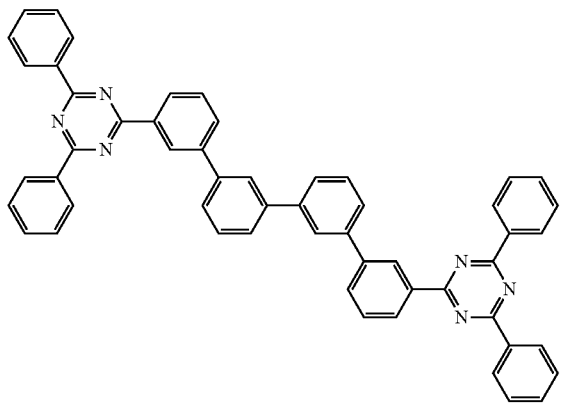
4
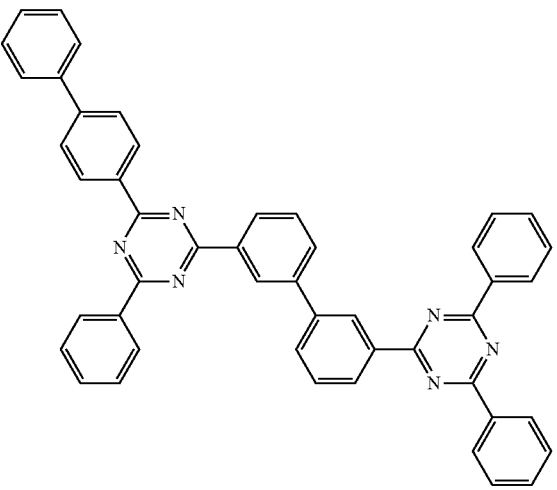
5
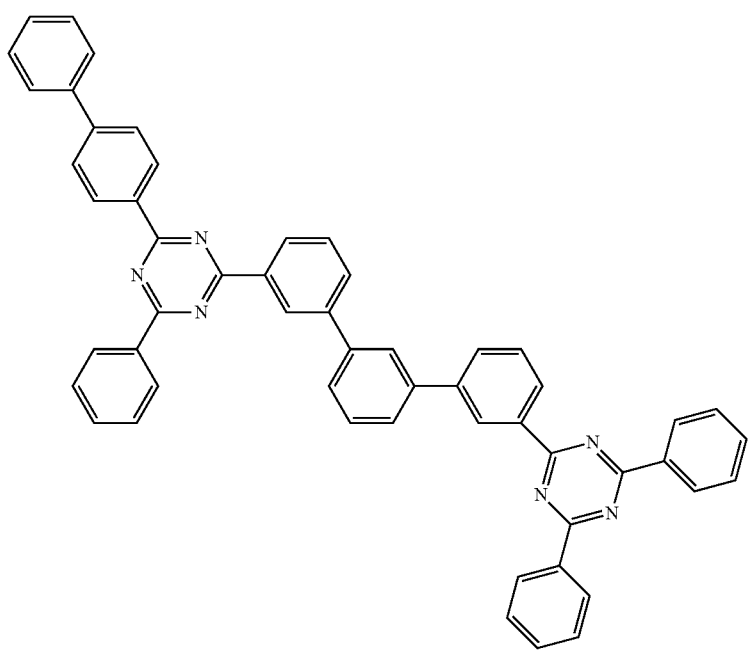

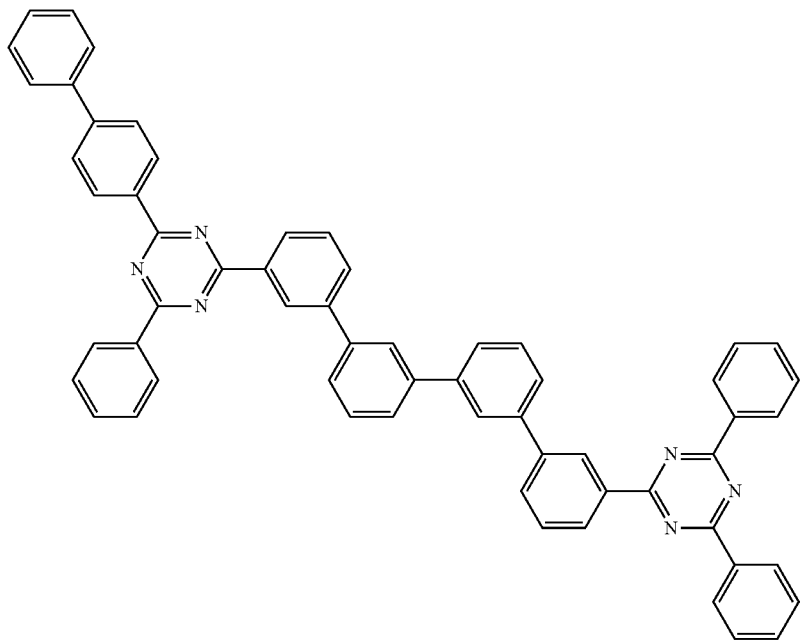
6
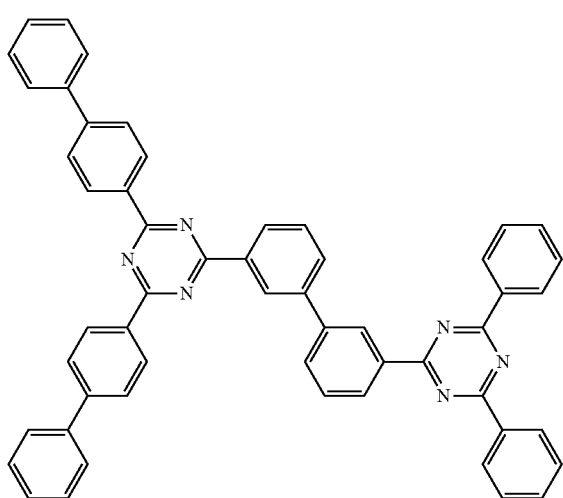
7

-continued
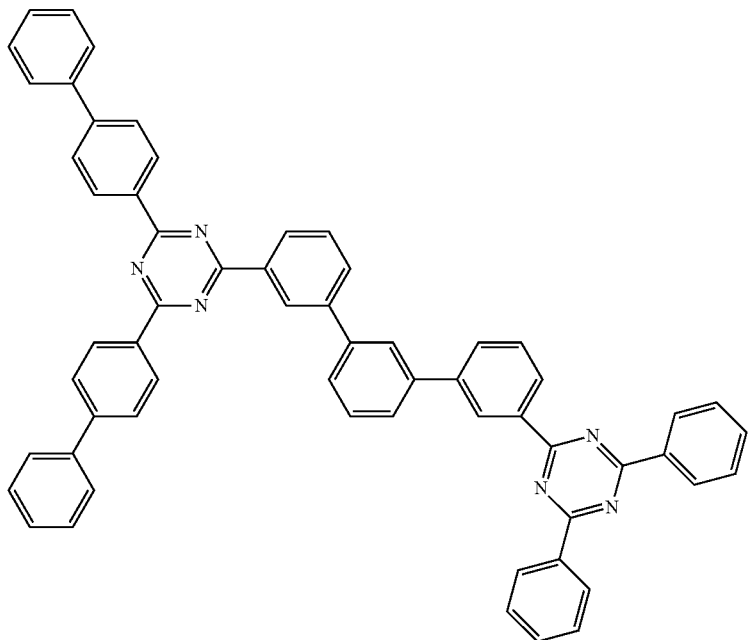
8
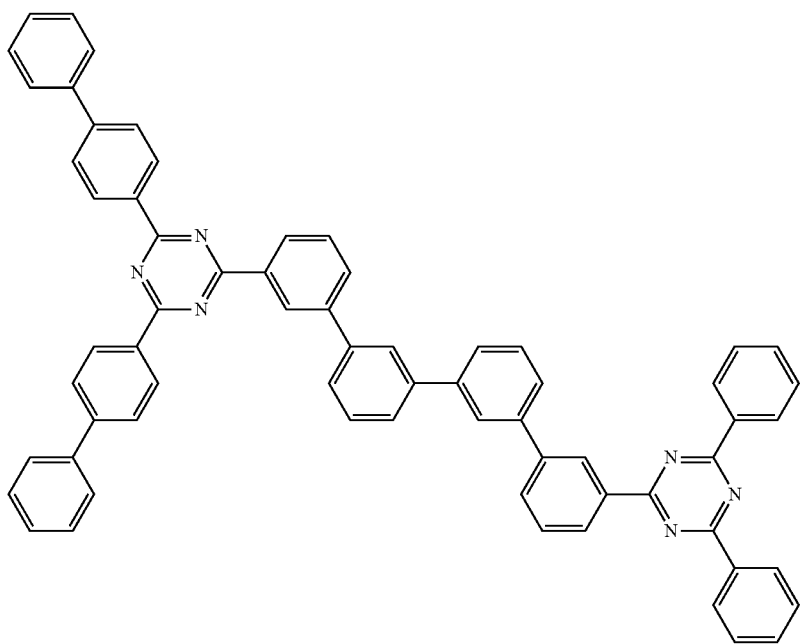
9

-continued
10
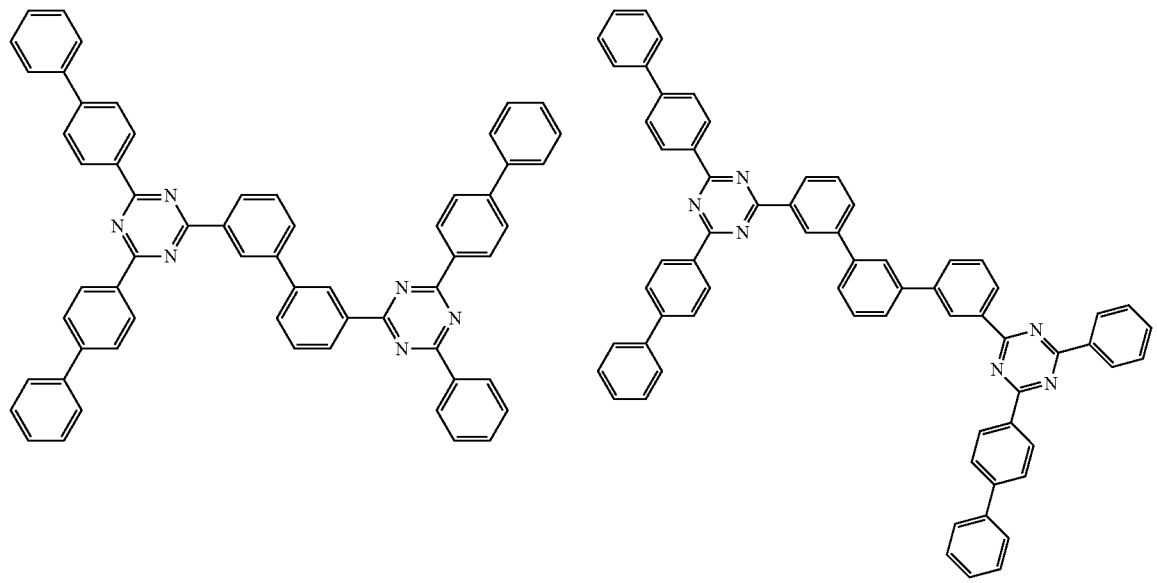
11
12
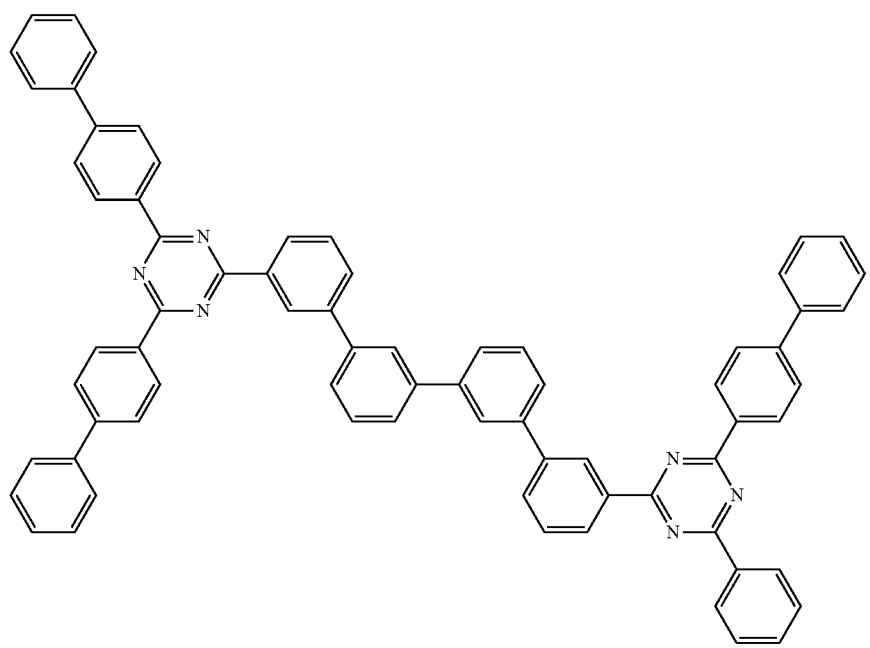

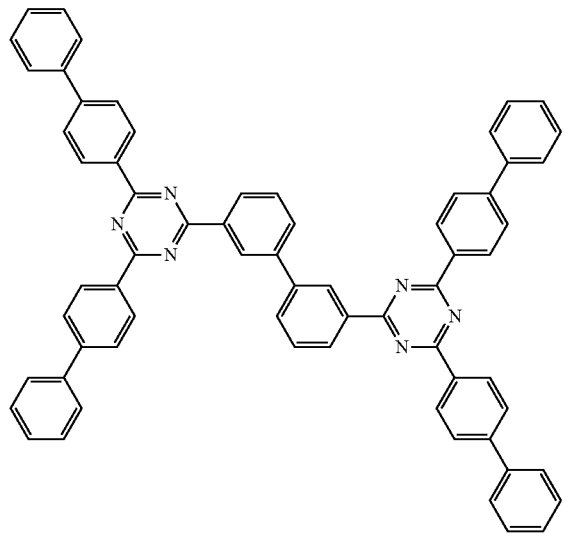
13
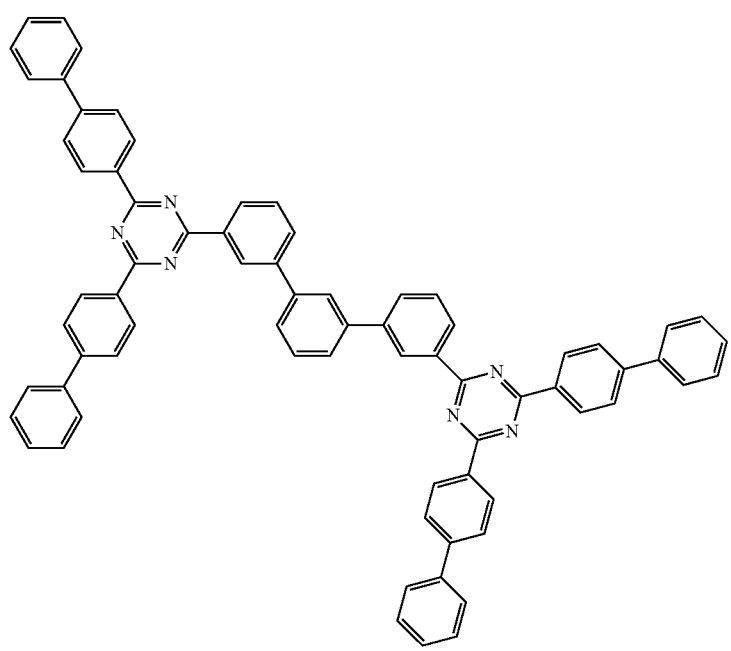
14

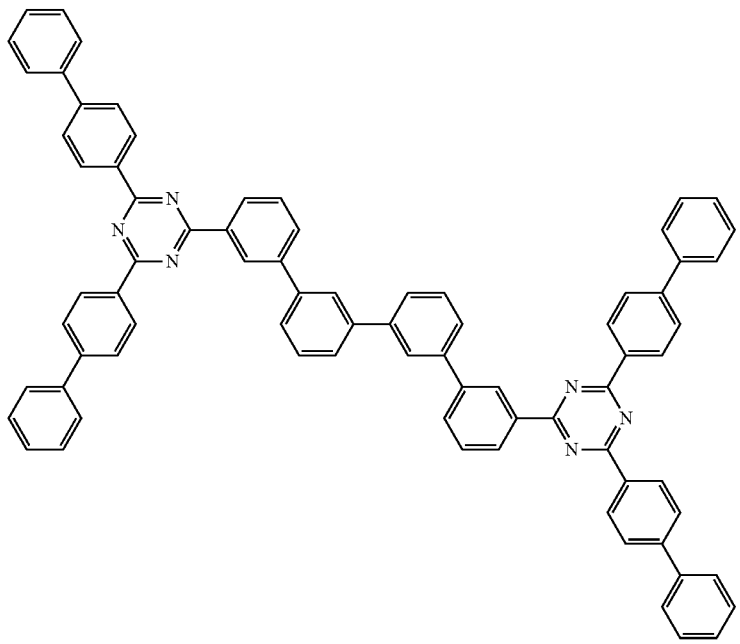
15
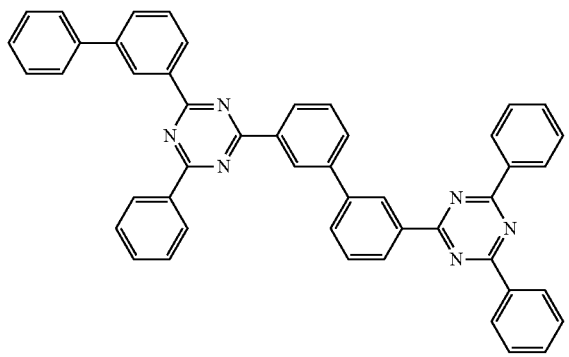
16
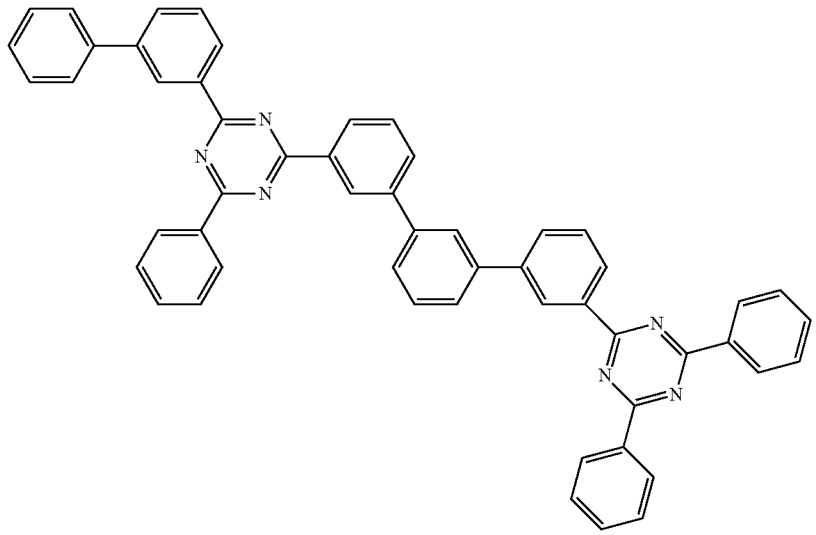
17

-continued
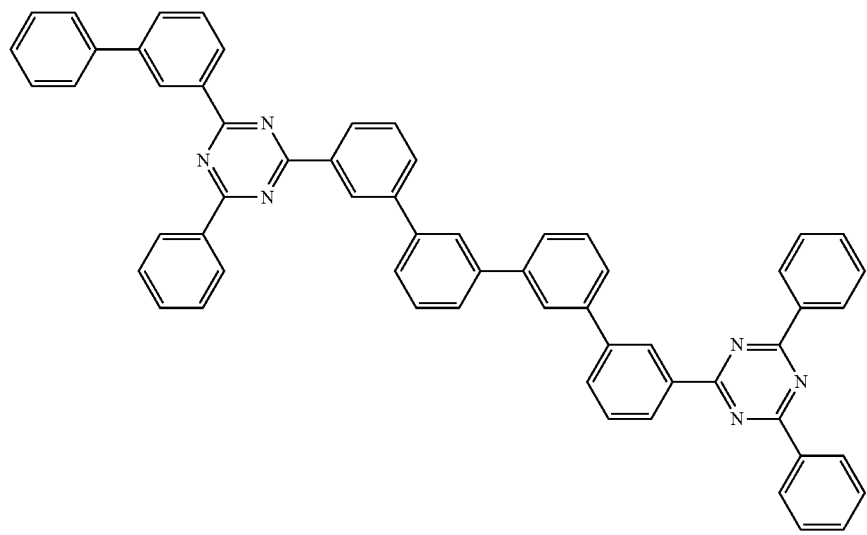
18
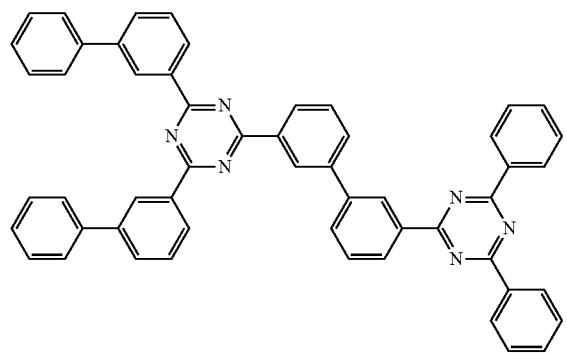
19
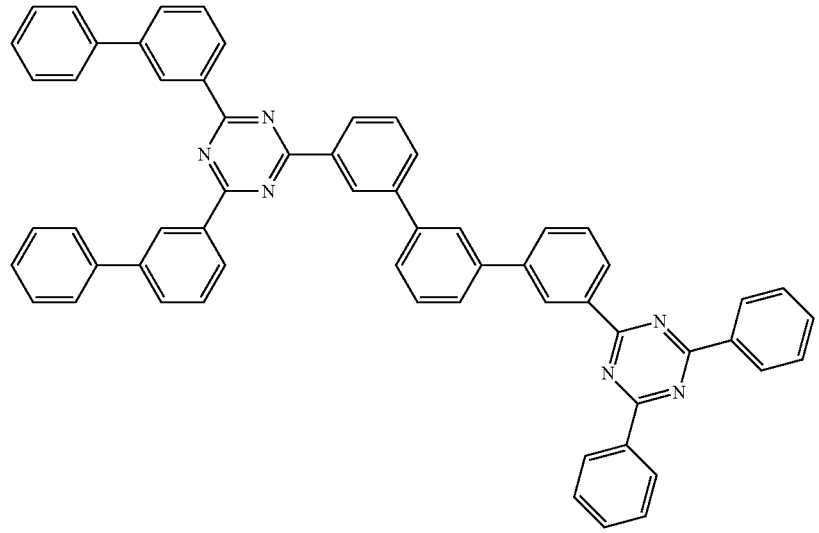
20

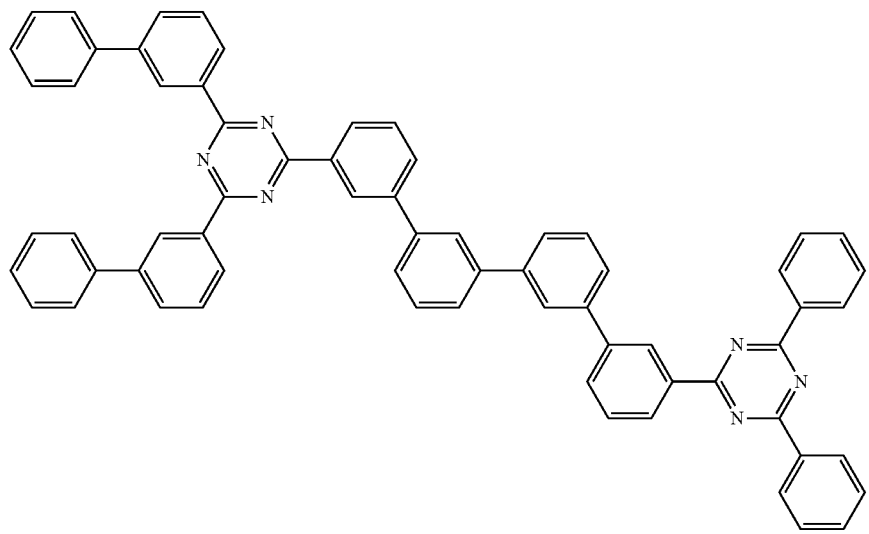
21
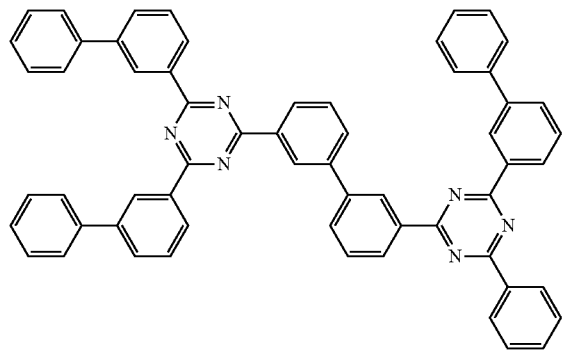
22
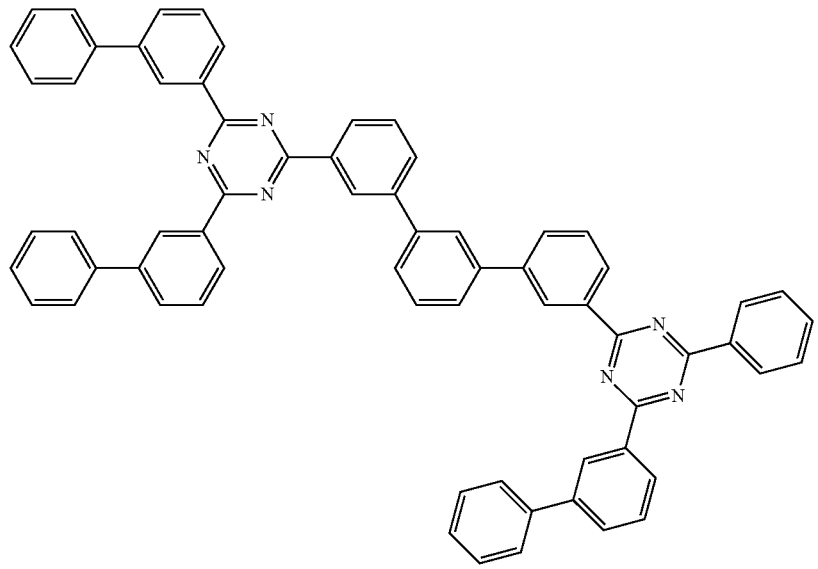
23

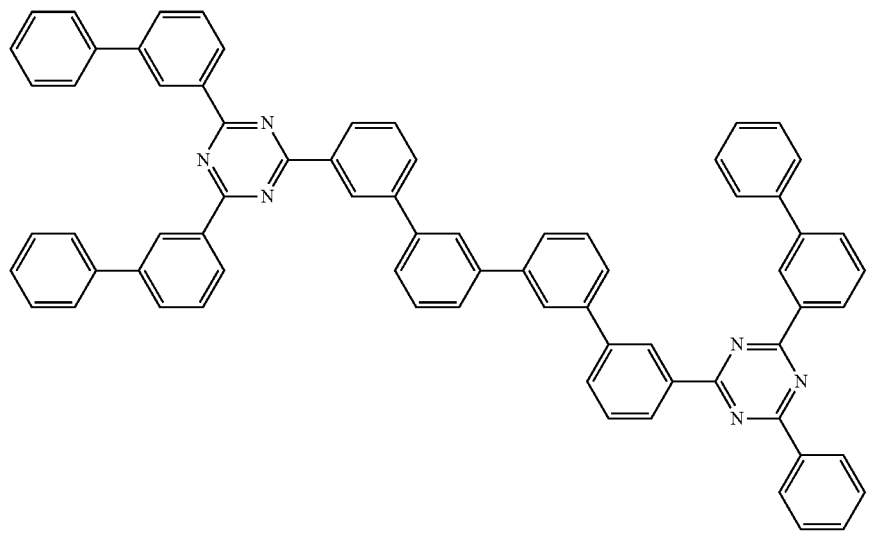
24
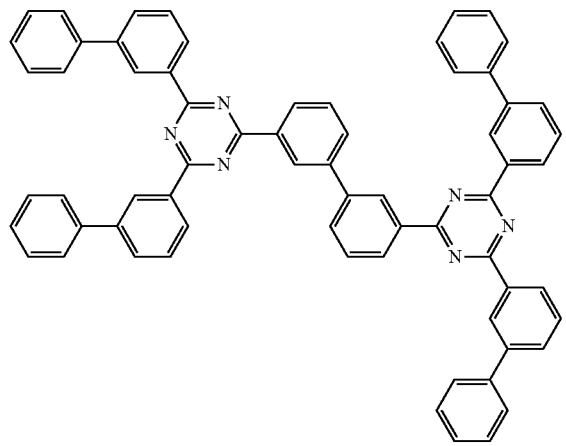
25
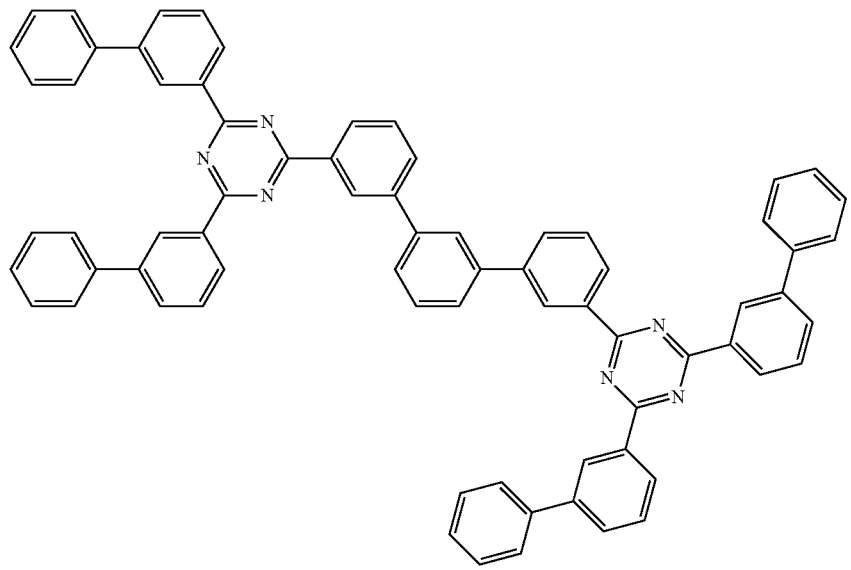
26

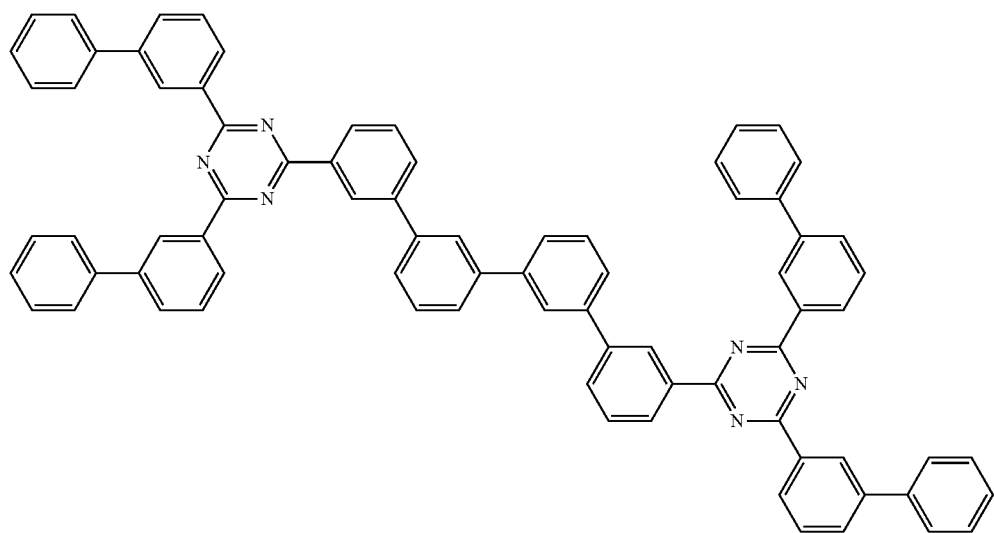
27
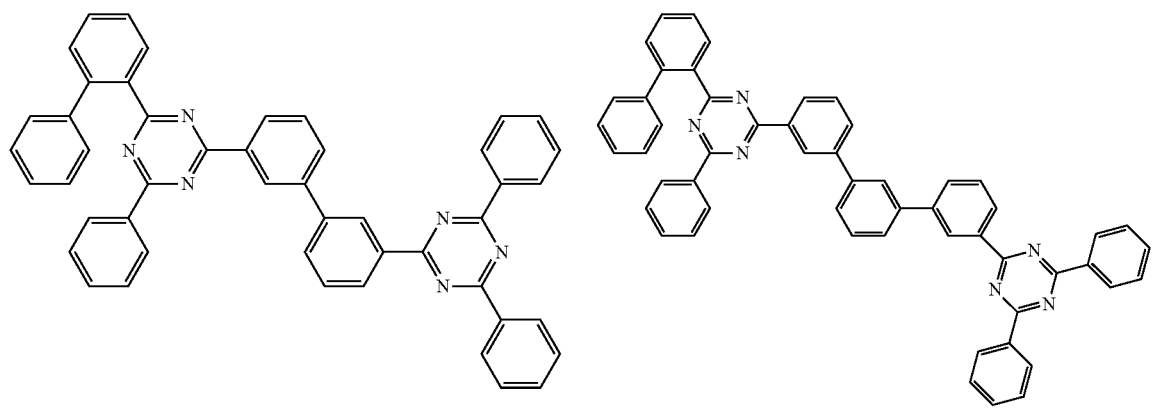
28
29
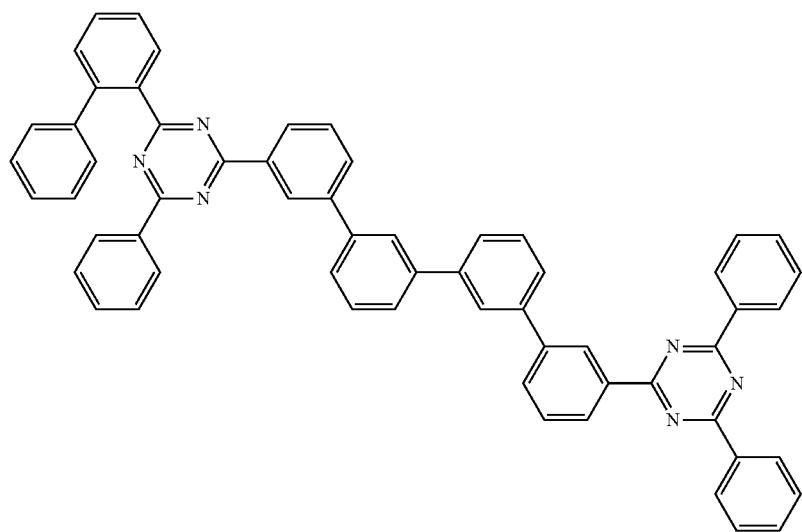
30

-continued
31
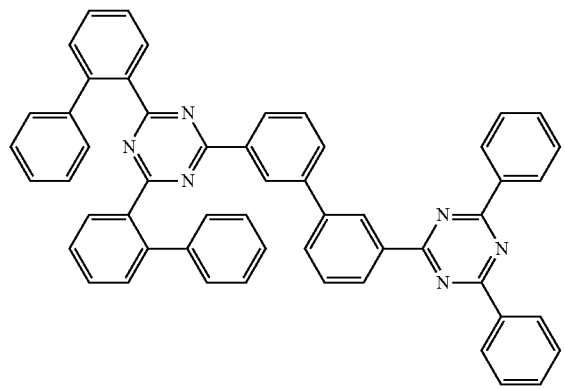
32
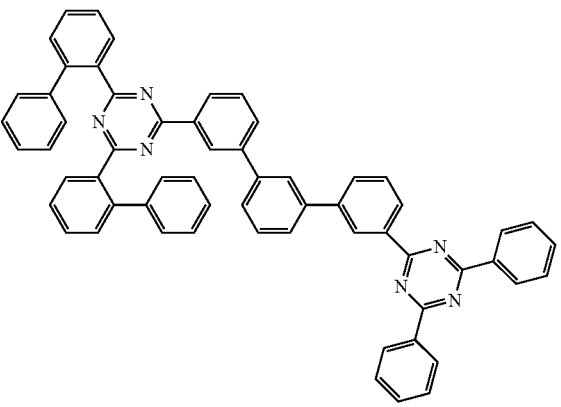
33
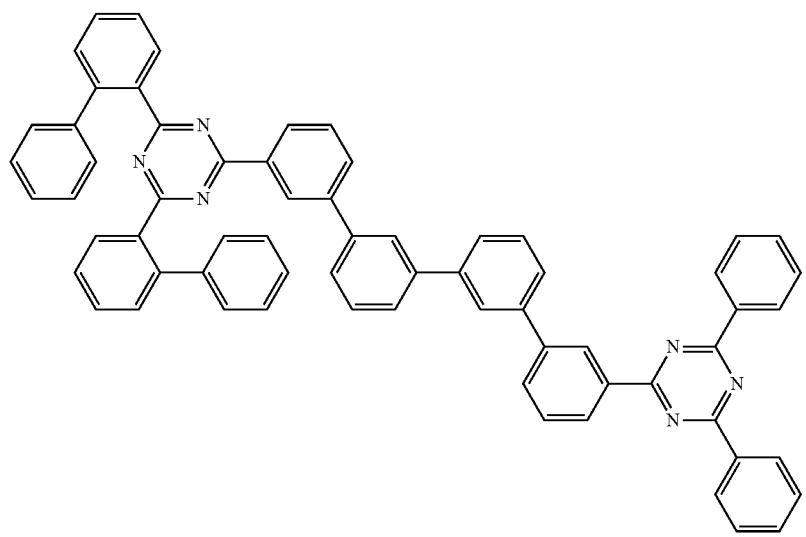
34
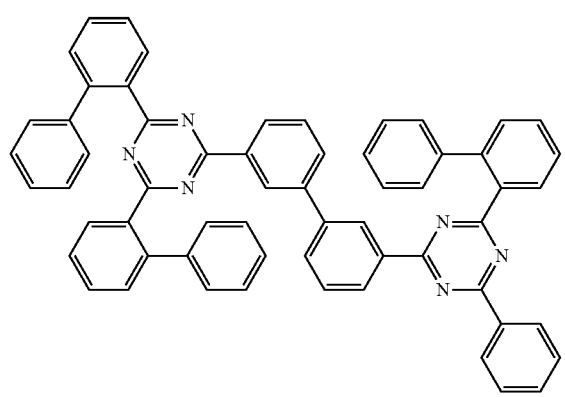
35
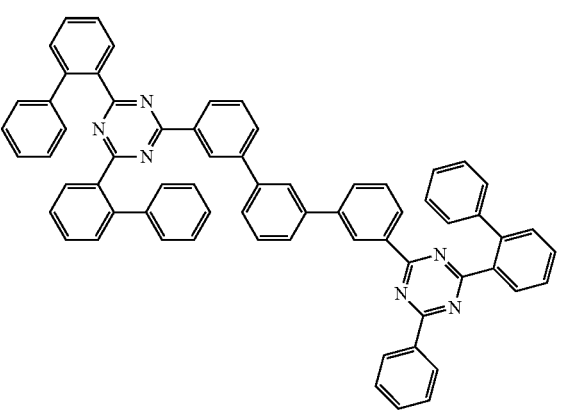

36
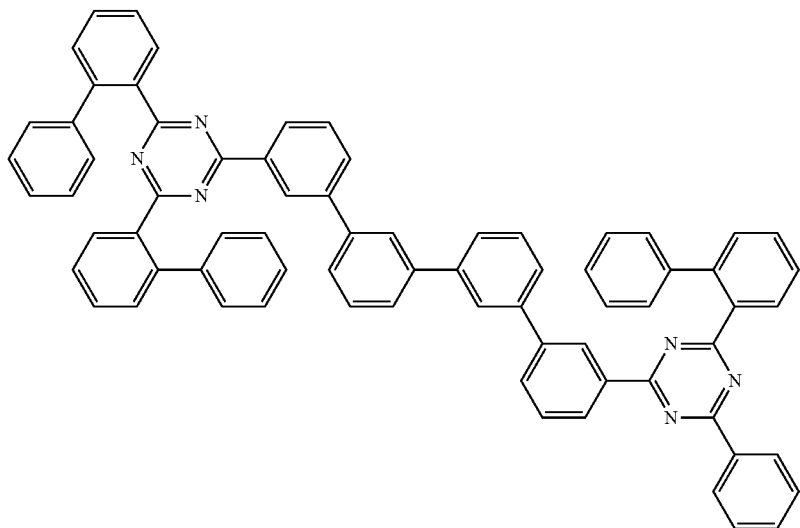
37
38
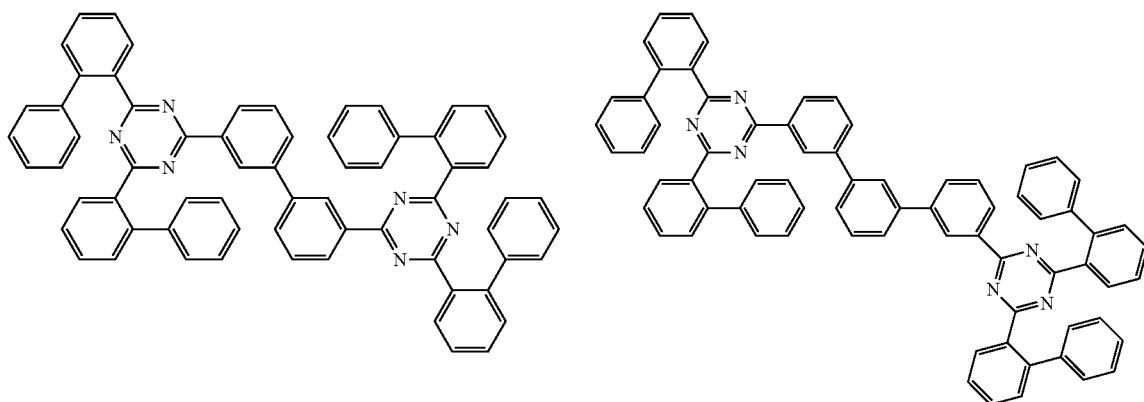
39
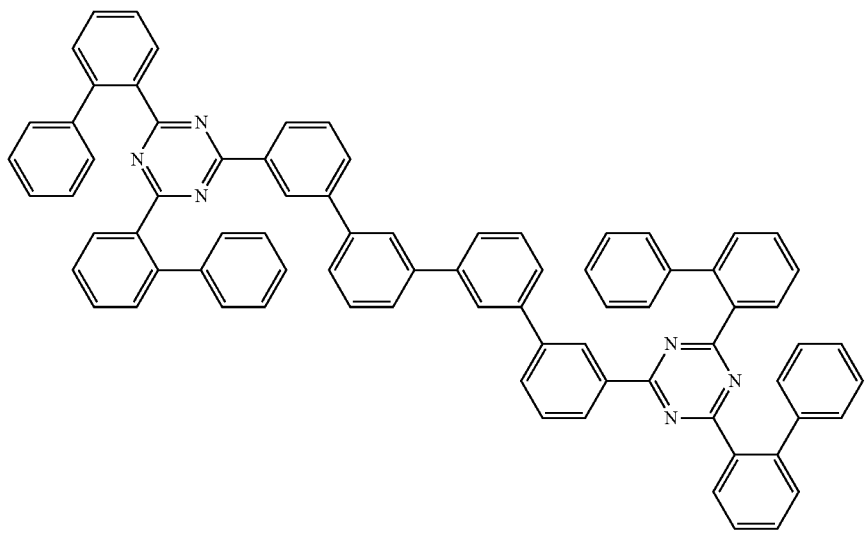

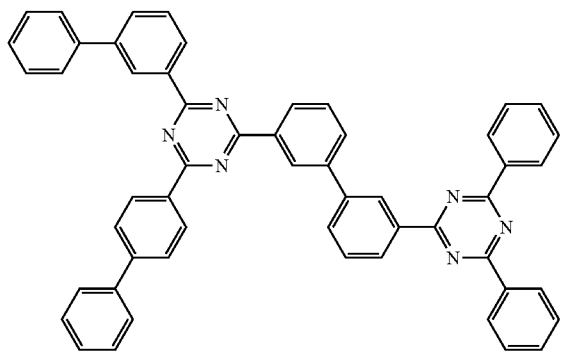
40
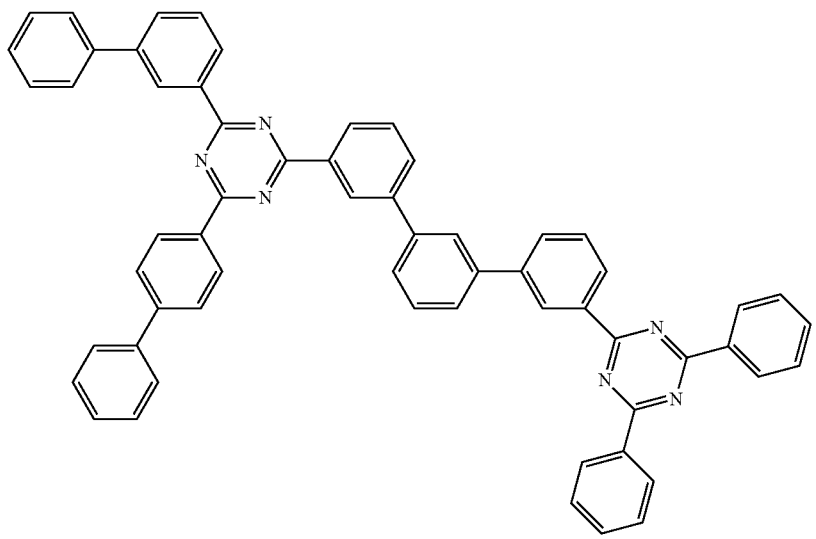
41
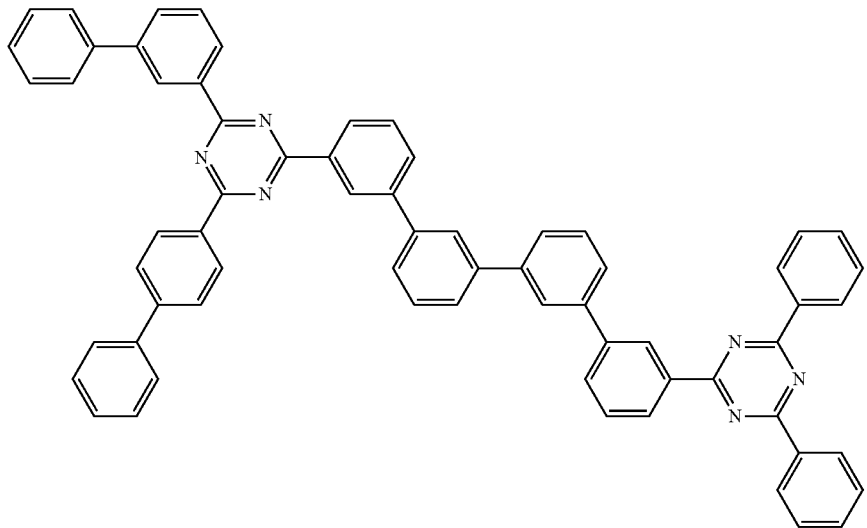
42

43
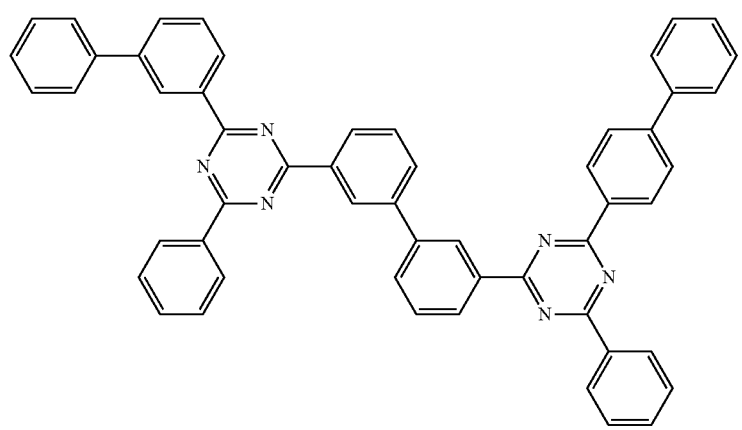
44
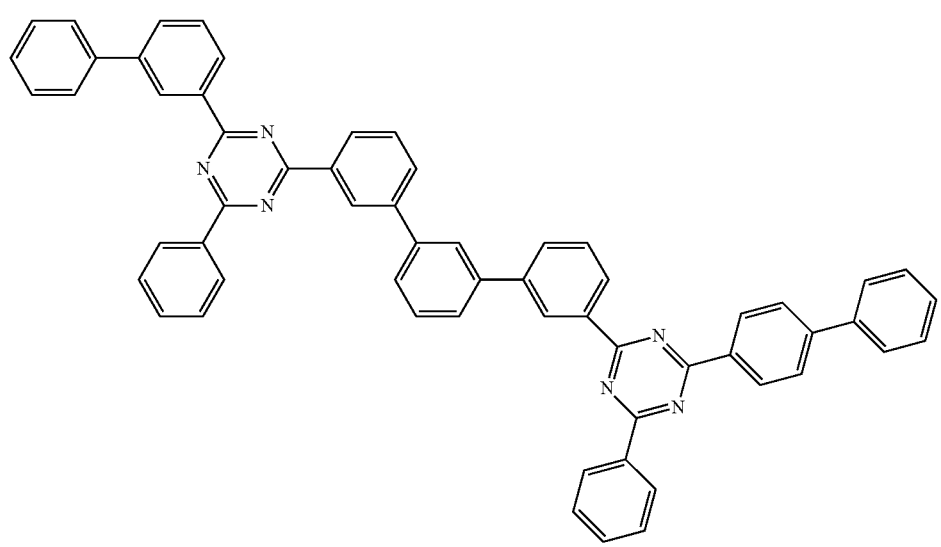
45
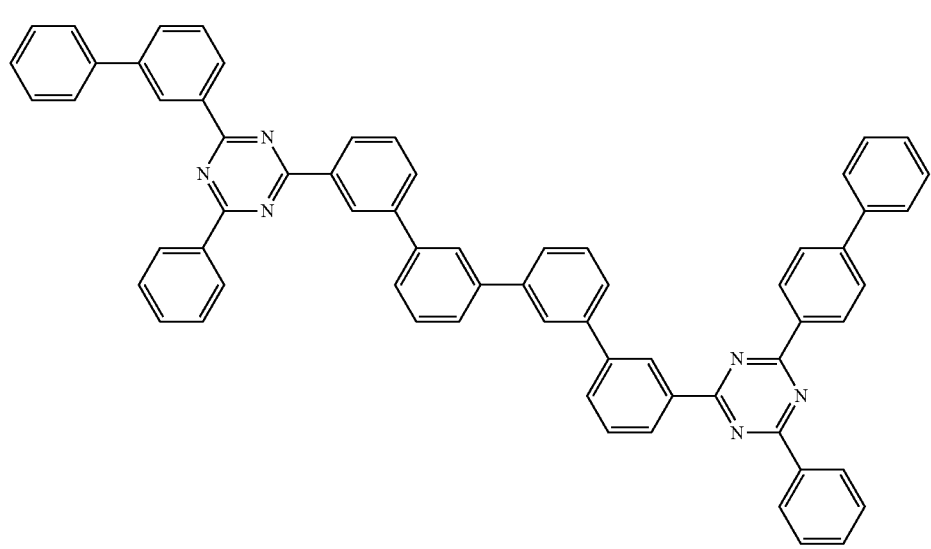

46
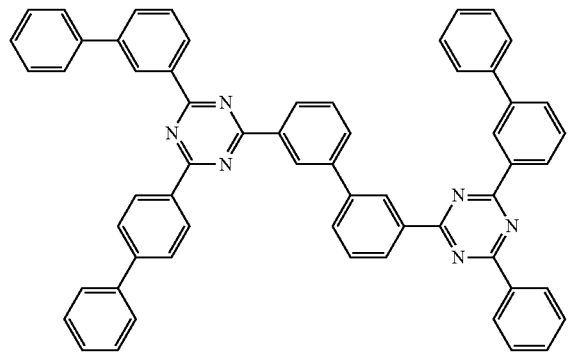
47
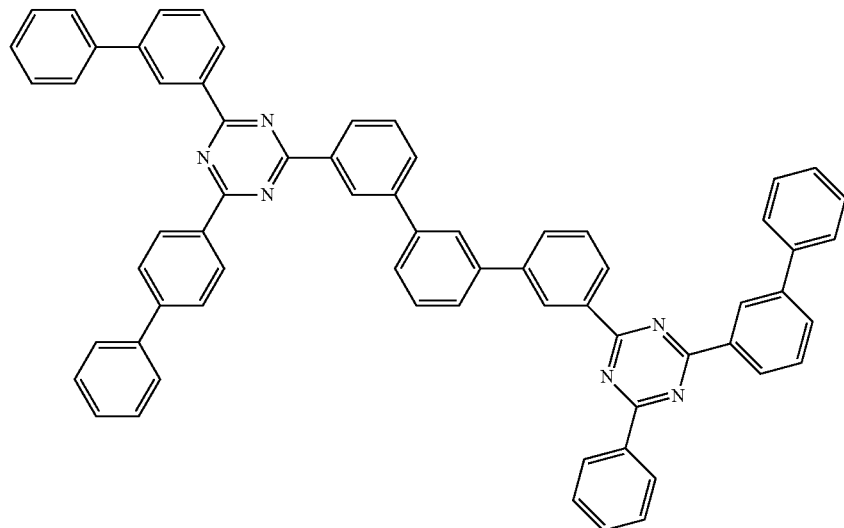
48
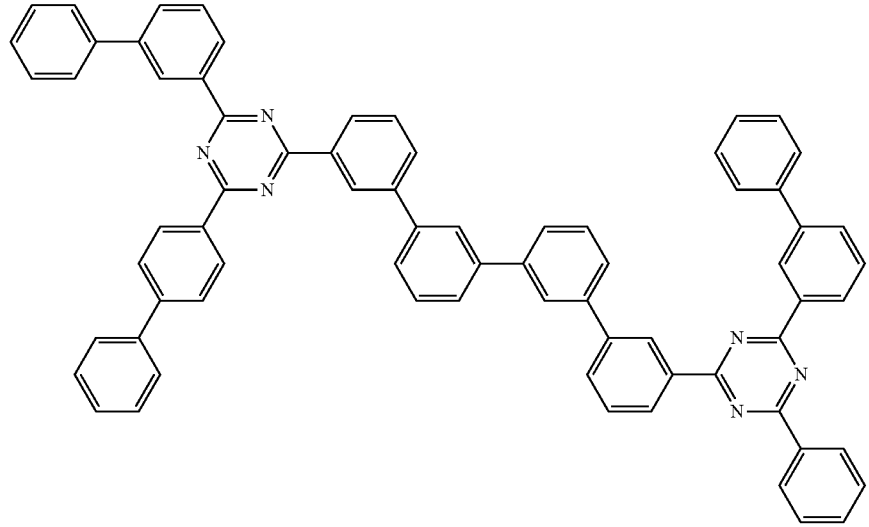

-continued
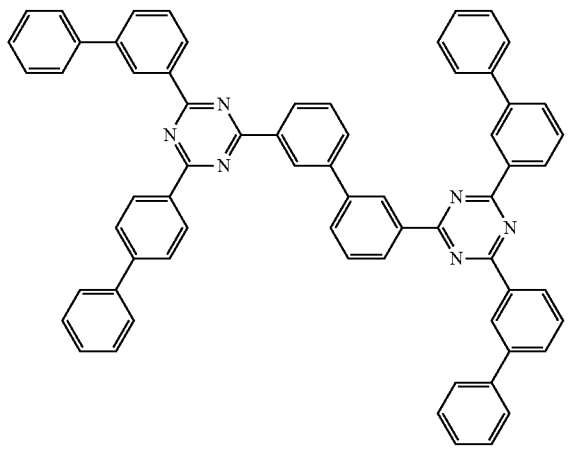
49
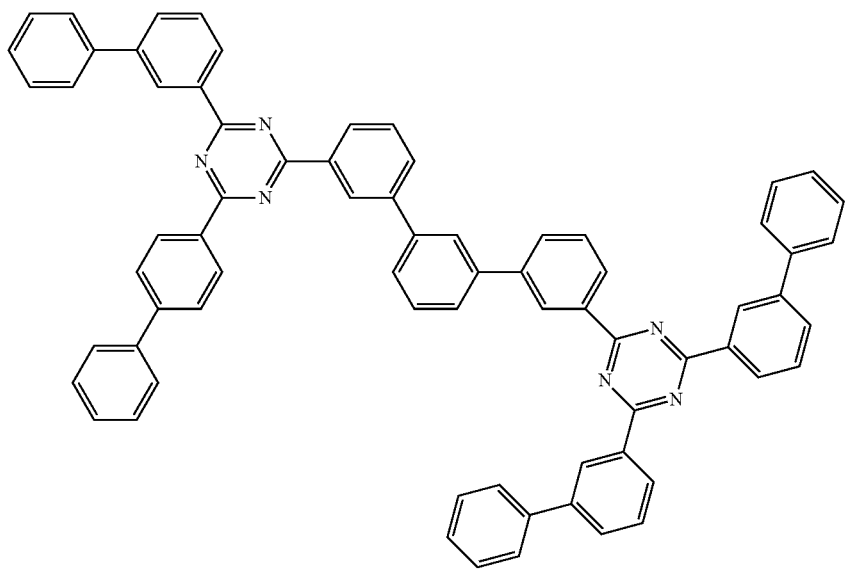
50
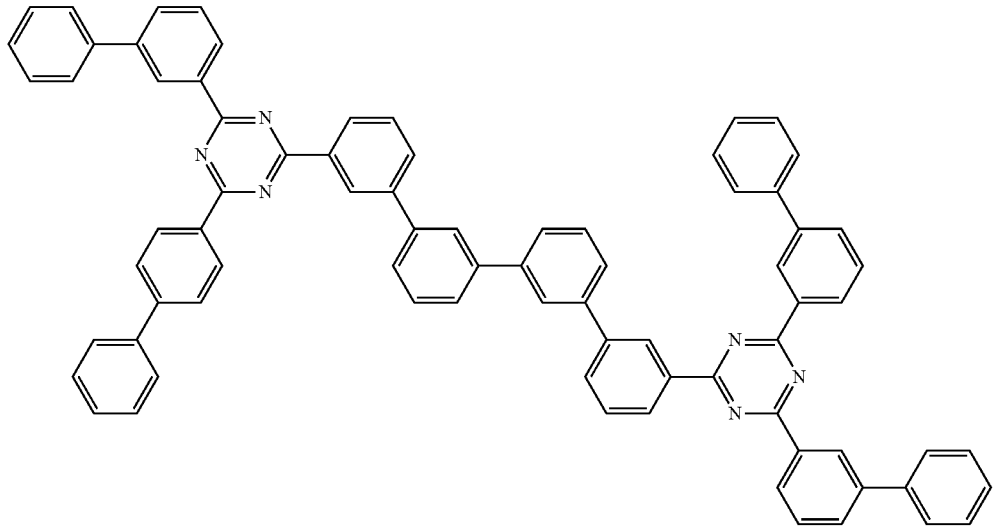
51

-continued
52
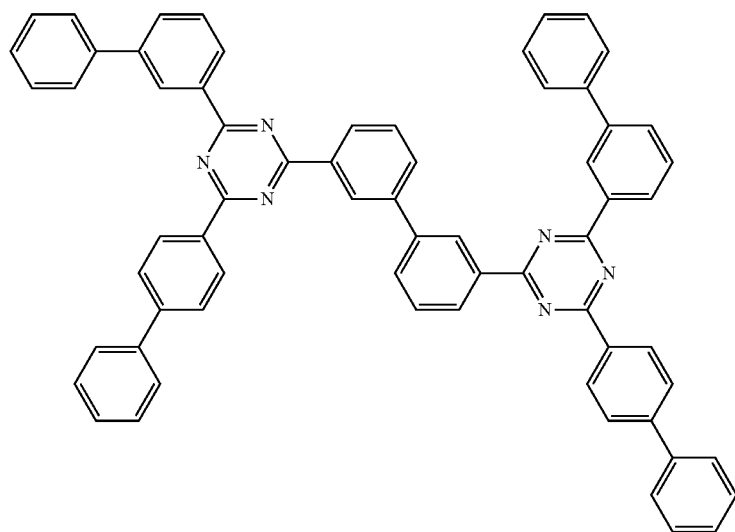
53
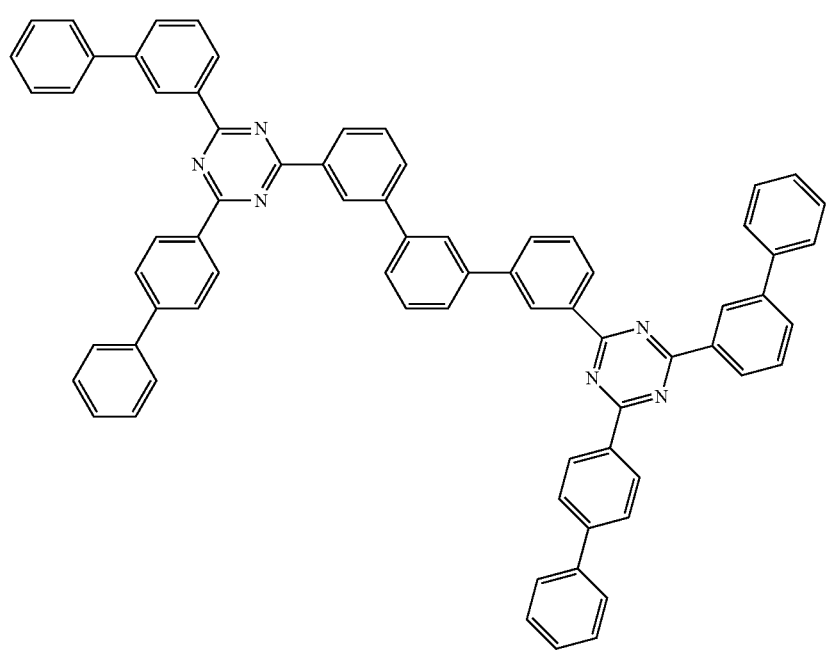

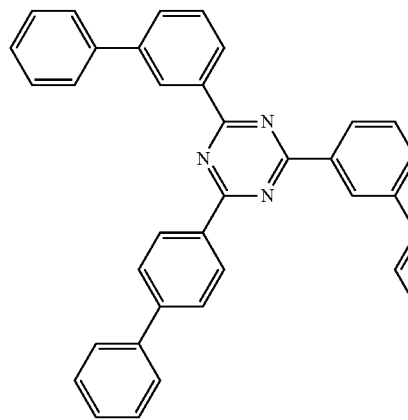
54
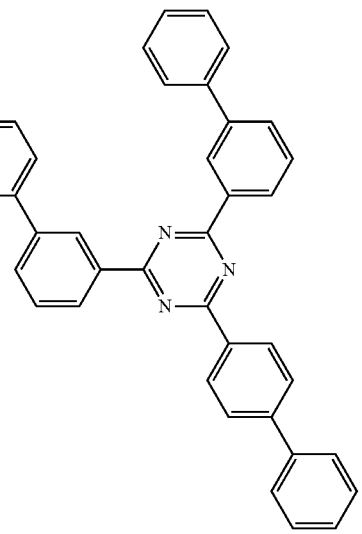
55
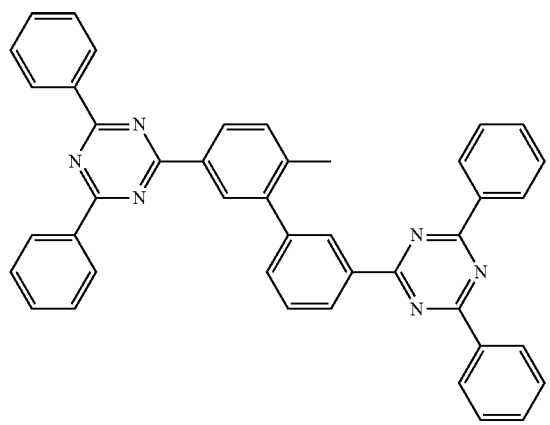
56
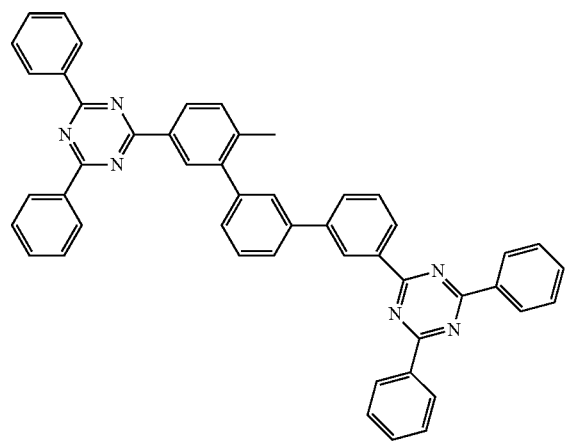
57
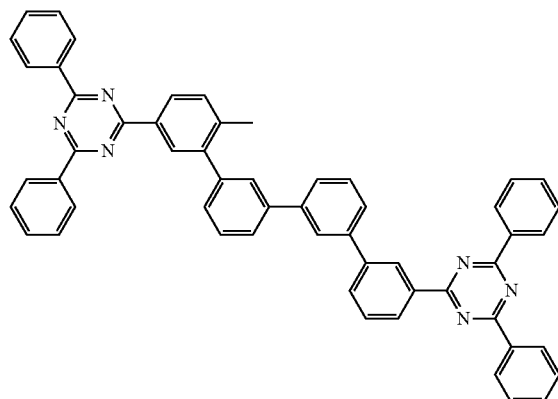
58
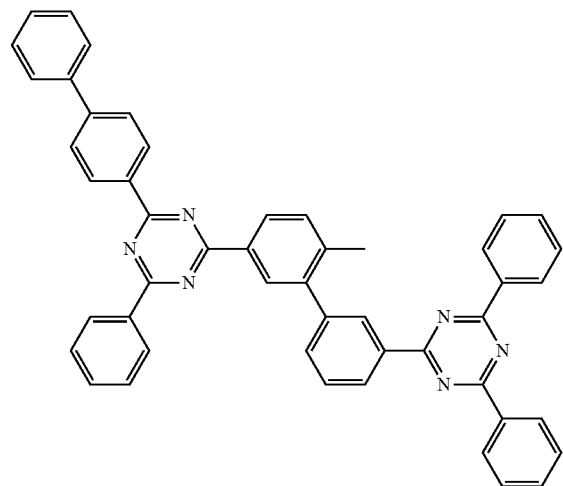

59
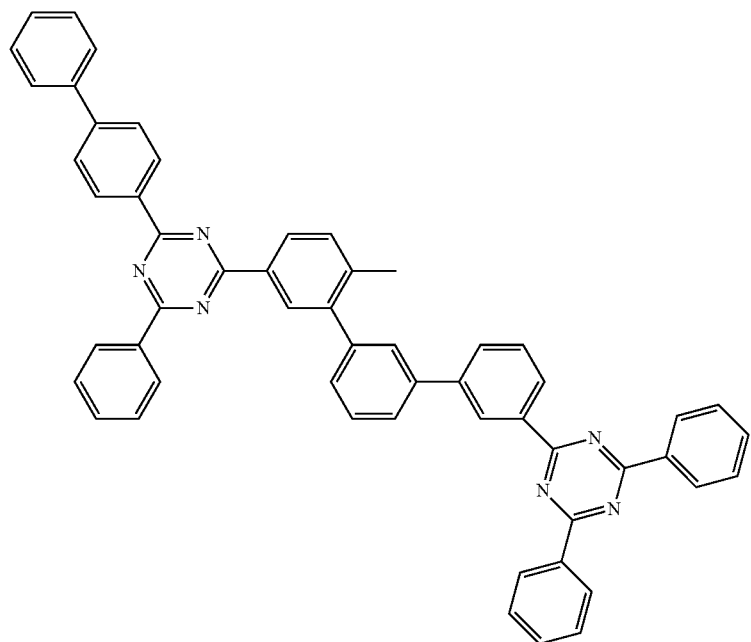
60
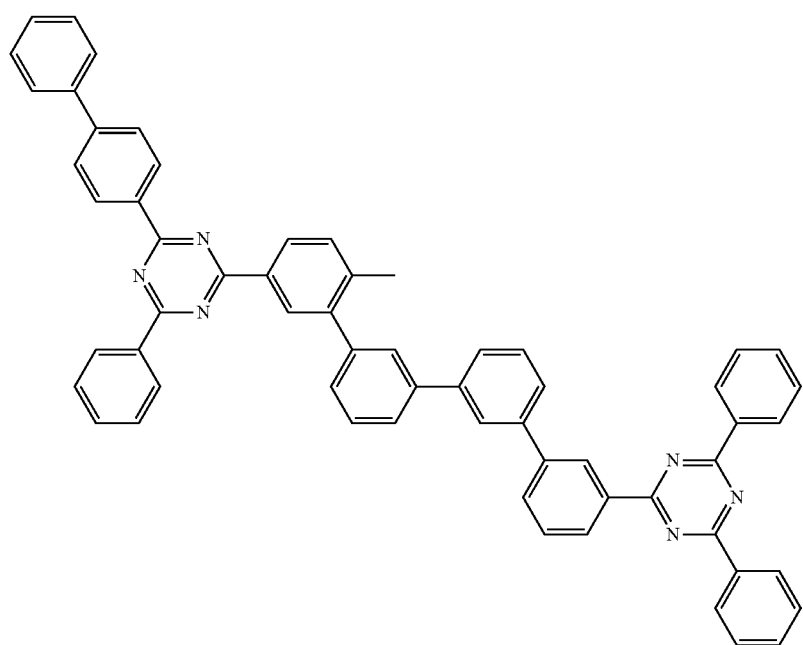
61
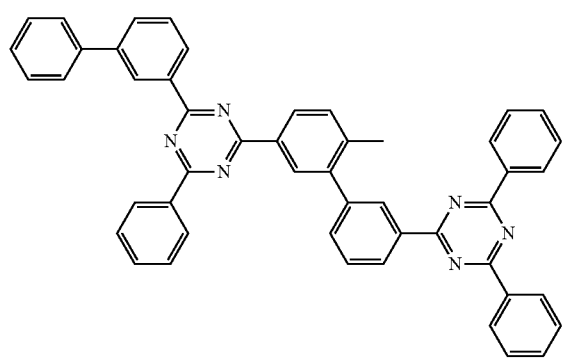

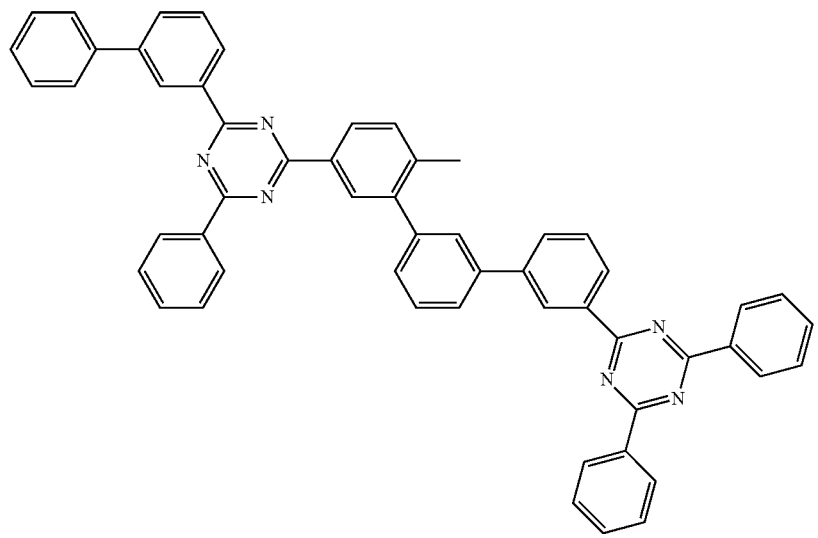
62
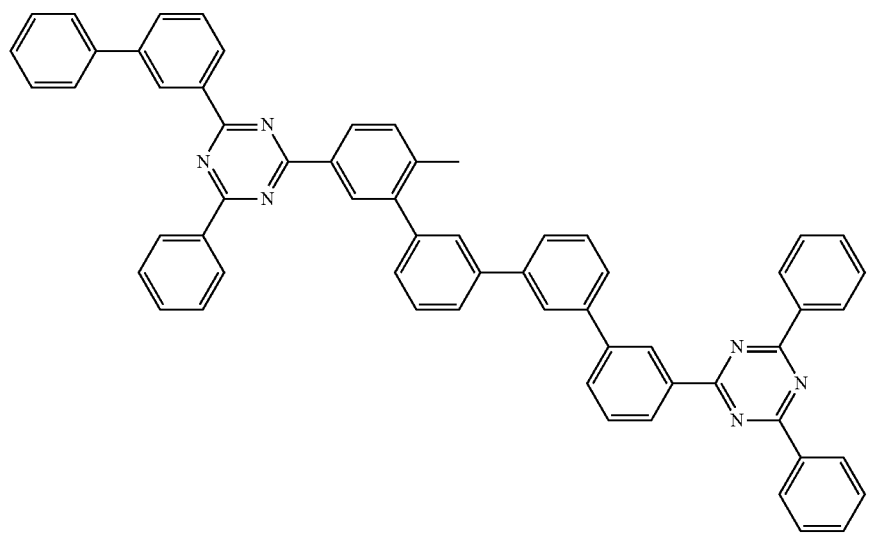
63
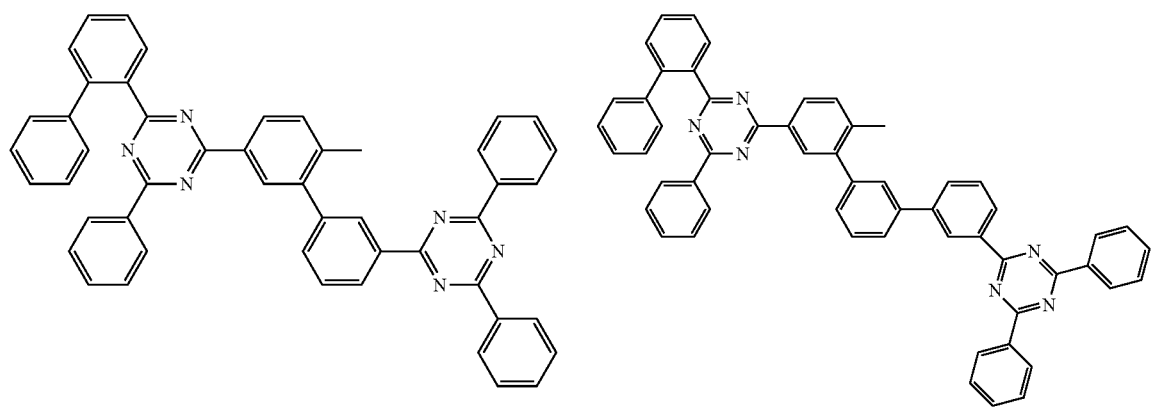

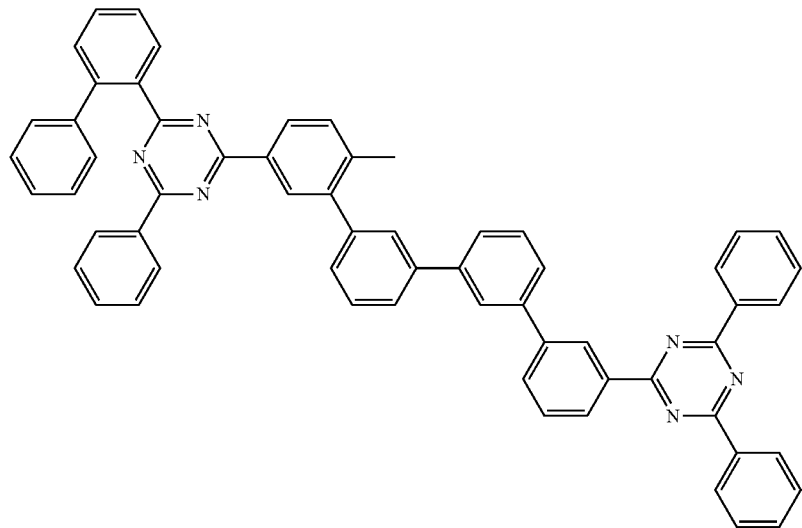
66
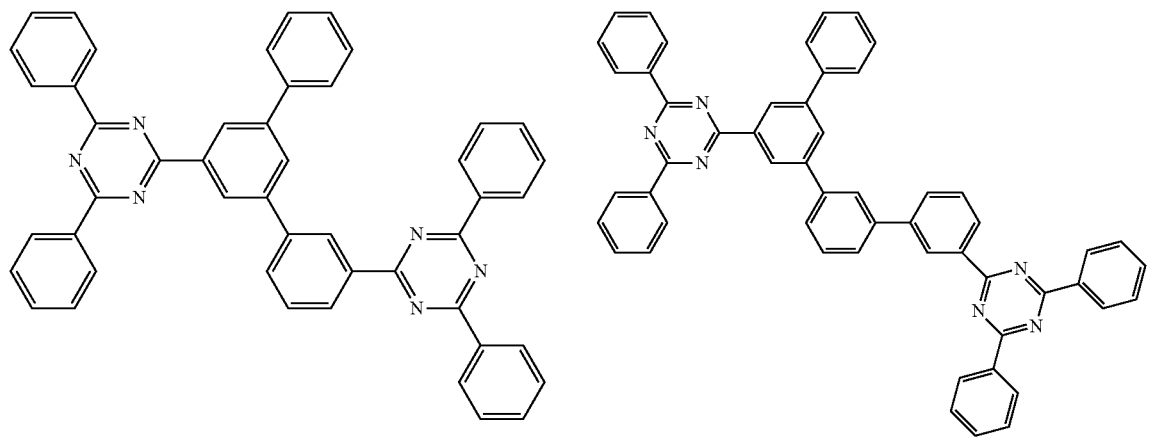
67
68
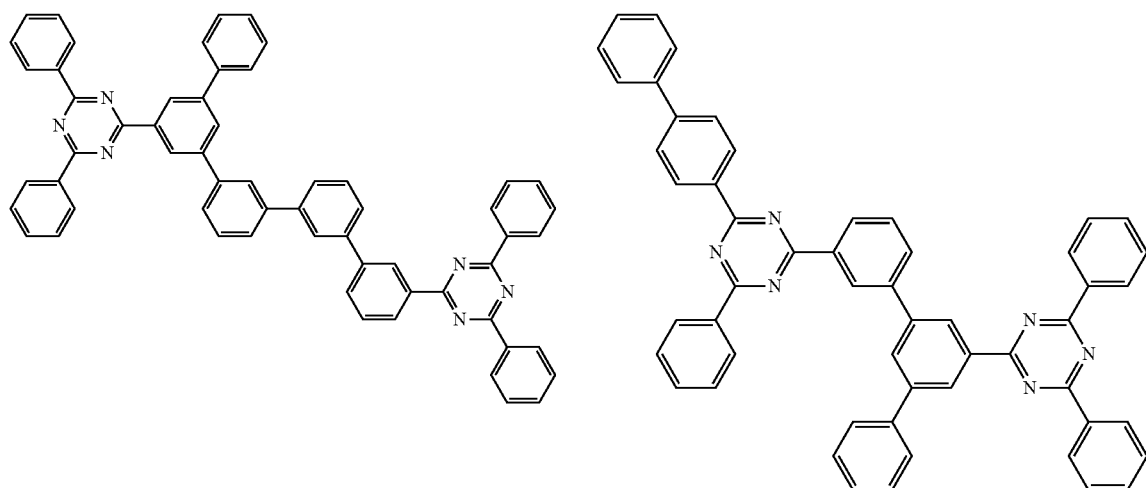
69
70

-continued
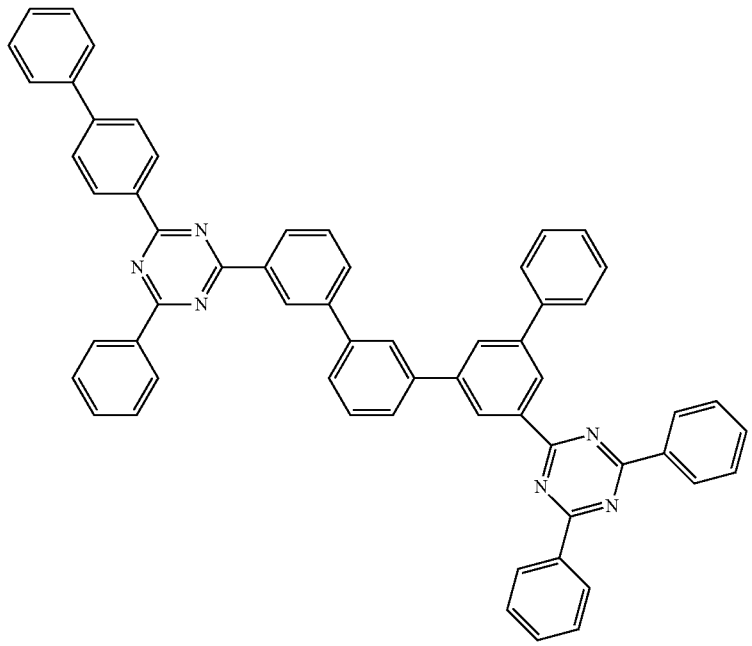
71
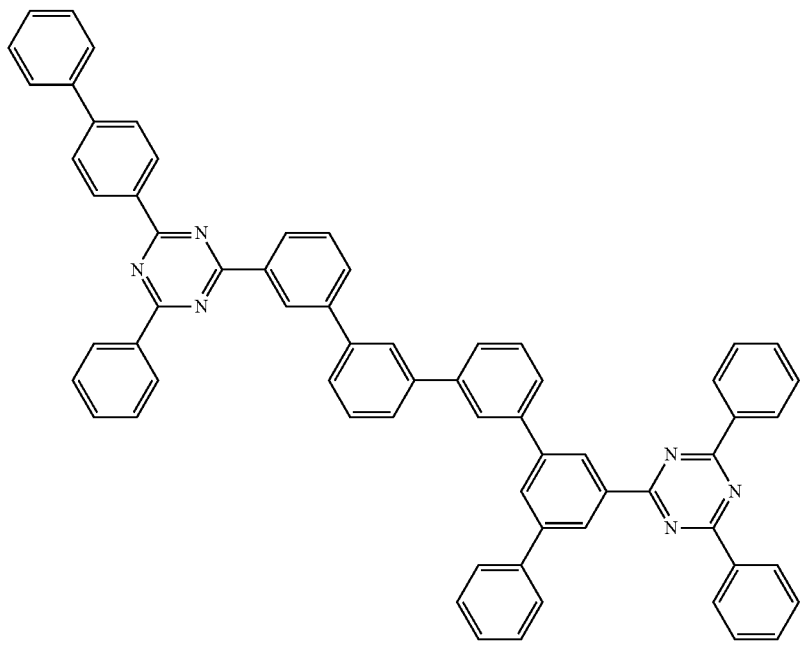
72
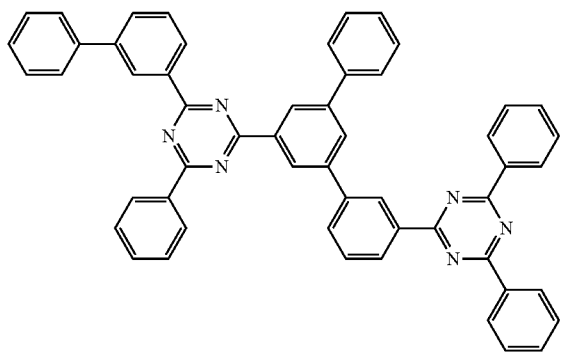
73

-continued
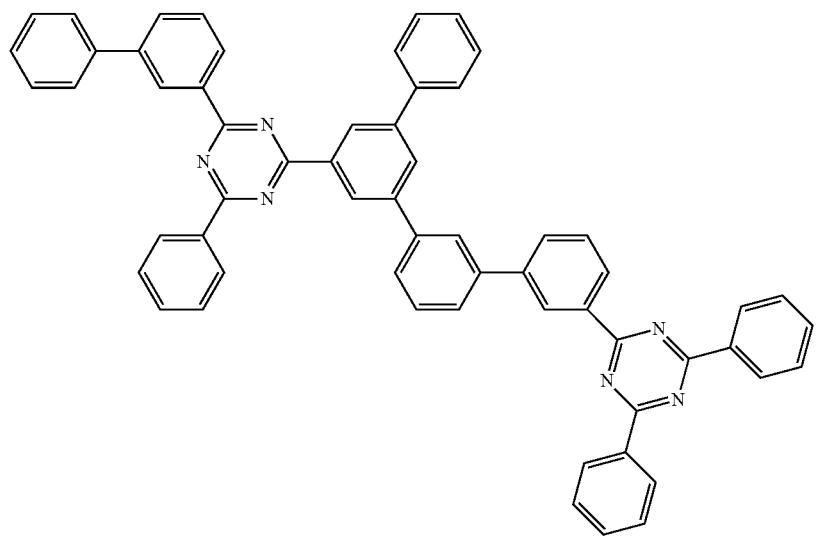
74
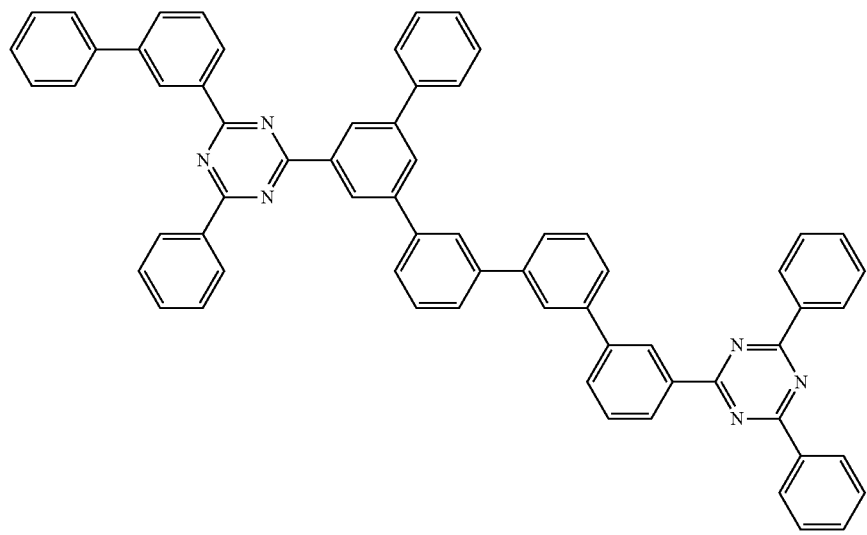
75
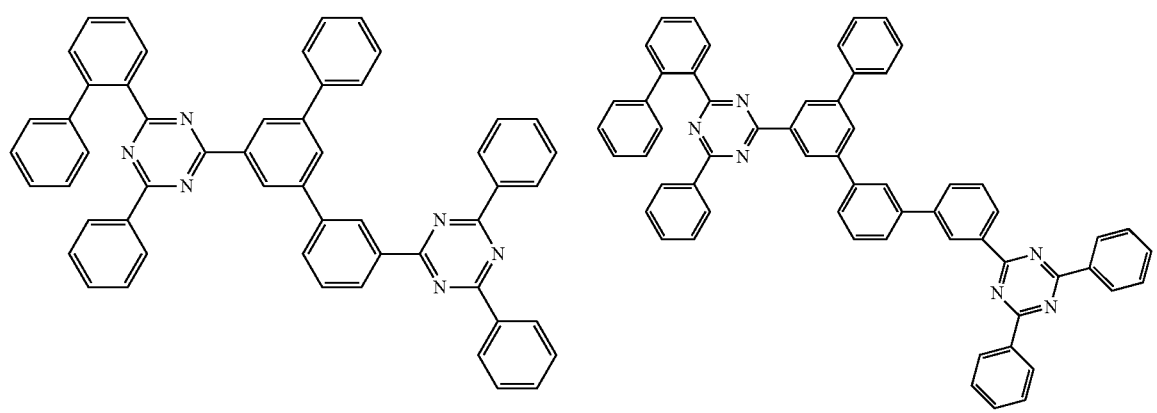
76  77

78
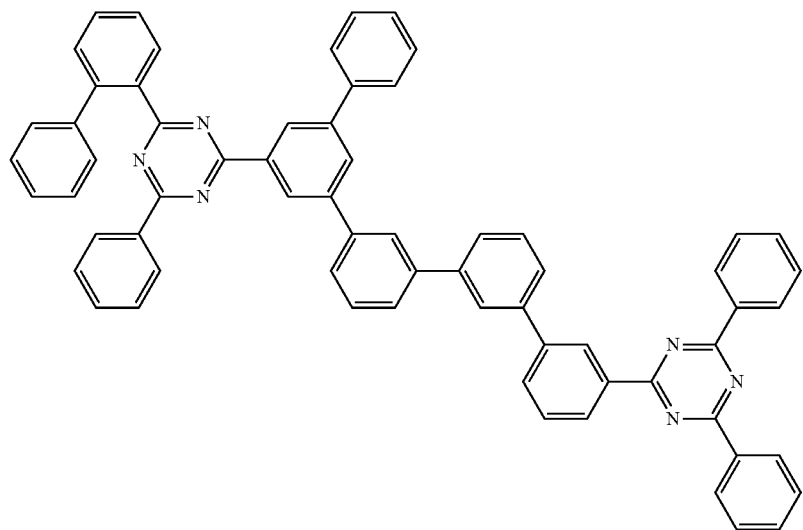
79    80
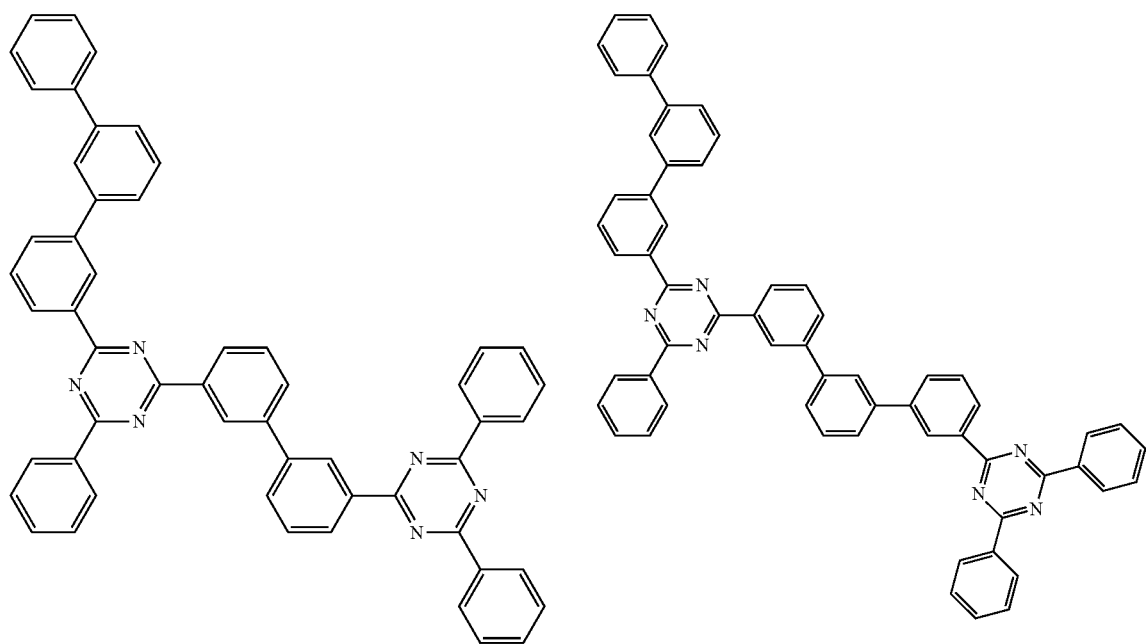

-continued
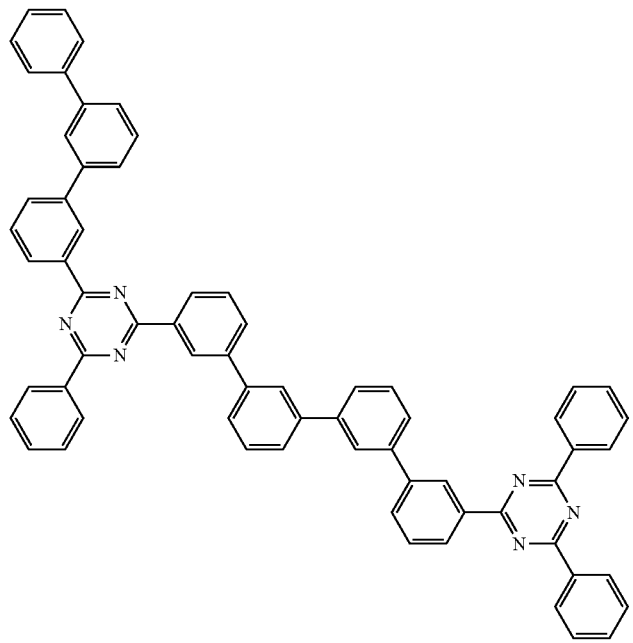
81
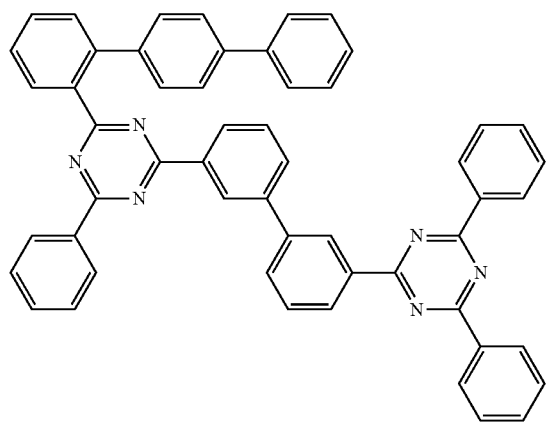
82
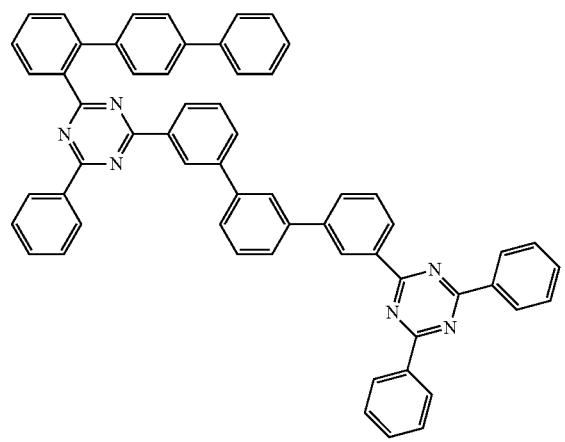
83

84
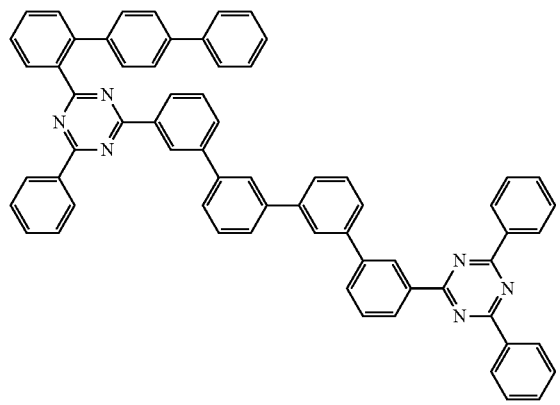
85
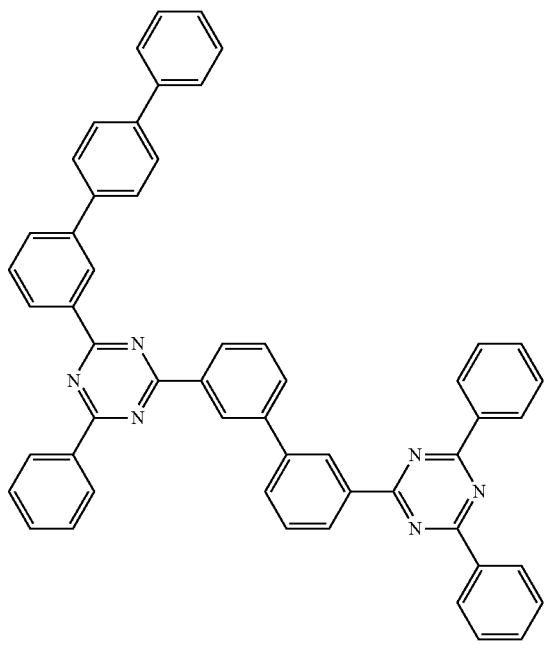
86
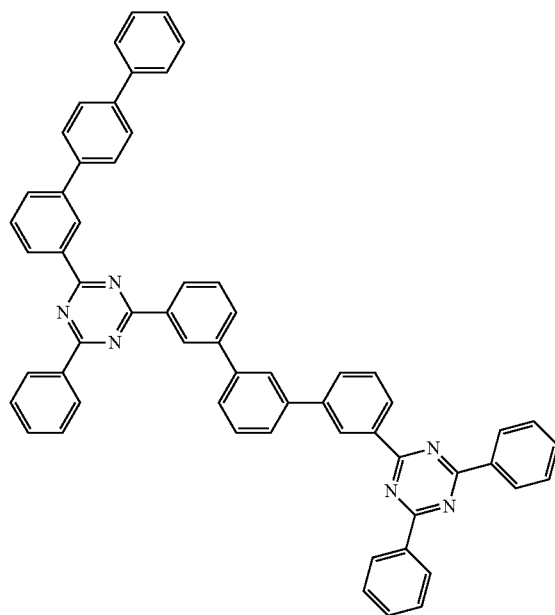
87
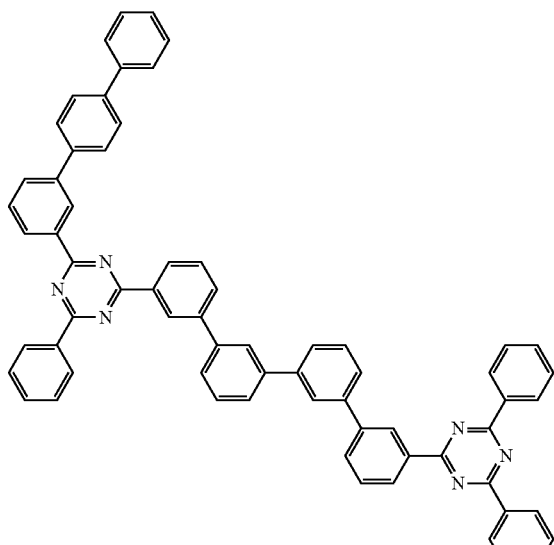

88
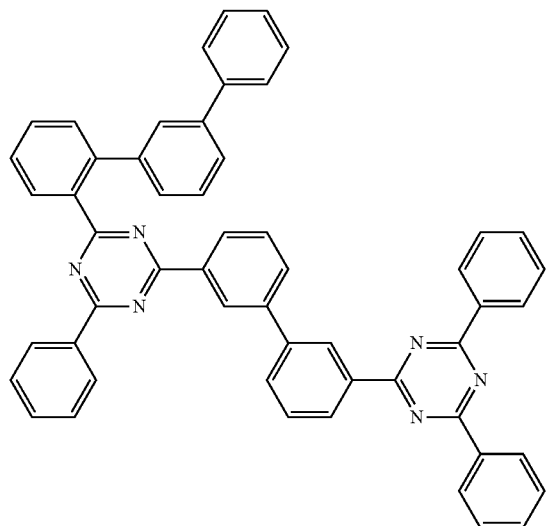
89
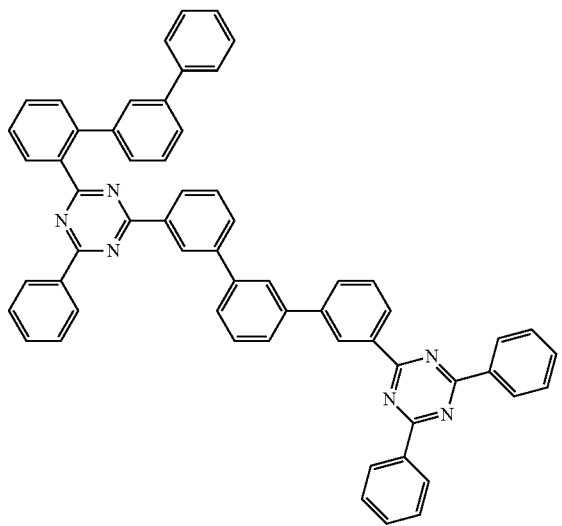
90
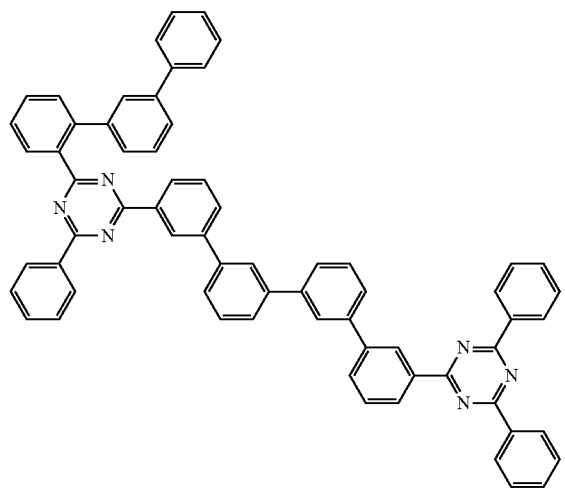
91
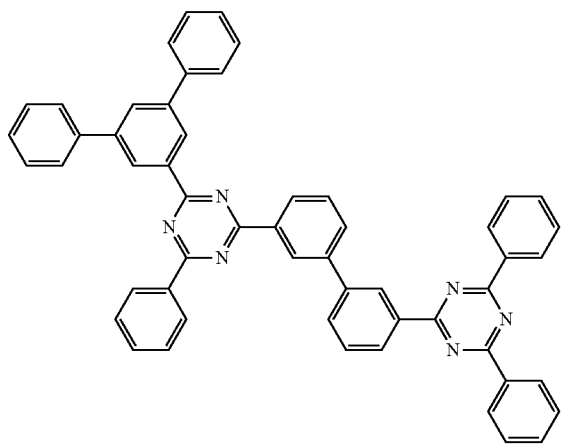

-continued
92
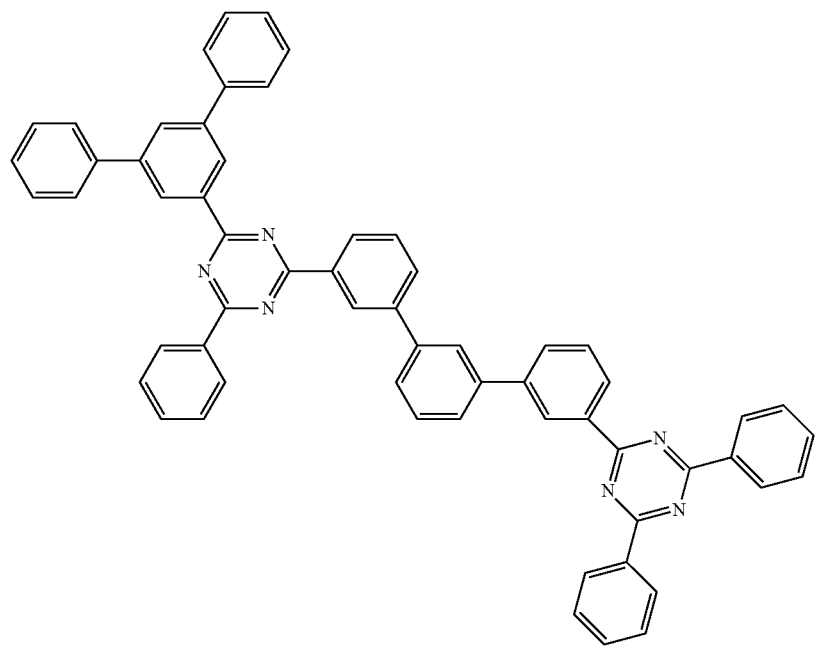
93
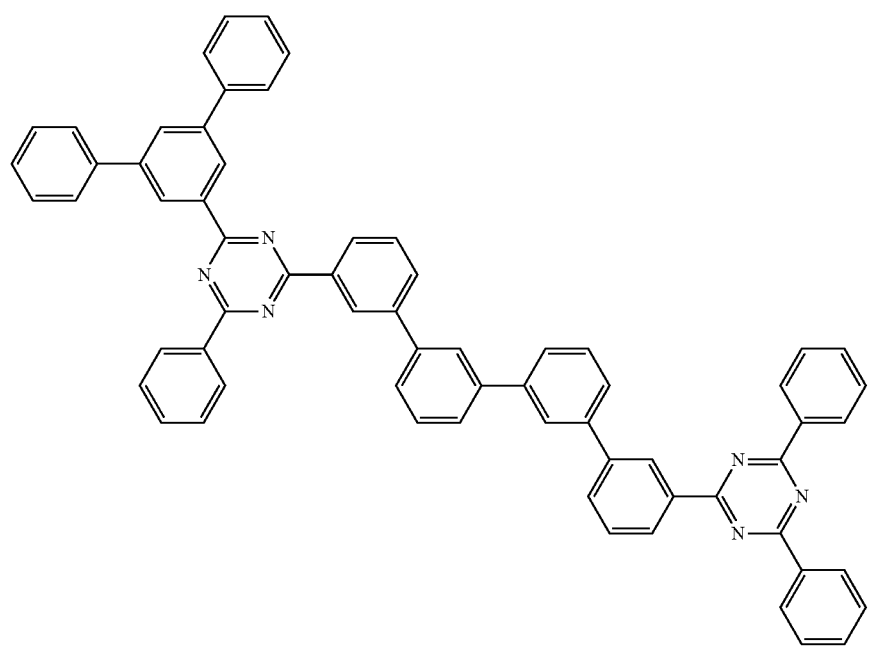

94
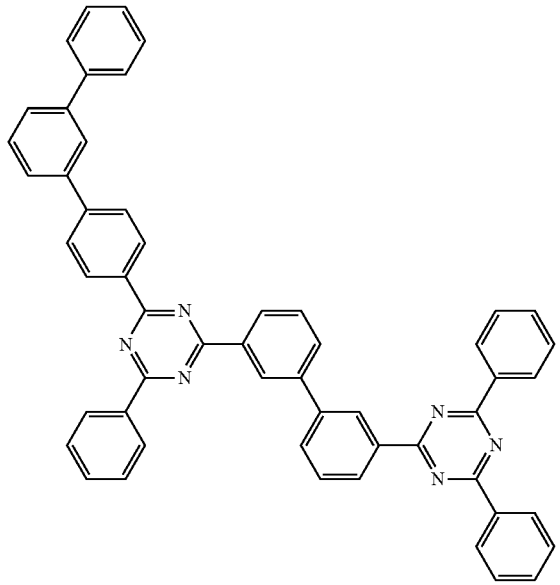
95
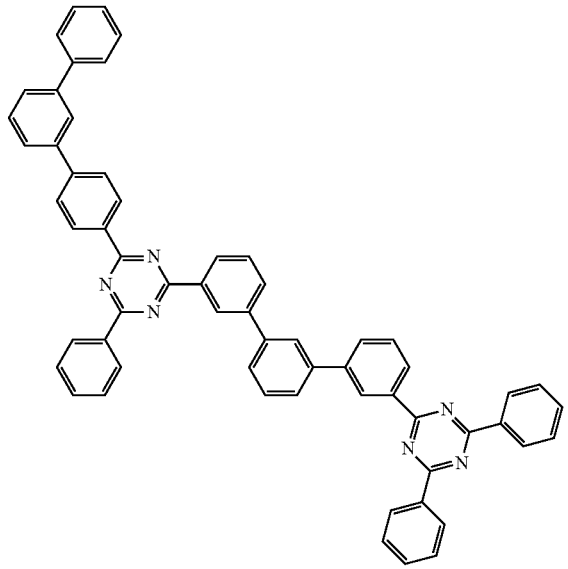
96
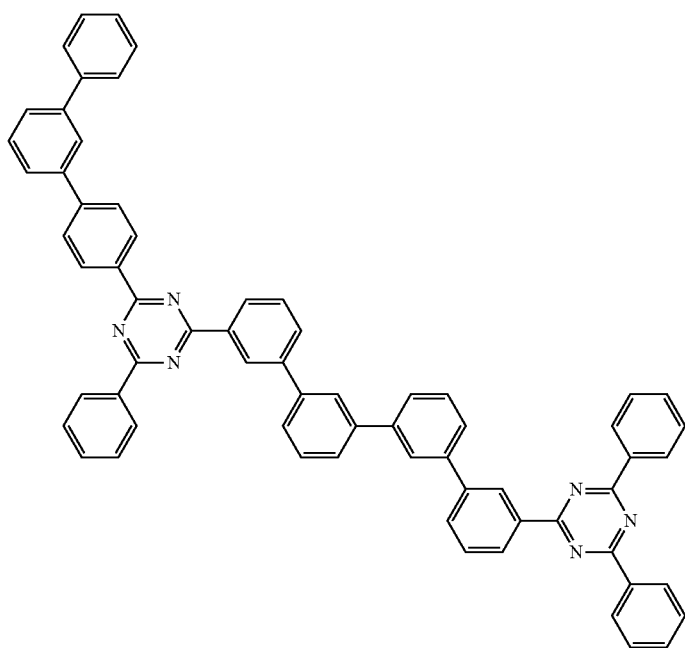

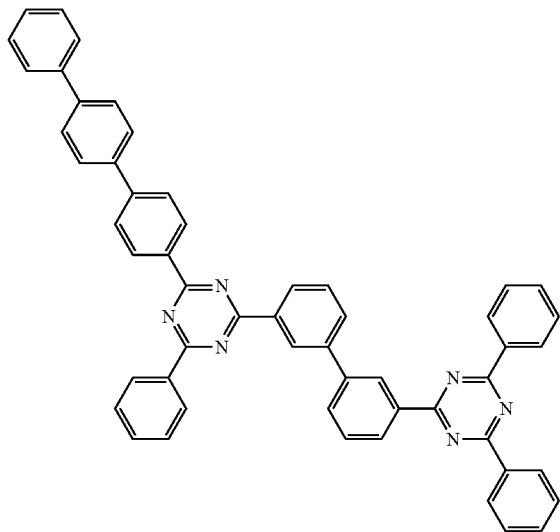
97
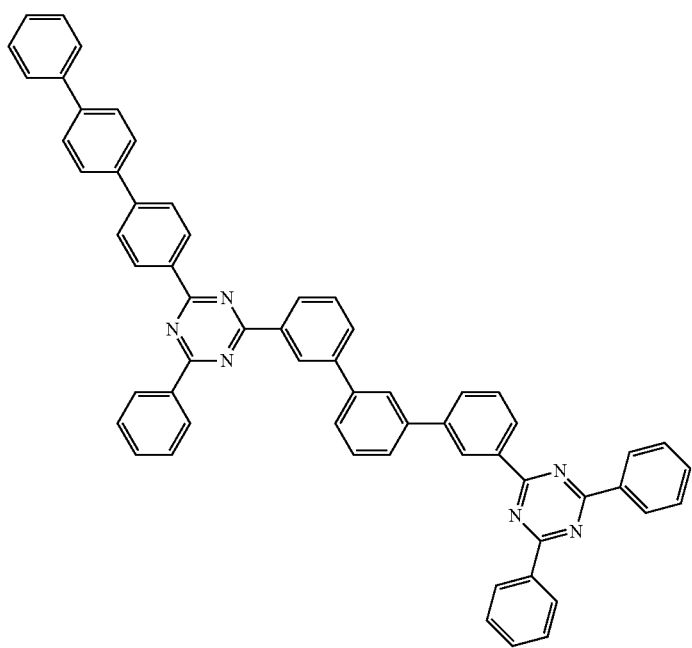
98

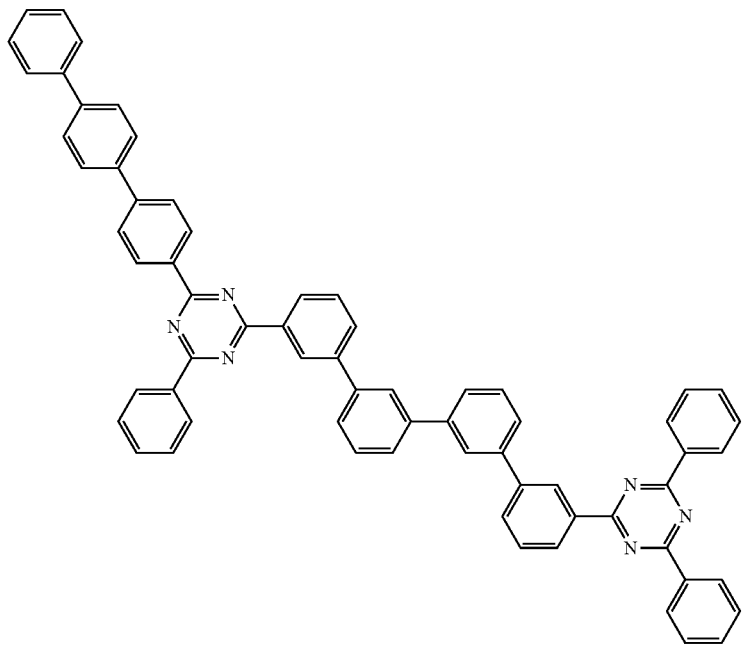
99
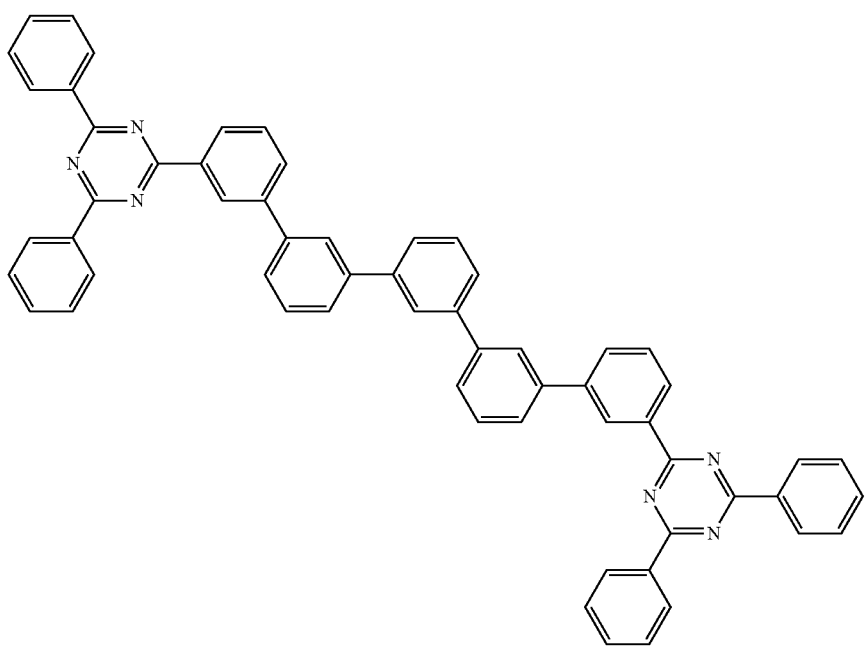
100

-continued
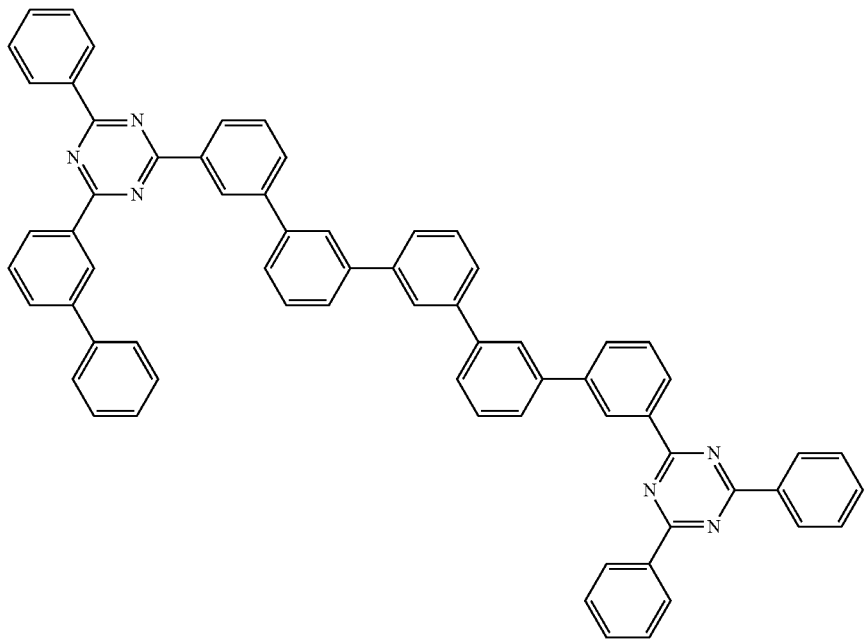
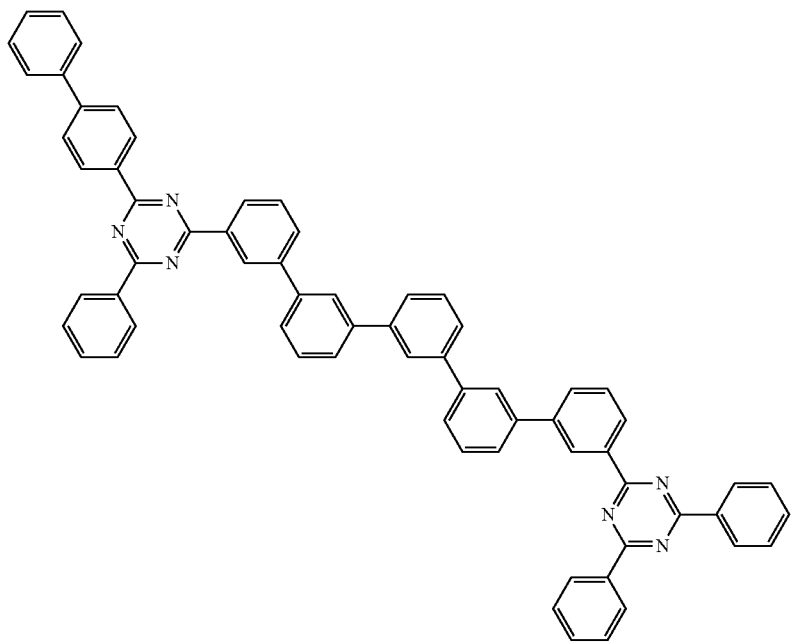

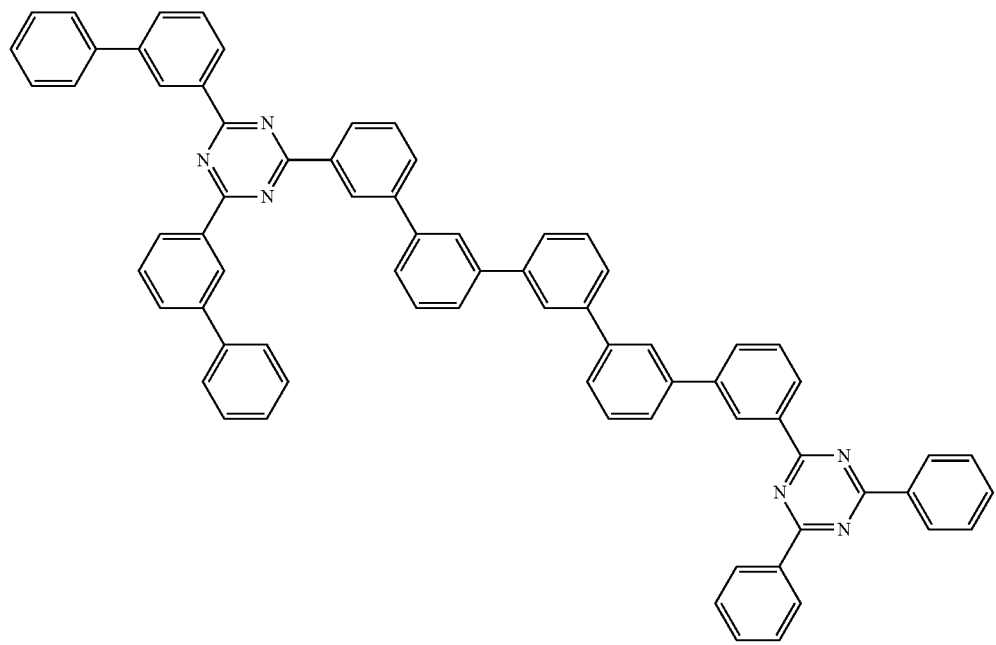
103
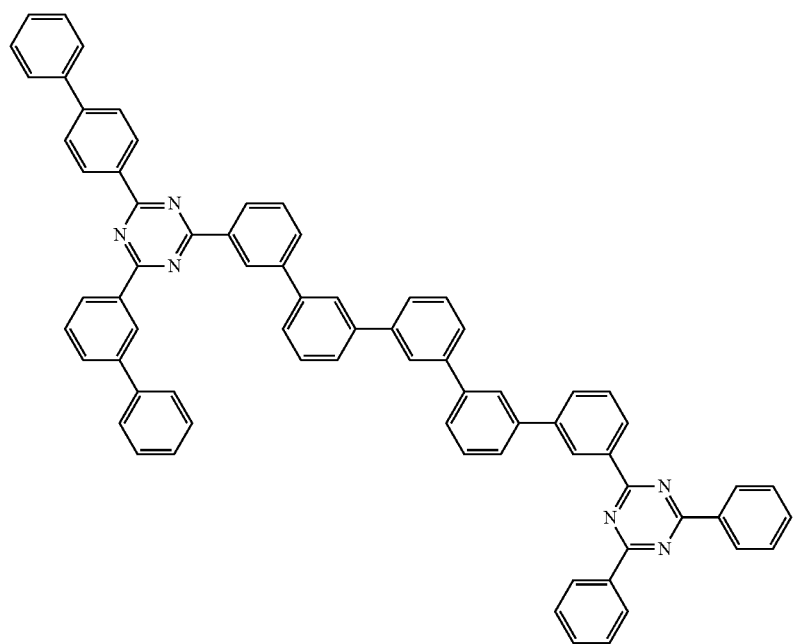
104

-continued
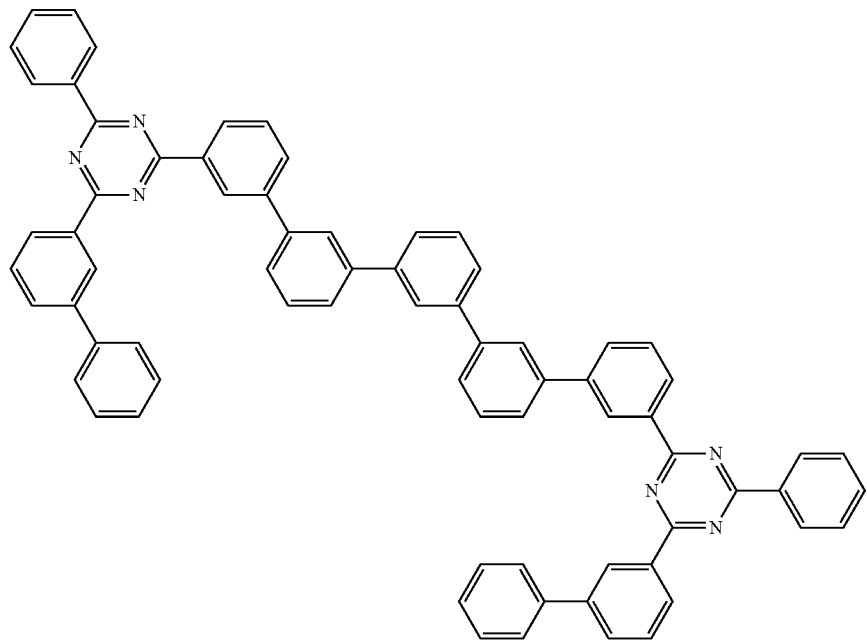
105
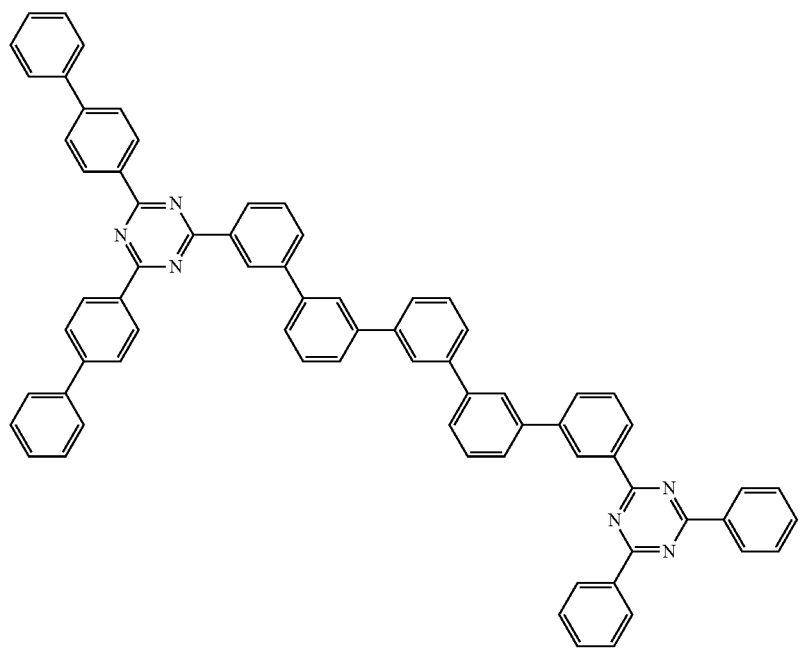
106

-continued
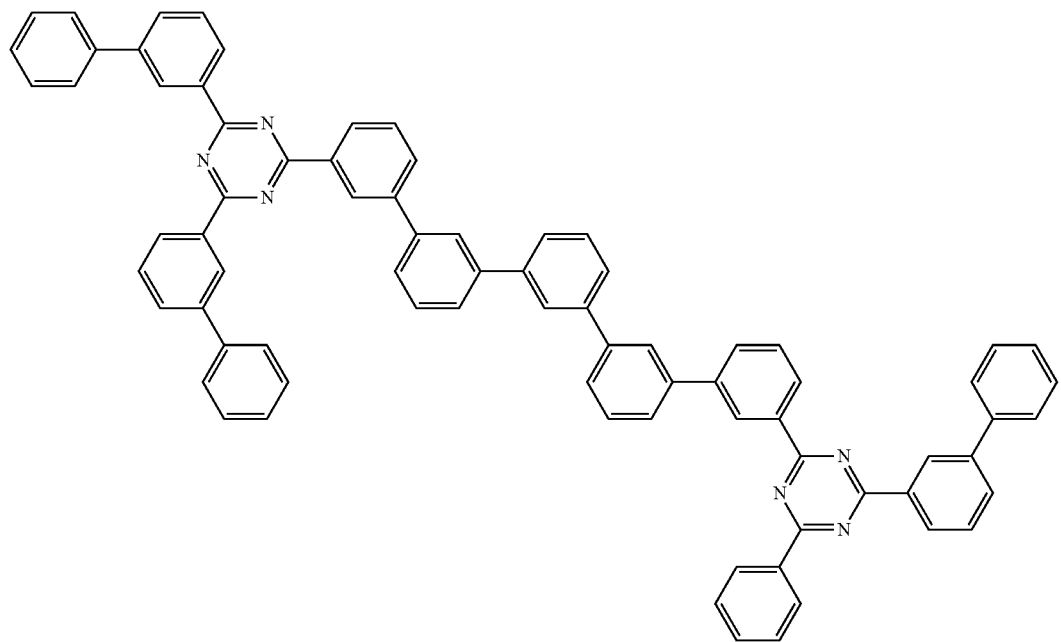
107
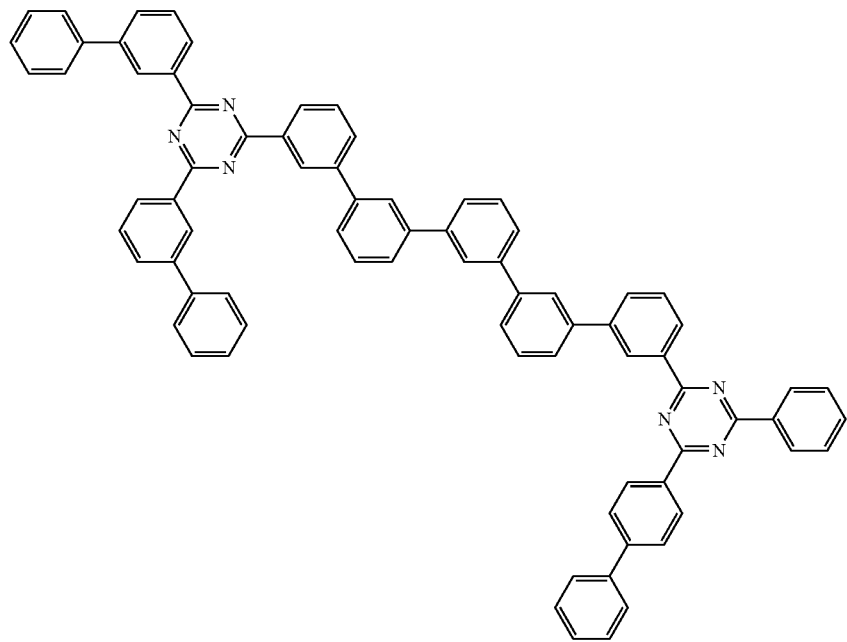
108

-continued
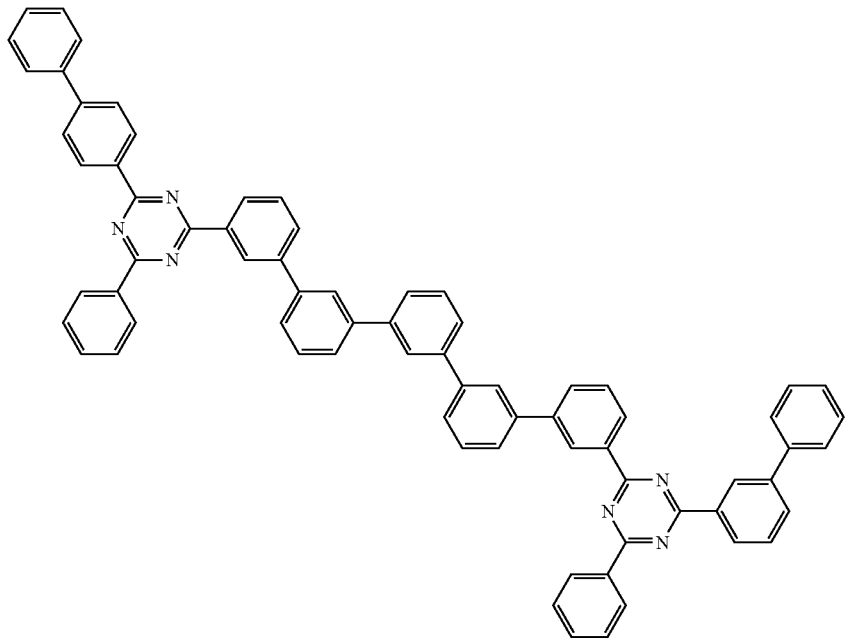
109
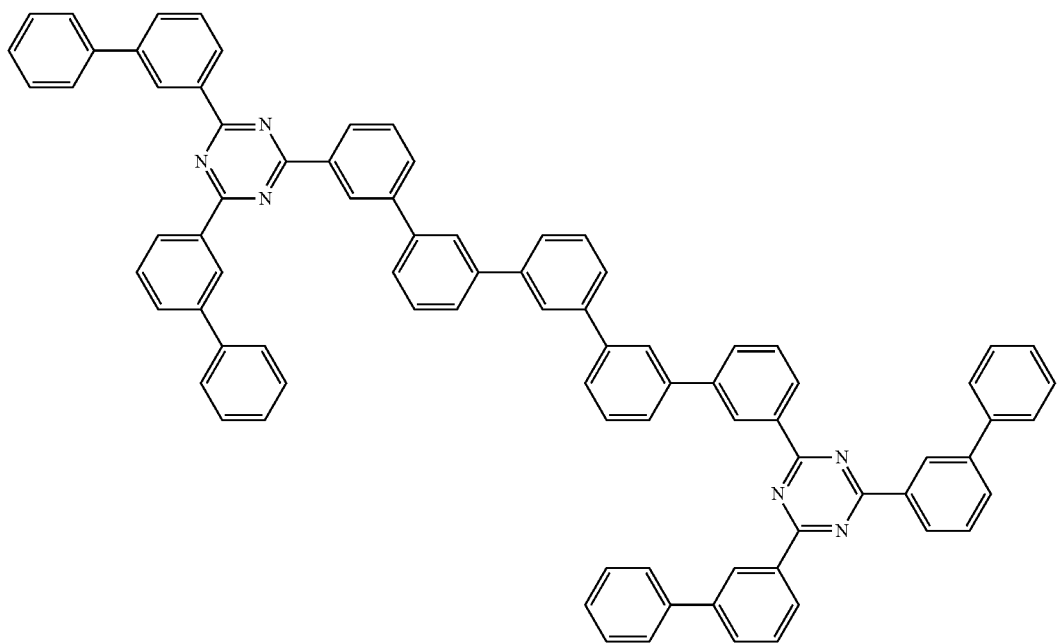
110

-continued

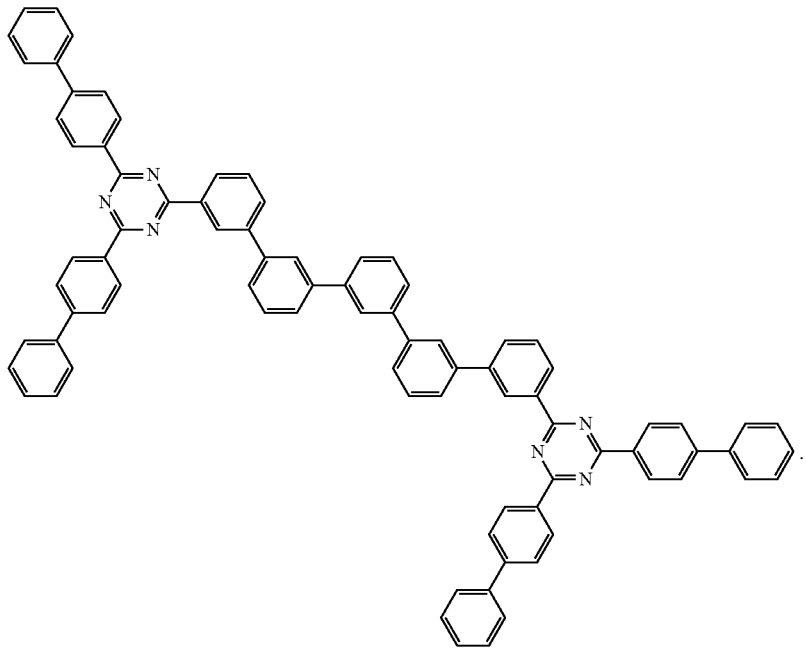

7. An organic optoelectric device, comprising
an anode and a cathode facing each other, and
at least one organic layer disposed between the anode and the cathode,
wherein the organic layer includes the compound for an organic optoelectric device of claim 1.

8. The organic optoelectric device of claim 7, wherein the organic layer includes a light emitting layer, and
the light emitting layer includes the compound for an organic optoelectric device.

9. The organic optoelectric device of claim 8, wherein the compound for an organic optoelectric device is included as a host of the light emitting layer.

10. The organic optoelectric device of claim 7, wherein the organic layer further includes at least one auxiliary layer selected from a hole blocking layer and an electron transport layer, and
the auxiliary layer includes the compound for an organic optoelectric device.

11. The organic optoelectric device of claim 10, wherein the auxiliary layer further includes an electron transport auxiliary layer that is adjacent to the light emitting layer, and
the electron transport auxiliary layer includes the compound for an organic optoelectric device.

12. A display device comprising the organic optoelectric device of claim 7.

* * * * *